US009497909B2

(12) United States Patent
Schaffer et al.

(10) Patent No.: US 9,497,909 B2
(45) Date of Patent: Nov. 22, 2016

(54) ISOLATED POLYPEPTIDES AND POLYNUCLEOTIDES ENCODING SAME FOR GENERATING PLANTS WITH INCREASED CUTICLAR WATER PERMEABILITY

(71) Applicant: The State of Israel, Ministry of Agriculture & Rural Development, Agricultural Research Organization, Beit-Dagan (IL)

(72) Inventors: Arthur A. Schaffer, Hashmonaim (IL); Ran Hovav, Yashresh (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 448 days.

(21) Appl. No.: 13/902,885

(22) Filed: May 27, 2013

(65) Prior Publication Data
US 2013/0316057 A1 Nov. 28, 2013

Related U.S. Application Data

(62) Division of application No. 11/663,151, filed as application No. PCT/IL2005/001000 on Sep. 19, 2005, now Pat. No. 8,481,809.

(30) Foreign Application Priority Data

Sep. 19, 2004 (IL) .......................................... 164125

(51) Int. Cl.
*A01H 5/08* (2006.01)
*C07K 14/415* (2006.01)
*C12N 15/82* (2006.01)

(52) U.S. Cl.
CPC ............... *A01H 5/08* (2013.01); *C07K 14/415* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 5,434,344 | A | 7/1995 | Bennett et al. |
| 5,557,883 | A | 9/1996 | Walker |
| 5,817,913 | A | 10/1998 | Schaffer |
| 7,119,261 | B1 | 10/2006 | Schaffer |
| 8,895,817 | B2 | 11/2014 | Schaffer |
| 2004/0003107 | A1 | 1/2004 | Barham et al. |
| 2004/0031072 | A1 | 2/2004 | La Rosa et al. |
| 2007/0022504 | A1 | 1/2007 | Schaffer |
| 2010/0095393 | A1 | 4/2010 | Schaffer |
| 2015/0067911 | A1 | 3/2015 | Schaffer |

FOREIGN PATENT DOCUMENTS

| | | | |
|---|---|---|---|
| EP | 1211926 | 11/2003 | |
| EP | 2131662 | 12/2009 | |
| IL | 125425 | 3/1999 | |
| WO | WO 00/05390 | 2/2000 | |
| WO | WO 01/13708 | * 3/2001 | ............... A01H 5/10 |
| WO | WO 2006/030445 | 3/2006 | |
| WO | WO 2008/119618 | 10/2008 | |
| WO | WO 2015/011713 | 1/2015 | |

OTHER PUBLICATIONS

Hovav et al. The Plant Journal, (2007); vol. 52, pp. 627-639.*
Monforte A.J. et al. Theoretical and Applied Genetics, (2001) vol. 102:572-590.*
Official Action Dated Jan. 12, 2015 From the US Patent and Trademark Office Re. U.S. Appl. No. 14/538,835.
Official Action Dated Jan. 16, 2014 From the US Patent and Trademark Office Re. U.S. Appl. No. 11/506,896.
Summons to Attend Oral Proceedings Pursuant to Rule 115(1) EPC Dated Mar. 10, 2014 From the European Patent Office Re. Application No. 08717525.3.
Schaffer Declaration of Arthur Schaffer Dated Feb. 16, 2006 in the Matter of Opposition EP-B1 1211926 of the State of Israel—Ministry of Agriculture.
Wikipedia "Australian Desert Raisin", Wikipedia, the Free Encyclopedia, 2 P., Jan. 31, 2006.
Applicant-Initiated Interview Summary Dated Apr. 11, 2014 From the US Patent and Trademark Office Re. U.S. Appl. No. 12/636,880.
International Preliminary Report on Patentability Dated Mar. 29, 2007 From the International Bureau of WIPO Re.: Application No. PCT/IL2005/001000.
Invitation to Pay Additional Fees Dated Apr. 25, 2006 From the International Searching Authority Re.: Application No. PCT/IL05/01000.
Office Action Dated Nov. 6, 2011 From the Israel Patent Office Re. Application No. 164125 and Its Translation Into English.
Office Action Dated Feb. 23, 2011 From the Israel Patent Office Re. Application No. 164125 and Its Translation Into English.
Office Action Dated Aug. 29, 2010 From the Israel Patent Office Re. Application No. 164125 and Its Translation Into English.
Official Action Dated Jul. 7, 2011 From the US Patent and Trademark Office Re. U.S. Appl. No. 11/663,151.
Official Action Dated Nov. 22, 2011 From the US Patent and Trademark Office Re. U.S. Appl. No. 11/663,151.
Official Action Dated May 23, 2012 From the US Patent and Trademark Office Re. U.S. Appl. No. 11/663,151.
Response Dated Nov. 1, 2010 to Notification of Reasons for Refusal of Jun. 15, 2010 From the Japanese Patent Office Re. Application No. 2001-517862.
Response Dated Sep. 7, 2011 to Official Action of Jul. 7, 2011 From the US Patent and Trademark Office Re. U.S. Appl. No. 11/663,151.
Translation of Notice of Reason for Rejection Dated Jan. 11, 2011 From the Japanese Patent Office Re. Application No. 2007-531955.
Aarts et al. "Molecular Characterization of the CER1 Gene of *Arabidopsis* Involved in Epicuticular Wax Biosynthesis and Pollen Fertility", The Plant Cell, 7: 2115-2127, Dec. 1995.

(Continued)

*Primary Examiner* — Russell Kallis

(57) ABSTRACT

An isolated polynucleotide is provided. The isolated polynucleotides comprising a nucleic acid sequence encoding a polypeptide having an amino acid sequence at least 88% homologous to SEQ ID NO: 22, the polypeptide being capable of increasing a cuticular water permeability of a plant expressing same. Also provided are methods of generating plants expressing such polypeptides which can be used for producing dehydrated plants or cuticular covered portions thereof.

6 Claims, 14 Drawing Sheets

(56) References Cited

OTHER PUBLICATIONS

Aharoni et al. "The SHINE Clade of AP2 Domain Transcription Factors Activates Wax Biosythesis, Alters Cuticle Properties, and Confers Drought Tolerance When Overexpressed in Arabidopsis", The Plant Cell, 16: 2463-2480, Sep. 2004.
Altschul et al. "Basic Local Alignment Search Tool", Journal of Molecular Biology, 215: 403-410, 1990.
Baker et al. "Composition of Tomato Fruit Cuticle as Related to Fruit Growth and Development", The Plant Cuticle, Academic Press, 33-44, 1982.
Bakker "Russeting (Cuticle Cracking) in Glasshouse Tomatoes in Relation to Fruit Growth", Journal of Horticultural Science, 63(3): 459-463, 1988.
Barg et al. "The TYLCV-Tolerant Tomato Line MP-1 Is Characterized by Superior Transformation Competence", Journal of Experimental Botany, 48(316): 1919-1923, Nov. 1997.
Blee et al. "Biosynthesis of Cutin Monomers: Involvement of a Lipzygenase/Peroxygenase Pathway", The Plant Journal, 4(1): 113-123, 1993.
Borden "RING Fingers and B-Boxes: Zinc-Binding Protein-Protein Interaction Domains", Biochemistry and Cell Biology, 76(2/3): 351-358, 1998.
Chen et al. "Cloning and Characterization of the WAX2 Gene of *Arabidopsis* Involved in Cuticle Membrane and Wax Production", The Plant Cell, 15: 1170-1185, 2003.
Considine et al. "Physical Aspects of Fruit Growth", Plant Physiology, 68: 371-376, 1981.
Cotner et al. "Pericarp Anatomy of Crack-Resistant and Susceptible Tomato Fruits", Journal of the American Society of Horticultural Science, 94: 136-137, 1969.
Dhalluin et al. "Structure and Ligand of a Histone Acetyltransferase Bromodomain", Nature, 399: 491-496, Jun. 3, 1999.
Ehret et al. "Cuticle Cracking in Tomato Fruit", Journal of Horticultural Science, 68(2): 195-201, 1993.
Eshed et al. "An Introgression Line Population of Lycopersicon Pennellii in the Cultivated Tomato Enables the Identification and Fine Mapping of Yield-Associated QTL", Genetics, 141: 1147-1162, Nov. 1995.
Fiebig et al. "Alterations in CER6, A Gene Identical to CUT1, Differentially Affect Long-Chain Lipid Content on the Surface of Pollen and Stems", The Plant Cell, 12: 2001-2008, Oct. 2000.
Fulton et al. "Advanced Backcross QTL Analysis of a Lycopersicon Esculentum X Lycopersicon Parviflorum Cross", Theoretical and Applied Genetics, 100: 1025-1042, 2000.
Fulton et al. "Microprep Protocol for Extraction of DNA From Tomato and Other Herbaceous Plants", Plant Molecular Biology Reporter, 13(3): 207-209, 1995.
Ghosh et al. "Cloning and Sequencing of Potato Virus Y Coat Protein Gene From an Indian Isolate and Development of Transgenic Tobacco for PVY Resistance", Current Science, 82(7): 855-859, Apr. 20, 2002.
Halford et al. "Isolation of a Gene Expressed During Early Embryogenesis From the Region of 22q11 Commonly Deleted in DiGeorge Syndrome", Human Molecular Genetics, 2(10): 1577-1582, 1993.
Holloway "Structure and Histochemistry of Plant Cuticular Membranes: An Overview", The Plant Cuticle, Academic Press, 1-33, 1982.
Hooker et al. "Significance of the Expression of the CER6 Condensing Enzyme for Cuticular Wax Production in Arabidopsis", Plant Physiology, 129: 1568-1580, Aug. 2002.
Kolattukudy "Biopolyester Membranes of Plants: Cutin and Suberin", Science, 208: 990-999, May 30, 1980.
Koske et al. "Influence of Ground Bed Heating and Cultiva on Tomato Fruit Cracking", HortScience, 15(6): 760-762, 1980.
Kunst et al. "Biosynthesis and Secretion of Plant Cuticular Wax", Progress in Lipid Research, 42: 51-80, 2003.
Kurata et al. "The YORE-YORE Gene Regulates Multiple Aspects of Epidermal Cell Differentiation in Arabidopsis", The Plant Journal, 36: 55-66, 2003.

Lownds et al. "Relationships Between Postharvest Water Loss and Physical Properties of Pepper Fruit (*Capsicum annuum* L.)", HortScience, 28(12): 1182-1184, 1993.
Meissner et al. "A New Model System for Tomato Genetics", The Plant Journal, 12(6): 1465-1472, 1997.
Millar et al. "CUT1, An Arabidopsis Gene Required for Cuticular Wax Biosynthesis and Pollen Fertility, Encodes a Very-Long-Chain Fatty Acid Condensing Enzyme", The Plant Journal, 11: 825-838, May 1999.
Miron et al. "Sucrose Phosphate Synthase, Sucrose Synthase, and Invertase Activities in Developing Fruit of Lycopersicon Esculentum Mill. and the Sucrose Accumulating Lycopersicon Hirsutum Humb. and Bonpl.", Plant Physiology, 95: 623-627, 1991.
Miron et al. "Sucrose Uptake, Invertase Localization and Gene Expression in Developing Fruit of Lycopersicon Esculentum and the Sucrose-Accumulating Lycopersicon Hirsutum", Physiologia Plantarum, 115: 35-47, 2002.
Monforte et al. "Comparison of a Set of Allelic QTL-NILs for Chromosome 4 of Tomato: Deductions About Natural Variation and Implications for Germplasm Utilization", Theoretical and Applied Genetics, 102: 572-590, 2001.
Nawrath "The Biopolymers Cutin and Suberin", The Arabidopsis Book, American Society of Plant Biologists, p. 1-14, Apr. 4, 2002.
Ojimelukwe "Effects of Processing Methods on Ascorbic Acid Retention and Sensory Characterics of Tomato Products", Journal of Food Science and Technology, 31(3): 247-248, 1994.
Peet "Fruit Cracking in Tomato", HortTechnology, 2(2): 216-223, Apr./Jun. 1992.
Peet et al. "Role of Excess Water in Tomato Fruit Cracking", HortScience, 30(1): 65-68, Feb. 1995.
Pruitt et al. "Fiddleread, A Gene Required to Suppress Epidermal Cell Interactions in Arabidopsis, Encodes a Putative Lipid Biosynthetic Enzyme", Proc. Natl. Acad. Sci. USA, 97(3): 1311-1316, Feb. 1, 2000.
Reina et al. "Plant Cutin Biosynthesis: The Involvement of a New Acyltransferase", Trends in Plant Science, 6(7): 296, Jul. 2001.
Riederer et al. "'Protecting Against Water Loss: Analysis of the Barrier Properties of Plant Cuticles", Journal of Experimental Botany, 52(363): Plants Under Stress Special Issue: 2023-2032, Oct. 2001.
Schnurr et al. "The Acyl-CoA Synthetase Encoded by LACS2 Is Essential for Normal Cuticle Development in Arabidopsis", The Plant Cell, 16: 629-642, Mar. 2004.
Schoenherr "Water Permeability of Isolated Cuticular Membranes: The Effect of Cuticular Waxes on Diffusion of Water", Planta, 131: 159-164, 1976.
Schoenherr "Water Permeability of Isolated Cuticular Membranes: The Effect of pH and Cations on Diffusion, Hydrodynamic Permeability and Size of Polar Pores in the Cutin Matrix", Planta, 128: 113-126, 1976.
Schoenherr et al. "Water Permeability of Plant Cuticles. Dependence of Permeability Coefficients of Cuticular Transpiration on Vapor Pressure Saturation Deficit", Planta, 144: 391-400, 1979.
Tanksley et al. "Advanced Backcross QTL Analysis in a Cross Between an Elite Processing Line of Tomato and Its Wild Relative L. Pimpinellifolium", Theoretical and Applied Genetics, 92: 213-224, 1996.
Tanksley et al. "High Density Molecular Linkage Maps of the Tomato and Potato Genomes", Genetics, 132: 1141-1160, Dec. 1992.
Todd et al. "KCS1 Encodes a Fatty Acid Elongase 3-Ketoacyl-CoA Aynthase Affecting Wax Biosynthesis in Arabidopsis Thaliana", The Plant journal, 17(2): 119-130, 1999.
Tukey "Observations on the Russeting of Apples Growing in Plastic Bags", Proceedinga of the American Society for horticultural Science, 74: 30-39, 1959.
Vogg et al. "Tomato Fruit Cuticular Waxes and Their Effects on Transpiration Barrier Properties: Functional Characterization of a Mutant Deficient in a Very-Long-Chain Fatty Acid ?-Ketoacyl-CoA Synthase", Journal of Experimental Botany, 55(401): 1401-1410, Jun. 2004.

(56) References Cited

OTHER PUBLICATIONS

Voisey et al. "Tomato Skin Strength—Its Measurement and Relation to Cracking", Journal of the American Society of Horticultural Science, 95(4): 485-488, 1970.
Walkerpeach et al. "Agrobacterium-Mediated Gene Transfer to Plant Cells: Cointegrate and Binary Vector Systems", Plant Molecular Biology Manual, Kluwer Academic Publishers, PMAN-B1/1-PMAN-B1/19, 1994.
Wellesen et al. "Functional Analysis of the Lacerata Gene of *Arabidopsis* Provides Evidence for Different Roles of Fatty Acid ?-Hydroxylation in Devlopment", Proc. Natl. Acad. Sci. USA, 98(17): 9694-9699, Aug. 14, 2001.
Whaley Emmons et al. "Environmental and Physiological Effects on Cuticle Cracking in Tomato", Journal of the American Society of Hort Science, 122(6): 797-801, 1997.
Wilson et al. "Studies on the Cuticle of Tomato Fruit. I. Fine Structure of the Cuticle", Zeitung der Pflanzenphysiolgie, 77: 359-371, 1976.
Yephremov et al. "Characaterization of the Fiddlehead Gene of *Arabidopsis* Reveals a Link Between Adhesion Response and Cell Differentiation in the Epidermis", The Plant Cell, 11: 2187-2201, Nov. 1999.
Young "Cuticle Cracks in Tomato Fruits", Phytopathology, 37: 143-145, 1947.
Summons to Oral Proceedings Pursuant to Rule 115(1) EPC Dated Jun. 25, 2014 From the European Patent Office Re. Application No. 00940724.8.
Official Action Dated Jun. 18, 2013 From the US Patent and Trademark Office, Re. U.S. Appl. No. 11/506,896.
International Search Report and the Written Opinion Dated Oct. 21, 2014 From the International Searching Authority Re. Application No. PCT/IL2014/050677.
Translation of Decision of Rejection Dated Aug. 27, 2013 From the Japanese Patent Office Re. Application No. 2011-106718.
Translation of Notification of Reasons for Rejection Dated Sep. 3, 2013 From the Japanese Patent Office Re. Application No. 2001-517862.
Search Report and Report of Technical Examination Opinion Dated Oct. 26, 2015 From the Servico Publico Federal, ministerio do DesenvoMmento, Industria e Comercio Exterior, Instituto Nacional da Propriedade Industrial do Brazil Re. Application No. PI0515680-7 and Its Summary in English.
Summons to Oral Proceedings Pursuant to Rule 115(1) EPC Dated Jul. 20, 2015 From the European Patent Office Re. Application No. 00940724.8.
Summons to Oral Proceedings Pursuant to Rule 115(1) EPC Dated Jun. 25, 2015 From the European Patent Office Re. Application No. 00940724.8.
International Preliminary Report on Patentability Dated Jul. 27, 2015 From the International Preliminary Examining Authority Re. Application No. PCT/IL2014/050677.

* cited by examiner

Figs. 1a-b
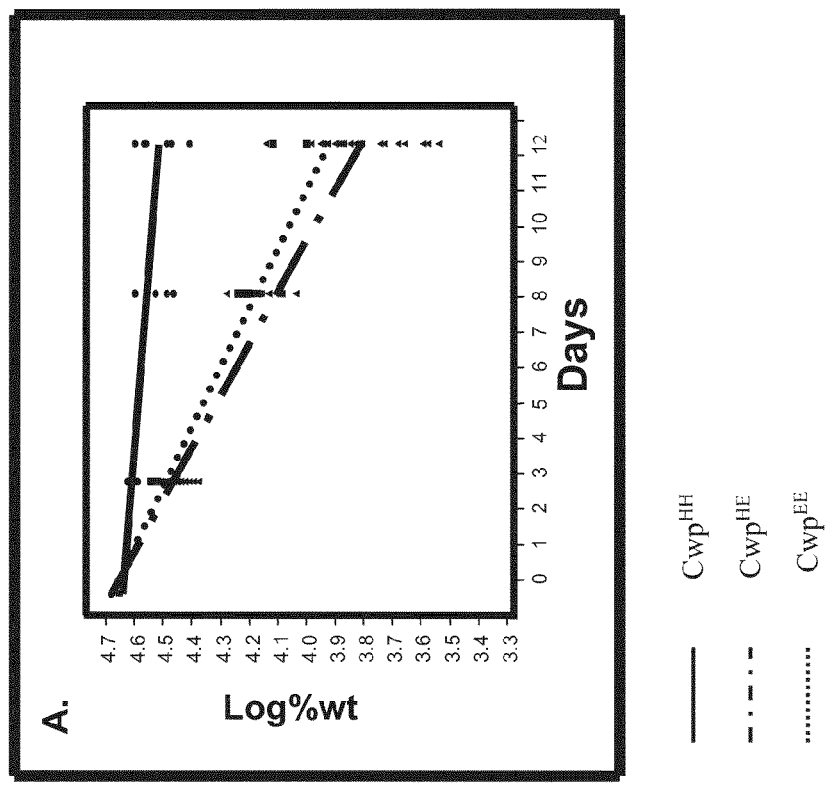

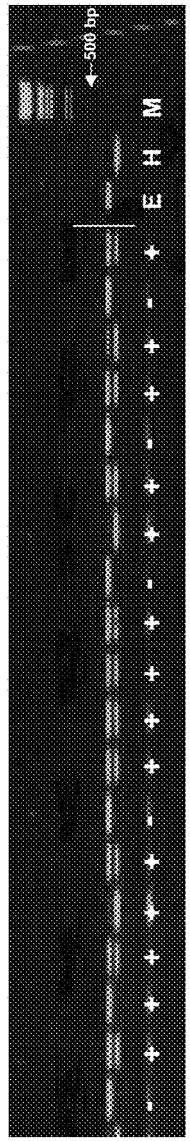
Fig. 2A.
Dehydrating status
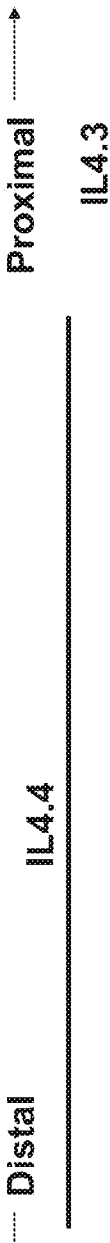
Fig. 2B.
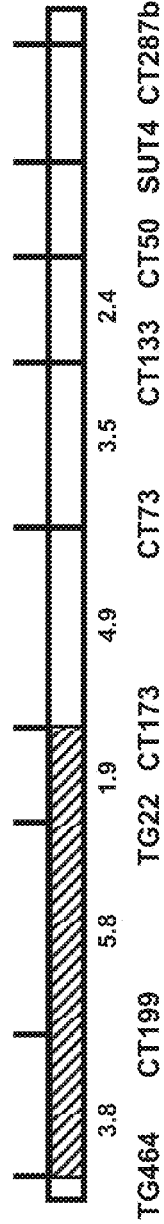
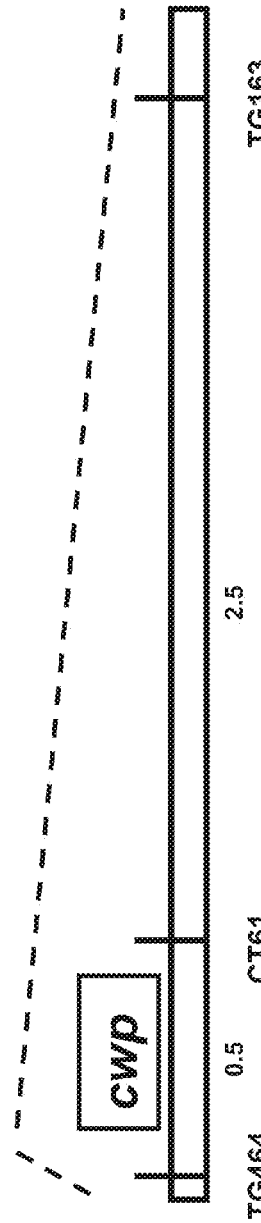
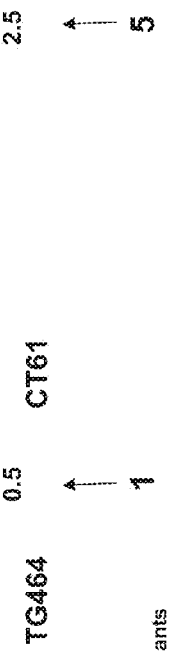
Fig. 2C.
No. of Recombinants

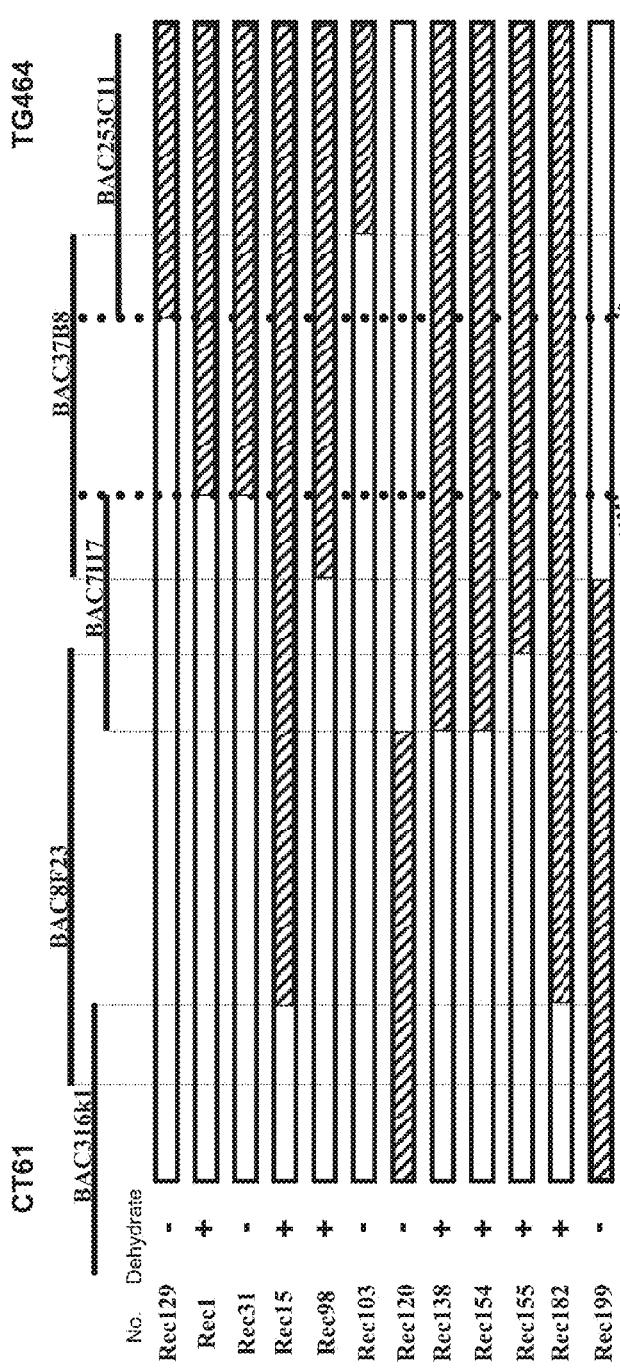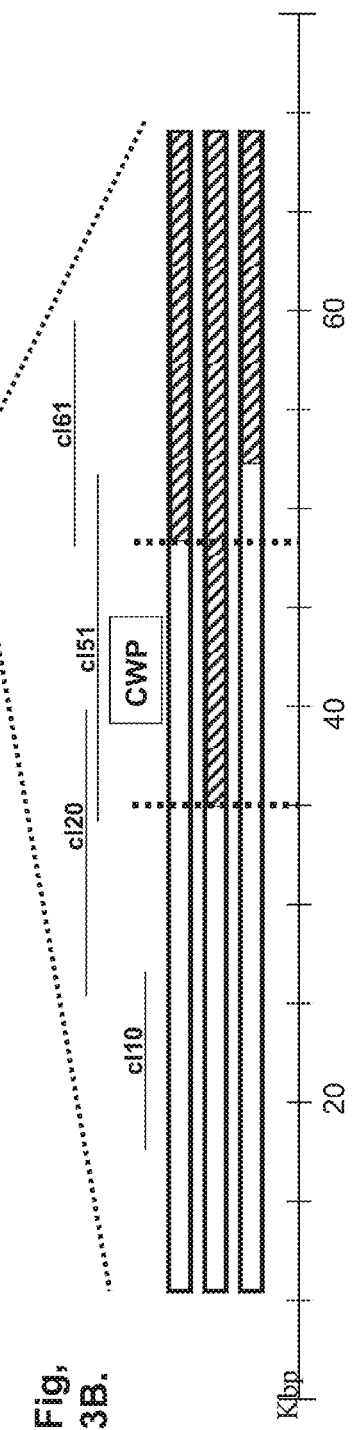
Fig. 3A.
Fig. 3B.

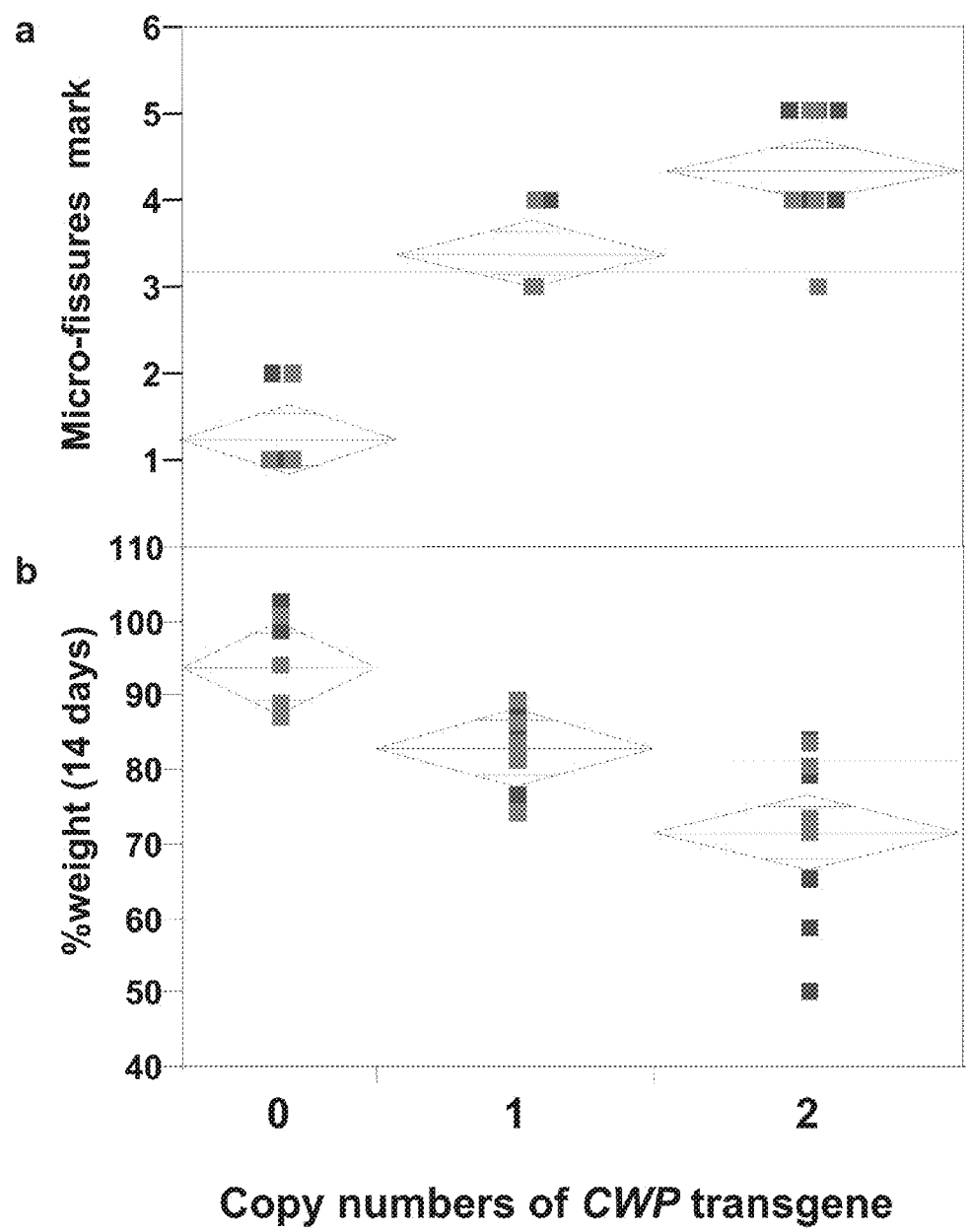

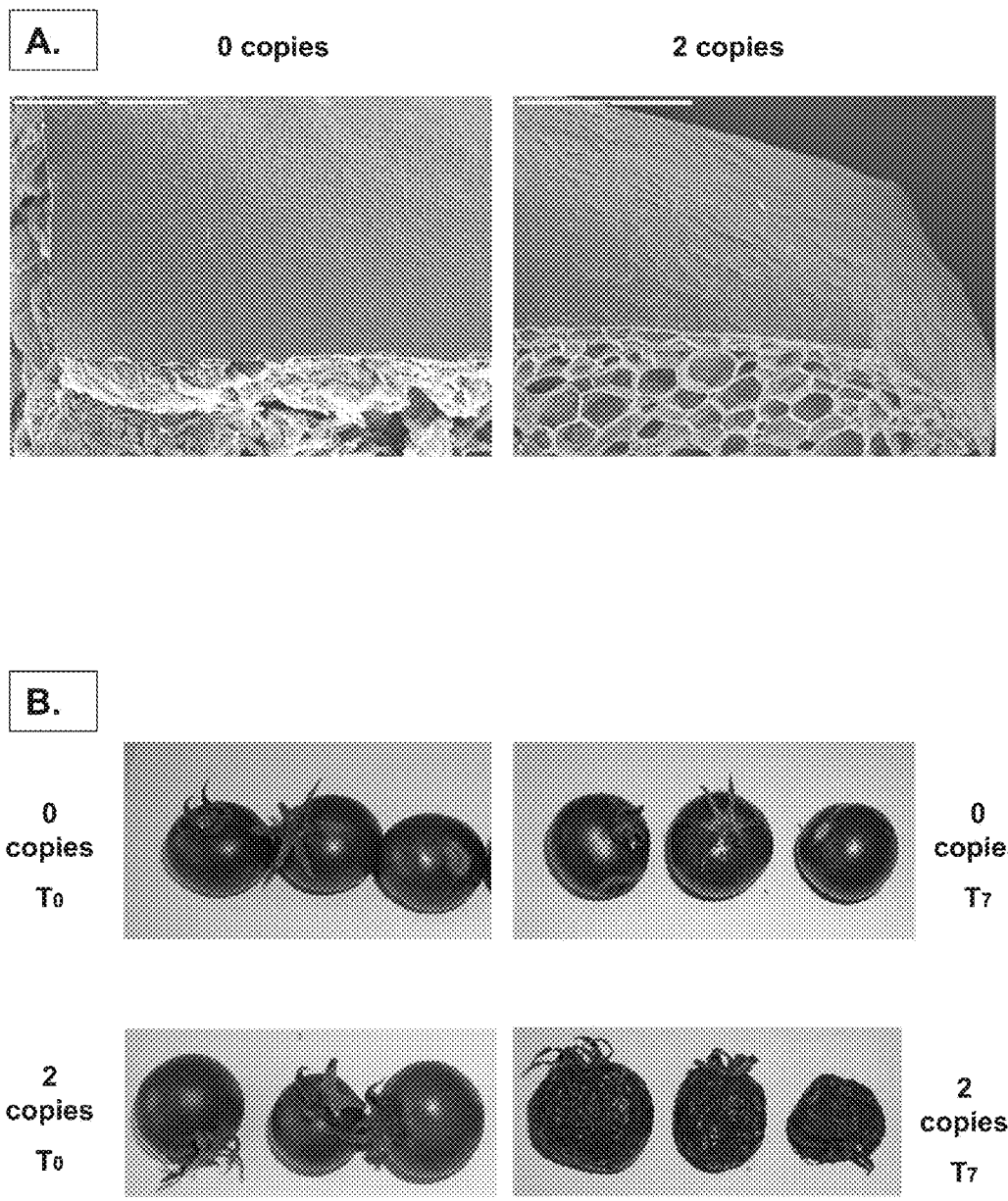
Figs. 9a-b

```
CWP1_1-270_                        --
virt|Capsicum                      --
Lycopersicon                       --
virt|Solanum                       --
Vitis                              --
virt|Beta                          --
virt|Medicago                      --
virt|Glycine                       --
Zea                                --
virt|Sorghum                       --
virt|Saccharum                     --
Oryza                              --
Hordeum                            --
virt|Triticum                      --
virt|Lactuca                       --
At4g38260_Translation_1-253_       --
At1g20740_Translation_1-266_       --
At1g20680_Translation_1-373_       VG 373
```

Fig 11c

SEQUENCE LISTING

```
<160> NUMBER OF SEQ ID NOS: 58

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
tgtaatacga ctcactatag gg                                          22

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
aagctattta ggtgacacta tag                                         23
```

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
tgcaatcccg aacatgaaga c                                          21

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ccttctggtc gcatctgtgt ct                                         22

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
tcagggtgag gggtaataat tgag                                       24

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 6
gcttaaaact caagtctcct cgca                                       24

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
aataatgcga atcgaatcac ta                                         22

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
aaggctaaat ctcctccttt ct                                         22

<210> SEQ ID NO 9
<211> LENGTH: 140
<212> TYPE: DNA
<213> ORGANISM: Artificial sequence
<220> FEATURE:

<223> OTHER INFORMATION: Tomato ZINC gene amplicon

<400> SEQUENCE: 9
aataatgcga atcgaatcac tatagtttaa acataggctt acttataata agagcggcgc    60
aactacatca acttactgta aagaatcaaa gaaaaactat ttttactatg ttgcatccag   120
aaaggaggag atttagcctt                                               140

<210> SEQ ID NO 10
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 10
tggataagcg gacgactcta ttg                                            23

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
ctgttgtttg ggaagtggct tct                                            23

<210> SEQ ID NO 12
<211> LENGTH: 116
<212> TYPE: DNA
<213> ORGANISM: Artificial sequence
<220> FEATURE:
<223> OTHER INFORMATION: Tomato DBP gene amplicon

<400> SEQUENCE: 12
tggataagcg gacgactcta ttggccctcc atcttctccc acccatccag gaccaaactt    60
taccccggga ggcaaaatat tttctaactt tttagaagcc acttcccaaa caacag       116

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
ctctccttgg cccaaggctc aa                                             22

<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14
cagctttagt ggtatctctc atca                                           24

<210> SEQ ID NO 15
<211> LENGTH: 205
<212> TYPE: DNA
<213> ORGANISM: Artificial sequence
<220> FEATURE:
<223> OTHER INFORMATION: Tomato PUT gene amplicon

<400> SEQUENCE: 15

```
ctctccttgg cccaaggtaa gaattctaat gggcttttt cgatcgatat acataaatta      60
tacaaatgat atgcttttgg ttgttcattt caggctcaaa gactgaagtt aaattttaag    120
aaaatgatgg atgtttacga agtgaatgac gagaaaatct gcgtcaaaga tatgatagaa   180
aaattgatga gagataccac taaag                                          205
```

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16

```
caccattggg tctgagcgat                                                 20
```

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17

```
gggcgacaac cttgatcttc                                                 20
```

<210> SEQ ID NO 18
<211> LENGTH: 251
<212> TYPE: DNA
<213> ORGANISM: Artificial sequence
<220> FEATURE:
<223> OTHER INFORMATION: Tomato actin amplicon

<400> SEQUENCE: 18

```
caccattggg tctgagcgat tccgctgtcc agaagtgctg ttccaaccat caatgatcgg     60
aatggaagct gctggtattc atgaaaccac gtacaattcc atcatgaagt gtgacgttga   120
tatcaggaag gatctgtatg gaaacatcgt cctcagtggt ggtaccacaa tgttccctgg   180
tattgctgat aggatgagca aggaaattac tgcattagct cctagtagca tgaagatcaa   240
ggttgtcgcc c                                                         251
```

<210> SEQ ID NO 19
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 19

```
gtagtactat ataaaccatg tgag                                            24
```

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20

```
catatgttga catatctaat g                                               21
```

<210> SEQ ID NO 21
<211> LENGTH: 912
<212> TYPE: DNA
<213> ORGANISM: Lycopersicon hirsutum

<400> SEQUENCE: 21

```
tgatcttcat cttattcttg tttttattta tagaaacaat aaaatattta taatcaatca      60
tcatgtgtat agtagtgttt atttgggaag cagatagtag atattcatta gtgttattat     120
tgaatagaga tgaatatcat aataggccaa caaaggaagt tcattggtgg aagatggag     180
aaattgttgg tggcaaagat gaagttggtg gtggcacttg gttggcttct tcaactaatg     240
gtaaattggc ttttcttact aatgttttgg aacttcatac acttcctcat gtcaaaacta     300
gaggtgacct acctcttcga tttttacaga gcaataaaag cccaatggag tttgcaaaag     360
agttggtgaa tgaagggaat gaatacaatg ggtttaattt aattttggca gatattgaaa     420
ctaaaaaaat ggtatatgta acaaataggc ccaaggaga gcccataaca atacaagaag     480
tccaaccagg tattcatgtg ctgtccaatg caaaactgga ctctccttgg cccaaggctc     540
aaagactgaa gttaaatttt aagaaaatgt tggatgttta cgaagtgaat gacgagaaaa     600
tctgcgtcaa agatatgata gaaaaattga tgagagatac cactaaagct gataaaagta     660
aattgccttg tatttgttct acagactggg agttggaact tagctctatt ttcgtggaag     720
ttgacactgc actggggtgt tatggtacta gaagtacaac agcattgaca attgaagtgg     780
gaggagaagt aagcttttat gagttgtacc ttgagaacaa catgtggaaa gagcaaattg     840
tcaactatcg gattgaaaaa ctccaaatgc aataaatgtt tttaatatgt tgatatatct     900
aatgttttca tg                                                          912
```

<210> SEQ ID NO 22
<211> LENGTH: 270
<212> TYPE: PRT
<213> ORGANISM: Lycopersicon hirsutum

<400> SEQUENCE: 22

```
Met Cys Ile Val Val Phe Ile Trp Glu Ala Asp Ser Arg Tyr Ser Leu
  1               5                  10                  15

Val Leu Leu Leu Asn Arg Asp Glu Tyr His Asn Arg Pro Thr Lys Glu
             20                  25                  30

Val His Trp Trp Glu Asp Gly Glu Ile Val Gly Gly Lys Asp Glu Val
         35                  40                  45

Gly Gly Gly Thr Trp Leu Ala Ser Ser Thr Asn Gly Lys Leu Ala Phe
     50                  55                  60

Leu Thr Asn Val Leu Glu Leu His Thr Leu Pro His Val Lys Thr Arg
 65                  70                  75                  80

Gly Asp Leu Pro Leu Arg Phe Leu Gln Ser Asn Lys Ser Pro Met Glu
                 85                  90                  95

Phe Ala Lys Glu Leu Val Asn Glu Gly Asn Tyr Asn Gly Phe Asn
            100                 105                 110

Leu Ile Leu Ala Asp Ile Glu Thr Lys Lys Met Val Tyr Val Thr Asn
        115                 120                 125

Arg Pro Lys Gly Glu Pro Ile Thr Ile Gln Glu Val Gln Pro Gly Ile
    130                 135                 140

His Val Leu Ser Asn Ala Lys Leu Asp Ser Pro Trp Pro Lys Ala Gln
145                 150                 155                 160

Arg Leu Lys Leu Asn Phe Lys Lys Met Leu Asp Val Tyr Glu Val Asn
```

```
                165                 170                 175
Asp Glu Lys Ile Cys Val Lys Asp Met Ile Glu Lys Leu Met Arg Asp
            180                 185                 190

Thr Thr Lys Ala Asp Lys Ser Lys Leu Pro Cys Ile Cys Ser Thr Asp
        195                 200                 205

Trp Glu Leu Glu Leu Ser Ser Ile Phe Val Glu Val Asp Thr Ala Leu
    210                 215                 220

Gly Cys Tyr Gly Thr Arg Ser Thr Thr Ala Leu Thr Ile Glu Val Gly
225                 230                 235                 240

Gly Glu Val Ser Phe Tyr Glu Leu Tyr Leu Glu Asn Asn Met Trp Lys
                245                 250                 255

Glu Gln Ile Val Asn Tyr Arg Ile Glu Lys Leu Gln Met Gln
            260                 265                 270

<210> SEQ ID NO 23
<211> LENGTH: 3155
<212> TYPE: DNA
<213> ORGANISM: Lycopersicon hirsutum
<220> FEATURE:
<221> NAME/KEY: misc_feature
<222> LOCATION: (1501)..(1501)
<223> OTHER INFORMATION: n is a, c, g, or t
<220> FEATURE:
<221> NAME/KEY: misc_feature
<222> LOCATION: (1510)..(1510)
<223> OTHER INFORMATION: n is a, c, g, or t
<220> FEATURE:
<221> NAME/KEY: misc_feature
<222> LOCATION: (1512)..(1512)
<223> OTHER INFORMATION: n is a, c, g, or t
<220> FEATURE:
<221> NAME/KEY: misc_feature
<222> LOCATION: (1543)..(1543)
<223> OTHER INFORMATION: n is a, c, g, or t
<220> FEATURE:
<221> NAME/KEY: misc_feature
<222> LOCATION: (1874)..(1874)
<223> OTHER INFORMATION: n is a, c, g, or t

<400> SEQUENCE: 23
tgccgtccta ttcttagaat actcaagtaa tttaacgtag tggtgaaaat ttgataaatt      60
aattatatac taattttca gtcttatttt atgtggtata tttaattgga tatgtagttt     120
aagaaataat aaaacttta aaatatttat aaatttactt ttctaaaaaa gtgaattcaa     180
ttttttctct cctcataaat gtattagagt attatcatta aaattaagtg ggactaataa     240
aggtaaaaaa taattattc ctttaaatta tttaaccata taagaaaatg tgacattctt     300
ttttagactt gactaaaata gaaataatg tcatatatat aaaatgagac gaaaaaagta     360
aatattaatt taaatttaa aactttaggg taatagctac tttgaattac ctagatttca     420
ataaaattca acatataata aaacatacta atttacaatt tttaaaataa tatgactaaa     480
agtcatatta ttcaaaaaac aatctatacc gccgtcacct agttacttta atttgtgtag     540
cttctagtac atacattttt aaactttatc tgaatttaat attttaatta tattaaacat     600
ttattaaaat ttataaaatt taaattgacg taatataatg aagagagtag tactatataa     660
accatgtgag tactaacatg atcttcatct tattcttgtt tttatttata gaaacaataa     720
aatagttata aaattaatca atcatgtgta tagtagtgtt tatttgggaa gcagatagta     780
gatattcatt agtgttatta ttgaatagag atgaatatca taataggcca acaaaggaag     840
ttcattggtg ggaagatgga gaaattgttg gtggcaaaga tgaagttggt ggtggcactt     900
ggttggcttc ttcaactaat ggtaaatggc tttcttacta atgttttgga acttcataca     960
```

```
cttcctcatg ccaaaactag aggtgaccta cctgttcgat ttttacaggt acgattaaat    1020 tcttttatata ttatacgtta atatgtttga tctttcattt tggttttgtt atacgaagga   1080
cgagacctag aggtctttaa gacaaaacat aaatatgcat catagtcata aactttcaat    1140
aaatattcaa ttttgaatat gcgctttcaa aggtattaca agttgagtac taaaggaatt   1200
gagtttatca agattaaatt ttgaatttga ttcttttgat catgattaat agtaatgtta    1260
aatcttgtcc ttattggagt atatatatga tcaataaatc aagattttaa attgtagtat   1320
aatcttaatt ttaaagaata ttaatgttgt aaaatttttag atttaacaaa cacaaaaatc  1380
atatttgtat gttataacta tagtttgtat agttgcgctc aatatgtttg ttcgcgagct   1440
gttaatatgt cactatttcg gtttacatat acaaagaga tcaattgcat aattttgttt    1500
ngcatatacn tnttaaacat gatacataat agaaatttca ttnattgtgt aatatatctt   1560
tgtataaagc aagaaagagc gaaacacaac agaaaactgg atagggaaat atttatattt   1620
tgtatagtta taagtgtata tgacggaaat atacgtaatt attttttata catgattttc   1680
tctcgctttt atgcaaacac aaacacaatt tatacatttg ttttttgtgta aagtgagagt  1740 ggcgagcgag attctataga gagagaacca atgaaaata tatgtattat atgcagtttt   1800
ctgtagtttt atacaaatac aaacacaatt tatacattta tttttgtgta tgagagaggc  1860
gagtgagatt ctcngggggag gaaaatatat gtatatatac agttttgttt cgctataaac 1920
aaacagaaca catttttatac atttgtattt gtataaaaca agagagacga gggagaaact  1980
gctcaacgag aaattcagga agagaggtga atgacaacta tttgttacga gttgcaagta   2040
aatcaaactg cgactataac atttagtttg aattaataat ttgttatttt aaacgatttt   2100
ccgtaaaatt taattgttaa ttgcagagca ataaaagccc aatggagttt gcaaagagt    2160 tggtgaatga agggaatgaa tacaatgggt ttaatttaat tttggcagat attgaaacta   2220
aaaaaatggt atatgtaaca aataggccca aaggagagcc cataacaata caagaagtcc   2280
aaccaggtat tcatgtgctg tccaatgcaa aactggactc tccttggccc aaggtaagaa  2340
ttctaatggg cttttttcga tcgatataca taaattatac aaatgatatg cttttggttg  2400
ttcatttcag gctcaaagac tgaagttaaa ttttaagaaa atgttggatg tttacgaagt  2460
gaatgacgag aaaatctgcg tcaaagatat gatagaaaaa ttgatgagag ataccactaa  2520
agctgataaa agtaaattgc cttgtatttg ttctacagac tgggagttgg aacttagctc   2580 tatttttcgtg gaagttgaca ctgcactggg taattcatac cgcgttataa ctaatatgtt  2640
tgtttgattt taacgtactc aaacgatgat aaaggttaaa gtagatatac aaacatttta  2700
aaaataattg aaatagttca ataatagaag tgtacatatc attaacatag tttgatgggt   2760 tttttttggtg gtgtgaatat gtaggggtgt tatggtacta gaagtacaac agcattgaca  2820
attgaagtgg gaggagaagt aagctttat gagttgtacc ttgagaacaa catgtggaaa   2880
gagcaaattg tcaactatcg gattgaaaaa ctccaaatgc aataaatgtt tttaatatgt   2940
tgatatatct aatgttttc atgttcatat gttgacatat ctaatgtttt catttttttt   3000
ttttaattca aataagattt tttcttcaaa aaattaaact ttttgtctttt gaatggaaat  3060 tgttattcat tgtatttgta aaatgtacta cactacttgg aagacataat gtatgtttcg   3120
ggctcctttg ttttagcaac aattttagac tttca                              3155

<210> SEQ ID NO 24
<211> LENGTH: 750
<212> TYPE: DNA
```

<213> ORGANISM: Lycopersicon hirsutum

<400> SEQUENCE: 24

```
atgtctatac cggtgttcat atggaaagcg catccgttgc atcccttcct tctcttcctc    60
aacagagatg aataccacaa tcgtccaacg aaaccattgt catggtggga agatactgat   120
atacttggtg aagggatga agttgctggt gggacttggt tggcttgtac tcgcactgga   180
agacttgctt ttcttactaa tgttcgagaa atcaattcaa attcacatac cagaagtagg   240
ggagacctcc ctcttcgatt cttaaagagt gtgaagagcc ctcgtgattt ttcagagcaa   300
ctattgatag aagcaggtga atataatggg tttaatttga tagtaactga tctttgttca   360
atgactatgc tatatataac taaccgaccg aaacacaccg gtatgtccgt cactgaggtt   420
tcacccggta ttcatgtttt atcaaatgca tcactaaact ctccatggcc taagtctcaa   480
cggctggagt gcagtttcaa gcaattattg gatgaatatg gcgaatcgga aattccaata   540
gggcatgcag ctgaaagaat atgagagacg tggctcaaga agatagtaac ccgccaggca   600
tcatattctc ccgagtgtga gtaccaattg agctccctat tgttgacac tgaaatgtgc   660
atggggcgtt tttgcccaag aagcacttct tcactggccg tgaagaagtc ttgtgacgcc   720
accttttatg agcggttcct gagaaggttt                                    750
```

<210> SEQ ID NO 25
<211> LENGTH: 250
<212> TYPE: PRT
<213> ORGANISM: Lycopersicon hirsutum

<400> SEQUENCE: 25

```
Met Ser Ile Pro Val Phe Ile Trp Lys Ala His Pro Leu His Pro Phe
1               5                   10                  15

Leu Leu Phe Leu Asn Arg Asp Glu Tyr His Asn Arg Pro Thr Lys Pro
            20                  25                  30

Leu Ser Trp Trp Glu Asp Thr Asp Ile Leu Gly Gly Arg Asp Glu Val
        35                  40                  45

Ala Gly Gly Thr Trp Leu Ala Cys Thr Arg Thr Gly Arg Leu Ala Phe
    50                  55                  60

Leu Thr Asn Val Arg Glu Ile Asn Ser Asn Ser His Thr Arg Ser Arg
65                  70                  75                  80

Gly Asp Leu Pro Leu Arg Phe Leu Lys Ser Val Lys Ser Pro Arg Asp
                85                  90                  95

Phe Ser Glu Gln Leu Leu Ile Glu Ala Gly Glu Tyr Asn Gly Phe Asn
            100                 105                 110

Leu Ile Val Thr Asp Leu Cys Ser Met Thr Met Leu Tyr Ile Thr Asn
        115                 120                 125

Arg Pro Lys His Thr Gly Met Ser Val Thr Glu Val Ser Pro Gly Ile
    130                 135                 140

His Val Leu Ser Asn Ala Ser Leu Asn Ser Pro Trp Pro Lys Ser Gln
145                 150                 155                 160

Arg Leu Glu Cys Ser Phe Lys Gln Leu Leu Asp Glu Tyr Gly Glu Ser
                165                 170                 175

Glu Ile Pro Ile Gly His Ala Ala Glu Arg Ile Met Arg Asp Val Ala
            180                 185                 190

Gln Glu Asp Ser Asn Pro Pro Gly Ile Ile Ser Pro Glu Cys Glu Tyr
        195                 200                 205

Gln Leu Ser Ser Leu Phe Val Asp Thr Glu Met Cys Met Gly Arg Phe
    210                 215                 220
```

```
Cys Pro Arg Ser Thr Ser Ser Leu Ala Val Lys Lys Ser Cys Asp Ala
225                 230                 235                 240

Thr Phe Tyr Glu Arg Phe Leu Arg Arg Phe
                245                 250

<210> SEQ ID NO 26
<211> LENGTH: 762
<212> TYPE: DNA
<213> ORGANISM: Arabidopsis thaliana

<400> SEQUENCE: 26
atgaagatca acagggcg acagaggcgc tgcgtttggt gggaagacgg agagacggtg      60
ggaggaagag accttgttgg cggcgggacg tggctgggct gcacgaggca tggccgtctg     120
gctttcctca ccaatttcaa ggaagcctcc tccttccctg ctgctaaatc ccgtggagat     180
ctgcctcttc gttacttgca gagcgaaaag agtccggccg agtttgccga ggagatccaa     240
gacgaaattt cactctacaa tggctttaac ctggttgtcg ctcatgtctt gtccaaatcc     300
atgatttaca ttaccaaccg accaccccac ggtgacaagc tcgtgacgca agtctctccc     360
gggatccatg tcctttccaa cgccaacctc gactccccct tggcccaagt gtctgaggctg    420 agggagggtt ccaacagct tctggctgag aacgggagcg gtgaattccc ggtgaagacc     480
atggtggagg aggtgatgac caatactgtc aaggacgaag aaaccgagct acctcacgtt     540
ttcacaccag agacggaata ccatctcagc tccatcttcg tcgacatgca gagaccaact     600
gggcgttatg ggaccagaag catctctgcg atcatcgtca gtcccatgg agatggtggt     660 ggtgatggtg agatttgctt ctacgagagg catcttgaag aaggcgattc atggaaggaa     720
cacactcaac agtttgtaat aatacaaaac caaagcattt ga                       762

<210> SEQ ID NO 27
<211> LENGTH: 253
<212> TYPE: PRT
<213> ORGANISM: Arabidopsis thaliana

<400> SEQUENCE: 27

Met Lys Ile Thr Thr Gly Arg Gln Arg Arg Cys Val Trp Trp Glu Asp
1               5                   10                  15

Gly Glu Thr Val Gly Gly Arg Asp Leu Val Gly Gly Gly Thr Trp Leu
                20                  25                  30

Gly Cys Thr Arg His Gly Arg Leu Ala Phe Leu Thr Asn Phe Lys Glu
            35                  40                  45

Ala Ser Ser Phe Pro Ala Ala Lys Ser Arg Gly Asp Leu Pro Leu Arg
        50                  55                  60

Tyr Leu Gln Ser Glu Lys Ser Pro Ala Glu Phe Ala Glu Glu Ile Gln
65                  70                  75                  80

Asp Glu Ile Ser Leu Tyr Asn Gly Phe Asn Leu Val Val Ala His Val
                85                  90                  95

Leu Ser Lys Ser Met Ile Tyr Ile Thr Asn Arg Pro Pro His Gly Asp
            100                 105                 110

Lys Leu Val Thr Gln Val Ser Pro Gly Ile His Val Leu Ser Asn Ala
        115                 120                 125

Asn Leu Asp Ser Pro Trp Pro Lys Cys Leu Arg Leu Arg Glu Gly Phe
    130                 135                 140

Gln Gln Leu Leu Ala Glu Asn Gly Ser Gly Glu Phe Pro Val Lys Thr
145                 150                 155                 160
```

Met Val Glu Glu Val Met Thr Asn Thr Val Lys Asp Glu Glu Thr Glu
            165                 170                 175

Leu Pro His Val Phe Thr Pro Gly Thr Glu Tyr His Leu Ser Ser Ile
        180                 185                 190

Phe Val Asp Met Gln Arg Pro Thr Gly Arg Tyr Gly Thr Arg Ser Ile
            195                 200                 205

Ser Ala Ile Ile Val Lys Ser His Gly Asp Gly Gly Asp Gly Glu
        210                 215                 220

Ile Cys Phe Tyr Glu Arg His Leu Glu Gly Asp Ser Trp Lys Glu
225                 230                 235                 240

His Thr Gln Gln Phe Val Ile Ile Gln Asn Gln Ser Ile
                245                 250

<210> SEQ ID NO 28
<211> LENGTH: 801
<212> TYPE: DNA
<213> ORGANISM: Arabidopsis thaliana

<400> SEQUENCE: 28 atgggagag ggagaaaaca cactgacgct gctgcagaac agagagaact ggcaattaag      60
gcaaacattg ttgatgaacc ttttctgta tcggcgattg ataggtcaat aagaaaggcg    120
gaatgggtta aaactgaaac tgaccagata ttaagtggtc gttgcccaga gaccgatggg    180
acgtggttag gtatttctac tcgaggccga gtcgcttttc ttgtggaggc agggactatt    240
aacagagaca gattcaacgg cgccgagagt cgtactcttg agttcttaga gagcaacgag    300
agtccagagg acttttgcaaa gtcatcggct gcagattaca tacgtaacaa gaacacagcc    360
gccttcatc taattgtggc cgacatagct tcaaactcaa tgctttatat ctccaaaccg    420
cgtttctctg actatggcat tgtctataca gagcctgttg gtcctggtgt tcacacacta    480
tcttcagctg gactcgattc cgacgttgga tacagggact tacgtatgag acactctttt    540
tgtgagatga ttaacagaga acgactacca ccaataaggg acattgctga gattatgtat    600
gatccagtca aagcttacga aagcgtgcta ctgagctcta ttttttttcgt cgacatgaag    660
attggatacg aacactatgg aacaagaatt acgacagcat ggttgtgaa acgcaccaag    720
gaagtgttgt tctttgagag gtacagggag atatttaatg atgattggga cgaccacgac    780
ttcgcgttca ccatcatcta g                                              801

<210> SEQ ID NO 29
<211> LENGTH: 266
<212> TYPE: PRT
<213> ORGANISM: Arabidopsis thaliana

<400> SEQUENCE: 29

Met Gly Arg Gly Arg Lys His Thr Asp Ala Ala Glu Gln Arg Glu
1               5                   10                  15

Leu Ala Ile Lys Ala Asn Ile Val Asp Glu Pro Phe Ser Val Ser Ala
            20                  25                  30

Ile Asp Arg Ser Ile Arg Lys Ala Glu Trp Val Lys Thr Glu Thr Asp
        35                  40                  45

Gln Ile Leu Ser Gly Arg Cys Pro Glu Thr Asp Gly Trp Leu Gly
    50                  55                  60

Ile Ser Thr Arg Gly Arg Val Ala Phe Leu Val Glu Ala Gly Thr Ile
65                  70                  75                  80

Asn Arg Asp Arg Phe Asn Gly Ala Glu Ser Arg Thr Leu Glu Phe Leu
                85                  90                  95

```
Glu Ser Asn Glu Ser Pro Glu Asp Phe Ala Lys Ser Ser Ala Ala Asp
                100                 105                 110

Tyr Ile Arg Asn Lys Asn Thr Ala Ala Phe His Leu Ile Val Ala Asp
            115                 120                 125

Ile Ala Ser Asn Ser Met Leu Tyr Ile Ser Lys Pro Arg Phe Ser Asp
        130                 135                 140

Tyr Gly Ile Val Tyr Thr Glu Pro Val Gly Pro Val His Thr Leu
145                 150                 155                 160

Ser Ser Ala Gly Leu Asp Ser Asp Val Gly Tyr Arg Asp Leu Arg Met
                165                 170                 175

Arg His Ser Phe Cys Glu Met Ile Asn Arg Glu Arg Leu Pro Pro Ile
            180                 185                 190

Arg Asp Ile Ala Glu Ile Met Tyr Asp Pro Val Lys Ala Tyr Glu Ser
        195                 200                 205

Val Leu Leu Ser Ser Ile Phe Phe Val Asp Met Lys Ile Gly Tyr Glu
    210                 215                 220

His Tyr Gly Thr Arg Ile Thr Thr Ala Leu Val Val Lys Arg Thr Lys
225                 230                 235                 240

Glu Val Leu Phe Phe Glu Arg Tyr Arg Glu Ile Phe Asn Asp Asp Trp
                245                 250                 255

Asp Asp His Asp Phe Ala Phe Thr Ile Ile
            260                 265

<210> SEQ ID NO 30
<211> LENGTH: 1122
<212> TYPE: DNA
<213> ORGANISM: Arabidopsis thaliana

<400> SEQUENCE: 30
atgcctggag aatcgaatat catcgagtgg ccagcaagta gagtcagggt cataagtggg      60
gcatcttgga gtcgaaacgg tcagattttg agtggtcggt gcaaagctaa caacggaacc     120
tggtttggta ttactaaagg tggccgagtc gcttttctcg tgaatacatc gttgttgttg     180
gaccgtgtta agtcatacag cggctcggag ttgtatcccg ttcgtttctt ggagggcaac     240
atgagtccag agcagtttgc caacgaagtg aaagtgcatg aaaaggagac taatgaaagg     300
catgcctata gtcttgtcgt tgcagacatg acttcgagtt caatggttca tatcctgaaa     360
ccctcggata ctaagtctga tgtcgtgata gagactgttc cgtttggtgt gcatacactt     420
tcttcttacg aaggtctcga ttctacagat tctgccaggg atttactcct gagacgcttg     480
tttacccaga tggttggtaa tttgggaaac gttcaacaac gacagatgga ggagattgct     540
gggaggttta tgtatgatgc tcaagcagga agagacgcgg tgttttacca agtagagat      600 gagcatccta atggaaaact tggaacgcaa cgctttggaa caacaagtac gacagcattg     660
gttgtgaaac gcactagaga agtgatgctc tttgagaagt acatggagca gaatggtgca     720
tggaacacga caacttcgc tttcaacatc caaaacagc aaaagctata tccaaatttg      780
gataaagaag ctcttaagcg cgttgggggta tttgcgttgg aagaagttaa caaccatgag     840
catgatattc accctgacct gatgcccagt ttcttcgagg atgatatgct gaaagtaaaa     900
tttaatgaga tgattgctag acatgcaaaa ctgccgccaa ttaagaacat tgttgaggat     960
cttatgatga gtctccatt tttttatcgac agtgtcgatg gtgctggcaa gaaggtgagg    1020
tatcgaacag tacgtacatt gggaatggac ataaaagcca acagaccaca agggcggttc    1080
tatgagaggc atttgaatga taatggtgaa tgggtaggct ag                       1122
```

```
<210> SEQ ID NO 31
<211> LENGTH: 373
<212> TYPE: PRT
<213> ORGANISM: Arabidopsis thaliana

<400> SEQUENCE: 31

Met Pro Gly Glu Ser Asn Ile Ile Glu Trp Pro Ala Ser Arg Val Arg
1               5                   10                  15

Val Ile Ser Gly Ala Ser Trp Ser Arg Asn Gly Gln Ile Leu Ser Gly
                20                  25                  30

Arg Cys Lys Ala Asn Asn Gly Thr Trp Phe Gly Ile Thr Lys Gly Gly
            35                  40                  45

Arg Val Ala Phe Leu Val Asn Thr Ser Leu Leu Asp Arg Val Lys
        50                  55                  60

Ser Tyr Ser Gly Ser Glu Leu Tyr Pro Val Arg Phe Leu Glu Gly Asn
65                  70                  75                  80

Met Ser Pro Glu Gln Phe Ala Asn Glu Val Lys Val His Glu Lys Glu
                85                  90                  95

Thr Asn Glu Arg His Ala Tyr Ser Leu Val Val Ala Asp Met Thr Ser
            100                 105                 110

Ser Ser Met Val His Ile Leu Lys Pro Ser Asp Thr Lys Ser Asp Val
        115                 120                 125

Val Ile Glu Thr Val Pro Phe Gly Val His Thr Leu Ser Ser Tyr Glu
    130                 135                 140

Gly Leu Asp Ser Thr Asp Ser Ala Arg Asp Leu Leu Leu Arg Arg Leu
145                 150                 155                 160

Phe Thr Gln Met Val Gly Asn Leu Gly Asn Val Gln Gln Arg Gln Met
                165                 170                 175

Glu Glu Ile Ala Gly Arg Phe Met Tyr Asp Ala Gln Ala Gly Arg Asp
            180                 185                 190

Ala Val Phe Tyr His Ser Arg Asp Glu His Pro Asn Gly Lys Leu Gly
        195                 200                 205

Thr Gln Arg Phe Gly Thr Thr Ser Thr Thr Ala Leu Val Val Lys Arg
    210                 215                 220

Thr Arg Glu Val Met Leu Phe Glu Lys Tyr Met Glu Gln Asn Gly Ala
225                 230                 235                 240

Trp Asn Thr Asn Asn Phe Ala Phe Asn Ile Gln Lys Gln Gln Lys Leu
                245                 250                 255

Tyr Pro Asn Leu Asp Lys Glu Ala Leu Lys Arg Val Gly Val Phe Ala
            260                 265                 270

Leu Glu Glu Val Asn Asn His Glu His Asp Ile His Pro Asp Leu Met
        275                 280                 285

Pro Ser Phe Phe Glu Asp Asp Met Leu Lys Val Lys Phe Asn Glu Met
    290                 295                 300

Ile Ala Arg His Ala Lys Leu Pro Pro Ile Lys Asn Ile Val Glu Asp
305                 310                 315                 320

Leu Met Met Lys Ser Pro Phe Phe Ile Asp Ser Val Asp Gly Ala Gly
                325                 330                 335

Lys Lys Val Arg Tyr Arg Thr Val Arg Thr Leu Gly Met Asp Ile Lys
            340                 345                 350

Ala Asn Arg Pro Gln Gly Arg Phe Tyr Glu Arg His Leu Asn Asp Asn
        355                 360                 365

Gly Glu Trp Val Gly
```

<210> SEQ ID NO 32
<211> LENGTH: 713
<212> TYPE: DNA
<213> ORGANISM: Vitis vinifera

<400> SEQUENCE: 32

```
ggtcgcactg tatatattca acggagagga gcagtgacgg cgtttggagg ccgagaaagt    60
aagagatttc agtttctgag gcgggaaagt acggaagcat gtgtatagca gtattcttat   120
ggcaagctca cccgatttat cctttccttc tgttgctcaa cagagacgaa tatcataatc   180
ggcctactga ggctctggca tggtggcaag gtggggagat actgggcggg cgagatgggc   240
tcgccggtgg gacatggttg gcttgtagca gagatgggag gttggctttt cttacaaatg   300
tgcgagaagt tcacccaatc cccgaagcca agagcagagg agacctaatt gttcggttct   360
tggagagcaa gaagaatccc atggaatttg cagaggaagt tgtgaaggag cagataagt   420
ataatgggtt taacttgata atggctgatc tttgttccaa aactatgatc tatataacca   480
acagaccaag agaagctaat gtttctgttg tcgaggtttc acctggtatt catgtgctgt   540
caaatgcaag tttggactca ccttggccta aggtacgaag actaggtcat aatttcaaag   600
agctcttgga taaatatggt gaaggtgaga tccccacaga ggagatggtt gagaaattaa   660
tgaagaaaca caatcaaaga cgatgaaatc gtgctgcctc gcatctatcc tcc           713
```

<210> SEQ ID NO 33
<211> LENGTH: 207
<212> TYPE: PRT
<213> ORGANISM: Vitis vinifera

<400> SEQUENCE: 33

```
Glu Ile Ser Val Ser Glu Ala Gly Lys Tyr Gly Ser Met Cys Ile Ala
1               5                   10                  15

Val Phe Leu Trp Gln Ala His Pro Ile Tyr Pro Phe Leu Leu Leu Leu
            20                  25                  30

Asn Arg Asp Glu Tyr His Asn Arg Pro Thr Glu Ala Leu Ala Trp Trp
        35                  40                  45

Gln Gly Gly Glu Ile Leu Gly Gly Arg Asp Gly Leu Ala Gly Gly Thr
    50                  55                  60

Trp Leu Ala Cys Ser Arg Asp Gly Arg Leu Ala Phe Leu Thr Asn Val
65                  70                  75                  80

Arg Glu Val His Pro Ile Pro Glu Ala Lys Ser Arg Gly Asp Leu Ile
                85                  90                  95

Val Arg Phe Leu Glu Ser Lys Lys Asn Pro Met Glu Phe Ala Glu Glu
            100                 105                 110

Val Val Lys Glu Ala Asp Lys Tyr Asn Gly Phe Asn Leu Ile Met Ala
        115                 120                 125

Asp Leu Cys Ser Lys Thr Met Ile Tyr Ile Thr Asn Arg Pro Arg Glu
    130                 135                 140

Ala Asn Val Ser Val Val Glu Val Ser Pro Gly Ile His Val Leu Ser
145                 150                 155                 160

Asn Ala Ser Leu Asp Ser Pro Trp Pro Lys Val Arg Arg Leu Gly His
                165                 170                 175

Asn Phe Lys Glu Leu Leu Asp Lys Tyr Gly Glu Gly Glu Ile Pro Thr
            180                 185                 190

Glu Glu Met Val Glu Lys Leu Met Lys Lys His Asn Gln Arg Arg
```

<210> SEQ ID NO 34
<211> LENGTH: 1068
<212> TYPE: DNA
<213> ORGANISM: Zea mays

<400> SEQUENCE: 34

```
gatcagctaa atagctgca aaacaagcga gttacttaca accaaacaga agggtagaaa      60
ccacctgaag ccatgtgcat tgctgcatgg atttggcagg ctcaccctgt gcaccaactc     120
ctcctgcttc tcaacagaga tgagttccac agcaggccta caaaagcagt aggatggtgg     180
ggtgaaggct caagaagat ccttggtggc agggatgtgc ttggtggagg aacatggatg      240
gggtgcacca aggatggaag gcttgccttc ctgaccaatg tgcttgaacc agatgccatg     300
cccggtgcac ggactagggg agatctgcct ctcaaattcc tgcagagcaa caagagccca     360
ctcgaagttg caactgaagt ggcagaagaa gctgatgaat acaatggctt caacctcata     420
ctagctgatc taacaacaaa tatcatggtt tatgtgtcaa accggcctaa gggtcagcct     480
gcaacaattc aactcgtgtc accaggactc catgtgctgt ccaatgcaag gctagatagc     540
ccttggcaga aggcaattct cctcggtaaa aacttcaggg agcttcttag ggagcatggt     600
gctgatgagg ttgaagtgaa ggatatagtt gagaggctaa tgactgacac cacaaaggct     660
gacaaagata gactgccaaa cactggttgt gatcccaact gggagcatgg tctgagctcc     720
atcttcattg aggtgcaaac tgaccaaggg ccctatggga cacggagcac agccgtttta    780
tcagtgaact atgatggcga agctagcttg tacgagaagt atcttgagag tggtatatgg    840
aaggatcaca cagtgagtta ccagatagag tagtaggcat tgcacaggaa aagttggcga    900
cctcaaataa atagaaatat gaagcagaca caattgtgaa tttcattatt tccctgatct    960
ctagtcatct tcgtgattat ctaagatcct accataatgc caattacatt attcactgta   1020
agcagatttt tcacttgacg ataaaatgtc aaccaaaact ttggtttt                 1068
```

<210> SEQ ID NO 35
<211> LENGTH: 271
<212> TYPE: PRT
<213> ORGANISM: Zea mays

<400> SEQUENCE: 35

Lys Pro Pro Glu Ala Met Cys Ile Ala Ala Trp Ile Trp Gln Ala His
1               5                   10                  15

Pro Val His Gln Leu Leu Leu Leu Asn Arg Asp Glu Phe His Ser
            20                  25                  30

Arg Pro Thr Lys Ala Val Gly Trp Trp Gly Glu Gly Ser Lys Lys Ile
        35                  40                  45

Leu Gly Gly Arg Asp Val Leu Gly Gly Gly Thr Trp Met Gly Cys Thr
    50                  55                  60

Lys Asp Gly Arg Leu Ala Phe Leu Thr Asn Val Leu Glu Pro Asp Ala
65                  70                  75                  80

Met Pro Gly Ala Arg Thr Arg Gly Asp Leu Pro Leu Lys Phe Leu Gln
                85                  90                  95

Ser Asn Lys Ser Pro Leu Glu Val Ala Thr Glu Val Ala Glu Glu Ala
            100                 105                 110

Asp Glu Tyr Asn Gly Phe Asn Leu Ile Leu Ala Asp Leu Thr Thr Asn
        115                 120                 125

Ile Met Val Tyr Val Ser Asn Arg Pro Lys Gly Gln Pro Ala Thr Ile

```
                130                 135                 140
Gln Leu Val Ser Pro Gly Leu His Val Leu Ser Asn Ala Arg Leu Asp
145                 150                 155                 160

Ser Pro Trp Gln Lys Ala Ile Leu Leu Gly Lys Asn Phe Arg Glu Leu
                165                 170                 175

Leu Arg Glu His Gly Ala Asp Glu Val Glu Val Lys Asp Ile Val Glu
                180                 185                 190

Arg Leu Met Thr Asp Thr Thr Lys Ala Asp Lys Asp Arg Leu Pro Asn
                195                 200                 205

Thr Gly Cys Asp Pro Asn Trp Glu His Gly Leu Ser Ser Ile Phe Ile
                210                 215                 220

Glu Val Gln Thr Asp Gln Gly Pro Tyr Gly Thr Arg Ser Thr Ala Val
225                 230                 235                 240

Leu Ser Val Asn Tyr Asp Gly Glu Ala Ser Leu Tyr Glu Lys Tyr Leu
                245                 250                 255

Glu Ser Gly Ile Trp Lys Asp His Thr Val Ser Tyr Gln Ile Glu
                260                 265                 270

<210> SEQ ID NO 36
<211> LENGTH: 1152
<212> TYPE: DNA
<213> ORGANISM: Hordeum vulgare

<400> SEQUENCE: 36
cacacacaca caaggcgcac ggttgcaaaa caagggagtt atttttagaa gcagggagta      60
aggaaccacc tgaagccatg tgtatcgctg catggcattt gcaggctca cccacagcat     120
cagctcctgc tgctgctcaa cagagatgag ttccatagca ggcctacaaa ggcagtagga     180
tggtggggcg agggctcaat gaagattctt ggtggcaggg atgtactcgg tggaggaaca     240
tggatgggga gcaccaaaga tggcaggctt gccttcctga ccaatgtgct cgagcctgat     300
gcaatgcccg cgcacgcac tagggagac ctgcccctca ggttcctgca gggaaacaag     360
agcccactgg aggttgcgac tgaagtggca aaagaagctg atgagtacaa tggcttcaac     420
cttatactag ctgatctaac caggaatgtc atggtctacg tgtcaaaccg gccaaagggg     480
cagcctgcga caattcagct cgtctcacca ggactccatg tgttgtccaa tgcaaggctt     540
gatagccctt ggcagaaggc aattcgcctt ggtaaaaact tcaggagtt tataaggaag     600
catggtgatg atgaagttga agcgaaggat atagctgaca gactaatgac tgacacgacg     660
agggctgata agataggct gccaaacacc ggttgtgatc ccacctggga gcacggtctg     720
agctccatct tcatcgaggt gcaaactgac gaagggctct atgggacaag gagcacagca     780
gttctttcag tgaactatga tggagaagct agcttatatg aaaagtacct cgagagtggt     840
atatggaaga accacacagt gcattaccag atagagtagc caatgcggac ctaaaggcgg     900
gagcccaaaa taggaagaaa gaatgaatag ctacaattgt gcatgctgtt atttccacag     960
ttgcgctta agatcatata atgatctcta gttatggcga ttaaattatt tactgtatgc    1020
agatttatca attcagagag agatcattca aattgttgaa tatatataca taataataat    1080
aatatgatat gatatgtata tttacagact tcatgttgcc acctttgtct atgaacatac    1140
atgctttact ac                                                         1152

<210> SEQ ID NO 37
<211> LENGTH: 291
<212> TYPE: PRT
<213> ORGANISM: Hordeum vulgare
```

<400> SEQUENCE: 37

Lys Gln Gly Val Arg Asn His Leu Lys Pro Cys Val Ser Leu His Gly
1               5                   10                  15

Ile Trp Gln Ala His Pro Gln His Gln Leu Leu Leu Leu Leu Asn Arg
            20                  25                  30

Asp Glu Phe His Ser Arg Pro Thr Lys Ala Val Gly Trp Trp Gly Glu
        35                  40                  45

Gly Ser Met Lys Ile Leu Gly Gly Arg Asp Val Leu Gly Gly Gly Thr
    50                  55                  60

Trp Met Gly Ser Thr Lys Asp Gly Arg Leu Ala Phe Leu Thr Asn Val
65                  70                  75                  80

Leu Glu Pro Asp Ala Met Pro Gly Ala Arg Thr Arg Gly Asp Leu Pro
                85                  90                  95

Leu Arg Phe Leu Gln Gly Asn Lys Ser Pro Leu Glu Val Ala Thr Glu
            100                 105                 110

Val Ala Lys Glu Ala Asp Glu Tyr Asn Gly Phe Asn Leu Ile Leu Ala
        115                 120                 125

Asp Leu Thr Arg Asn Val Met Val Tyr Val Ser Asn Arg Pro Lys Gly
    130                 135                 140

Gln Pro Ala Thr Ile Gln Leu Val Ser Pro Gly Leu His Val Leu Ser
145                 150                 155                 160

Asn Ala Arg Leu Asp Ser Pro Trp Gln Lys Ala Ile Arg Leu Gly Lys
                165                 170                 175

Asn Phe Arg Glu Phe Ile Arg Lys His Gly Asp Asp Glu Val Glu Ala
            180                 185                 190

Lys Asp Ile Ala Asp Arg Leu Met Thr Asp Thr Arg Ala Asp Lys
        195                 200                 205

Asp Arg Leu Pro Asn Thr Gly Cys Asp Pro Thr Trp Glu His Gly Leu
    210                 215                 220

Ser Ser Ile Phe Ile Glu Val Gln Thr Asp Gly Leu Tyr Gly Thr
225                 230                 235                 240

Arg Ser Thr Ala Val Leu Ser Val Asn Tyr Asp Gly Glu Ala Ser Leu
                245                 250                 255

Tyr Glu Lys Tyr Leu Glu Ser Gly Ile Trp Lys Asn His Thr Val His
            260                 265                 270

Tyr Gln Ile Glu Pro Met Arg Thr Arg Glu Pro Lys Ile Gly Arg
        275                 280                 285

Lys Asn Glu
    290

<210> SEQ ID NO 38
<211> LENGTH: 801
<212> TYPE: DNA
<213> ORGANISM: Oryza sativa

<400> SEQUENCE: 38

```
atgtgtatag ctgcatgggt ttggcaagct cacccacagc accagctcct cctgctgctc      60
aaccgggatg agttccatag caggccaacc aaggcagtag gatggtgggg ggagggctcg     120
aagaagattc ttggtggtag agatgttctt ggtggaggga catggatggg ttgcacaaag     180
gatggcaggc tcgccttcct caccaatgtg ctcgagccgg acgccatgcc gggggcgcgc     240 acaagggag atctcccccct caggttcctg cagagcaaca agagcccact tgaagttgca     300
actgaggtgg caaagaagc tgacgagtac aacggcttca accttgtact ggctgatctg     360
```

-continued

```
accacaaacg tcatggttta tgtgtcaaat cggccaaagg ggcagcctgc aacgatccaa      420
cttgtctcac cagggctcca tgtgttgtcc aatgcaaggc tagacagccc ttggcagaag      480
gcgattcgcc tcggtaagaa cttcagggag catcttagga agcatggtga tgatgaggtt      540
gaagccaagg acatagttga gaggctaatg actgacacca caaaggctga caaagatagg      600
ctgccaaaca ctggctgtga tccaaactgg gagcacggcc tgagctccat tttcattgag      660
gtgcagactg accagggact ctacgggaca cggagcacgg ccgttctatc agtgaactac      720
gacggtgaag ctagcttgta cgagaaatac ctggagagtg gtatatggaa ggatcacacg      780
gtgcattacc agatagagta g                                                801
```

<210> SEQ ID NO 39
<211> LENGTH: 266
<212> TYPE: PRT
<213> ORGANISM: Oryza sativa

<400> SEQUENCE: 39

```
Met Cys Ile Ala Ala Trp Val Trp Gln Ala His Pro Gln His Gln Leu
1               5                   10                  15

Leu Leu Leu Asn Arg Asp Glu Phe His Ser Arg Pro Thr Lys Ala
            20                  25                  30

Val Gly Trp Trp Gly Glu Gly Ser Lys Lys Ile Leu Gly Gly Arg Asp
        35                  40                  45

Val Leu Gly Gly Gly Thr Trp Met Gly Cys Thr Lys Asp Gly Arg Leu
    50                  55                  60

Ala Phe Leu Thr Asn Val Leu Glu Pro Asp Ala Met Pro Gly Ala Arg
65                  70                  75                  80

Thr Arg Gly Asp Leu Pro Leu Arg Phe Leu Gln Ser Asn Lys Ser Pro
                85                  90                  95

Leu Glu Val Ala Thr Glu Val Ala Lys Glu Ala Asp Glu Tyr Asn Gly
            100                 105                 110

Phe Asn Leu Val Leu Ala Asp Leu Thr Thr Asn Val Met Val Tyr Val
        115                 120                 125

Ser Asn Arg Pro Lys Gly Gln Pro Ala Thr Ile Gln Leu Val Ser Pro
    130                 135                 140

Gly Leu His Val Leu Ser Asn Ala Arg Leu Asp Ser Pro Trp Gln Lys
145                 150                 155                 160

Ala Ile Arg Leu Gly Lys Asn Phe Arg Glu His Leu Arg Lys His Gly
                165                 170                 175

Asp Asp Glu Val Glu Ala Lys Asp Ile Val Glu Arg Leu Met Thr Asp
            180                 185                 190

Thr Thr Lys Ala Asp Lys Asp Arg Leu Pro Asn Thr Gly Cys Asp Pro
        195                 200                 205

Asn Trp Glu His Gly Leu Ser Ser Ile Phe Ile Glu Val Gln Thr Asp
    210                 215                 220

Gln Gly Leu Tyr Gly Thr Arg Ser Thr Ala Val Leu Ser Val Asn Tyr
225                 230                 235                 240

Asp Gly Glu Ala Ser Leu Tyr Glu Lys Tyr Leu Glu Ser Gly Ile Trp
                245                 250                 255

Lys Asp His Thr Val His Tyr Gln Ile Glu
            260                 265
```

<210> SEQ ID NO 40
<211> LENGTH: 707

```
<212> TYPE: DNA
<213> ORGANISM: Medicago truncatula
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t

<400> SEQUENCE: 40
ttgtacttag ttatagtatt attgaagcta gccaactcaa aatttgtgaa caatgtgtat      60
agctttgttt ctttggcaat ctcatccacc tttatccttt tcttcttttg aataatagag     120
atgaatatca caataggcct acaaagaaag tgtcatggtg ggaagaatgt gatatagtgg     180
gaggaaggga tgaaataggga ggagggacat ggttggcttg ttcttcacaa ggaaaagtgg    240
cttttcttac caatgttttg gagcttcata cttgccctga ggccaaaact cgtggagacc     300 taccctcat gtttctcaag agcagcaaga atcccaaaga atttgcagaa agcttaaaaa      360
gagaagctca atattacaat ggattcaatt tagtcattgc tgatattaat tccaaatcca    420
tggtatacat atcaaataga cccaagggac agccaattac tgtccaagag gttcctcctg    480
gtctacatgt actttcaaat gctaagttaa attcaccatg gcataaggct cagcgccttc    540
aatttagatt caaagagcat cttgctaaaa atggggaagg tgagatacat gtaaaggaag    600
taattaaaaa gctaatgaag gacaaaatta aagcagacaa aagcatgcta cctaatatat   660
gctcacttga ttggggaatt caatcttanc tncattttg ttgaaga                  707

<210> SEQ ID NO 41
<211> LENGTH: 213
<212> TYPE: PRT
<213> ORGANISM: Medicago truncatula
<220> FEATURE:
<221> NAME/KEY: misc_feature
<222> LOCATION: (209)..(210)
<223> OTHER INFORMATION: Xaa can be any naturally occurring amino acid

<400> SEQUENCE: 41

Leu Cys Phe Phe Gly Asn Leu Ile His Leu Tyr Pro Phe Leu Leu Leu
1               5                   10                  15

Asn Asn Arg Asp Glu Tyr His Asn Arg Pro Thr Lys Lys Val Ser Trp
            20                  25                  30

Trp Glu Glu Cys Asp Ile Val Gly Gly Arg Asp Glu Ile Gly Gly Gly
        35                  40                  45

Thr Trp Leu Ala Cys Ser Ser Gln Gly Lys Val Ala Phe Leu Thr Asn
    50                  55                  60

Val Leu Glu Leu His Thr Cys Pro Glu Ala Lys Thr Arg Gly Asp Leu
65                  70                  75                  80

Pro Leu Met Phe Leu Lys Ser Ser Lys Asn Pro Lys Glu Phe Ala Glu
                85                  90                  95

Ser Leu Lys Arg Glu Ala Gln Tyr Tyr Asn Gly Phe Asn Leu Val Ile
            100                 105                 110

Ala Asp Ile Asn Ser Lys Ser Met Val Tyr Ile Ser Asn Arg Pro Lys
        115                 120                 125

Gly Gln Pro Ile Thr Val Gln Glu Val Pro Pro Gly Leu His Val Leu
    130                 135                 140

Ser Asn Ala Lys Leu Asn Ser Pro Trp His Lys Ala Gln Arg Leu Gln
145                 150                 155                 160
```

Phe Arg Phe Lys Glu His Leu Ala Lys Asn Gly Glu Gly Glu Ile His
            165                 170                 175

Val Lys Glu Val Ile Lys Lys Leu Met Lys Asp Lys Ile Lys Ala Asp
        180                 185                 190

Lys Ser Met Leu Pro Asn Ile Cys Ser Leu Asp Trp Gly Ile Gln Ser
    195                 200                 205

Xaa Xaa His Phe Cys
    210

<210> SEQ ID NO 42
<211> LENGTH: 627
<212> TYPE: DNA
<213> ORGANISM: Solanum tuberosum

<400> SEQUENCE: 42

```
gatatggaaa gcgcatccgc tgtatccctt cctcctattc ctcaacagag atgaatacca    60
caatcgtgat atacttggtg aagggatga agttgctggt gggacttggt tggcttgtac   120
tcgcaccgga agacttgctt ccttactaa tgttcgagaa atcaattcaa attcacatac   180
caaaagtagg ggagacttc ctcttcgatt cttgaagagt gtaaagagcc ctcatgattt   240
ttcagagcaa cttttgaaag aagcaggcga atataatggg tttaacttga tagtagctga   300
tctttgttca atgactatgc ttgatataac caaccgacca aaacacaccg gtatgtccgg   360
cactgaagtt tcacccggta ttcacgtttt atcaaatgca acactagact ctccatggcc   420
taagtctcaa cggctggagt acagtttcaa gcaattattg gatgaatatg cgaatctga   480
aattccaata gggcagacag ctgaaagaat aatgagagac ttggctaaag aagatagcaa   540
cctgccaggc atctattccc ctgagtgtga gtaccagttg agctccatat tcgttgacac   600
tgaaatgtcc atggggcgtt ttggcac                                       627
```

<210> SEQ ID NO 43
<211> LENGTH: 208
<212> TYPE: PRT
<213> ORGANISM: Solanum tuberosum

<400> SEQUENCE: 43

Ile Trp Lys Ala His Pro Leu Tyr Pro Phe Leu Leu Phe Leu Asn Arg
1               5                   10                  15

Asp Glu Tyr His Asn Arg Asp Ile Leu Gly Gly Arg Asp Glu Val Ala
            20                  25                  30

Gly Gly Thr Trp Leu Ala Cys Thr Arg Thr Gly Arg Leu Ala Phe Leu
        35                  40                  45

Thr Asn Val Arg Glu Ile Asn Ser Asn Ser His Thr Lys Ser Arg Gly
50                  55                  60

Asp Leu Pro Leu Arg Phe Leu Lys Ser Val Lys Ser Pro His Asp Phe
65                  70                  75                  80

Ser Glu Gln Leu Leu Lys Glu Ala Gly Glu Tyr Asn Gly Phe Asn Leu
                85                  90                  95

Ile Val Ala Asp Leu Cys Ser Met Thr Met Leu Asp Ile Thr Asn Arg
            100                 105                 110

Pro Lys His Thr Gly Met Ser Gly Thr Glu Val Ser Pro Gly Ile His
        115                 120                 125

Val Leu Ser Asn Ala Thr Leu Asp Ser Pro Trp Pro Lys Ser Gln Arg
    130                 135                 140

Leu Glu Tyr Ser Phe Lys Gln Leu Leu Asp Glu Tyr Gly Glu Ser Glu
145                 150                 155                 160

```
Ile Pro Ile Gly Gln Thr Ala Glu Arg Ile Met Arg Asp Leu Ala Lys
                165                 170                 175
Glu Asp Ser Asn Leu Pro Gly Ile Tyr Ser Pro Glu Cys Glu Tyr Gln
            180                 185                 190
Leu Ser Ser Ile Phe Val Asp Thr Glu Met Ser Met Gly Arg Phe Gly
        195                 200                 205

<210> SEQ ID NO 44
<211> LENGTH: 423
<212> TYPE: DNA
<213> ORGANISM: Glycine max

<400> SEQUENCE: 44
gtgctcccca gattgttcta ttttggcttt tataaagaat tgtttagatc ctttgaattg      60
aagaatgtgt atagctttgt ttctttggca agcccaccca ctctacccett tccttctttt    120 gaacaacaga gatgaatatc acaacaggcc tacgaagcca gtgtcatggt gggaagatat    180
tgatatagtt ggaggaagag atgagattgc tggaggaaca tggttggctt gttcaagaga    240
aggaagagtt gcttttctga ccaatgtttt ggagcttcgt tcccttcctg aggctaaaag    300
cagaggagac ctacctgtct catttcttaa gagtggaaag catccgaaag aatttgcaga    360
aagtctaaaa atggaagctc attattacaa tgggttcaac ttgattgtgg ccgatattcc    420
gtc                                                                   423

<210> SEQ ID NO 45
<211> LENGTH: 119
<212> TYPE: PRT
<213> ORGANISM: Glycine max

<400> SEQUENCE: 45

Met Cys Ile Ala Leu Phe Leu Trp Gln Ala His Pro Leu Tyr Pro Phe
1               5                   10                  15
Leu Leu Leu Asn Asn Arg Asp Glu Tyr His Asn Arg Pro Thr Lys Pro
            20                  25                  30
Val Ser Trp Trp Glu Asp Ile Asp Ile Val Gly Gly Arg Asp Glu Ile
        35                  40                  45
Ala Gly Gly Thr Trp Leu Ala Cys Ser Arg Glu Gly Arg Val Ala Phe
    50                  55                  60
Leu Thr Asn Val Leu Glu Leu Arg Ser Leu Pro Glu Ala Lys Ser Arg
65                  70                  75                  80
Gly Asp Leu Pro Val Ser Phe Leu Lys Ser Gly Lys His Pro Lys Glu
                85                  90                  95
Phe Ala Glu Ser Leu Lys Met Glu Ala His Tyr Tyr Asn Gly Phe Asn
            100                 105                 110
Leu Ile Val Ala Asp Ile Pro
        115

<210> SEQ ID NO 46
<211> LENGTH: 542
<212> TYPE: DNA
<213> ORGANISM: Beta vulgaris

<400> SEQUENCE: 46
cccacgcgtc cgcccacgcg tccgcccacg cgtccgcgga cgcgtgggtc gacccacgcg     60
tccgtttgaa ccacttttca attttcgagc tgaaacatga agtgcatta attcacaccc    120 aaacctgcaa cacatctttc tgaatagctc aaaattcgaa attccactca tgcaagagca    180
```

```
agaatttagc atgaacatga aatgacaaat ttgaaatttc caccactaat catgaaaaac    240
ccatgaaaaa gaaacgtgat gtgcatcgca atatttcaat ggcaatccca cccactttac    300
ccatttcttc tactcctcaa ccgcgacgaa tatcataccc ggccaacaaa tccagcaggg    360
tggtgggaag gtgaagaaat tgttggtggg aagatgaag ttggtggtgg gacatggttg     420
gcttgttcca aggtggaag aattgctttt cttaccaatt ttagagagag agaatcaatt     480
cctcatgcta aaagtagagg agatttgcct gttcgttttc ttaagtgtaa gaaagatccg    540
gc                                                                   542
```

<210> SEQ ID NO 47
<211> LENGTH: 94
<212> TYPE: PRT
<213> ORGANISM: Beta vulgaris

<400> SEQUENCE: 47

```
Met Cys Ile Ala Ile Phe Gln Trp Gln Ser His Pro Leu Tyr Pro Phe
1               5                   10                  15

Leu Leu Leu Leu Asn Arg Asp Glu Tyr His Thr Arg Pro Thr Asn Pro
            20                  25                  30

Ala Gly Trp Trp Glu Gly Glu Glu Ile Val Gly Gly Lys Asp Glu Val
        35                  40                  45

Gly Gly Gly Thr Trp Leu Ala Cys Ser Lys Gly Gly Arg Ile Ala Phe
    50                  55                  60

Leu Thr Asn Phe Arg Glu Arg Glu Ser Ile Pro His Ala Lys Ser Arg
65                  70                  75                  80

Gly Asp Leu Pro Val Arg Phe Leu Lys Cys Lys Lys Asp Pro
                85                  90
```

<210> SEQ ID NO 48
<211> LENGTH: 190
<212> TYPE: DNA
<213> ORGANISM: Capsicum annuum

<400> SEQUENCE: 48

```
agaatgtgca tagcagtgtt tatttggcaa gcagacagta gatattcatt agtgttgttg     60
ttgaacagag atgaatatca caataggcca acaaaggcag ttcattggtg ggaaggtgga    120
gatcaaatag ttggtggtaa agatgacgtt ggtggtggta cttggttacc ttcttcaaca    180
aatggtaaat                                                           190
```

<210> SEQ ID NO 49
<211> LENGTH: 62
<212> TYPE: PRT
<213> ORGANISM: Capsicum annuum

<400> SEQUENCE: 49

```
Met Cys Ile Ala Val Phe Ile Trp Gln Ala Asp Ser Arg Tyr Ser Leu
1               5                   10                  15

Val Leu Leu Leu Asn Arg Asp Glu Tyr His Asn Arg Pro Thr Lys Ala
            20                  25                  30

Val His Trp Trp Glu Gly Gly Asp Gln Ile Val Gly Gly Lys Asp Asp
        35                  40                  45

Val Gly Gly Gly Thr Trp Leu Pro Ser Ser Thr Asn Gly Lys
    50                  55                  60
```

<210> SEQ ID NO 50

<211> LENGTH: 719
<212> TYPE: DNA
<213> ORGANISM: Lactuca sativa
<220> FEATURE:
<221> NAME/KEY: misc_feature
<222> LOCATION: (687)..(687)
<223> OTHER INFORMATION: n is a, c, g, or t

<400> SEQUENCE: 50

```
gggaggaaga gtgtcattcc ttactaacgt cttggagctt cacactctcc cggaagccaa     60
aactagagga gaccttccac ttcgtttctt ggagagcaat aagagtccag aggaatttgc    120
aaaggaattg gtgaaggagg ttcatgagta caatgggttc aacctcataa cccttgacat    180
ttcttcaaaa acgatgtttt atatatcaaa tagaccaaaa agtgaacctc caactgttca    240
acaggttcaa ccaggcatcc atgtcctctc caatgccaag ctcgactccc cttggccaaa    300
ggctcaacgt ttgaagttta attttaaaaa gttgcttagc gcatatgata aagacgaaga    360
tatacccatg aaggatatga tggacaaact aatgagagac accatgaaag cagaaaagag    420
tcaacttcct aatatttgtt ccattgattg ggagcataat ctaagctcga tatttgttga    480
agtagacacc ccgttgggtc gttatgggac gagaagcatg attgcactaa gtatcaaaga    540
taccgaagaa gcaagttttc atgagaccta cattgaaaga ggattttggt gggagaaaac    600
cgtcgattat tatgttactc cacaagttaa aataaaagat atcgtcttct aagactaaat    660
atacgttaca aatatttaaa atacagnctt tctctctata tatctttat atataaaaa     719
```

<210> SEQ ID NO 51
<211> LENGTH: 216
<212> TYPE: PRT
<213> ORGANISM: Lactuca sativa

<400> SEQUENCE: 51

```
Gly Gly Arg Val Ser Phe Leu Thr Asn Val Leu Glu Leu His Thr Leu
 1               5                  10                  15
Pro Glu Ala Lys Thr Arg Gly Asp Leu Pro Leu Arg Phe Leu Glu Ser
            20                  25                  30
Asn Lys Ser Pro Glu Glu Phe Ala Lys Glu Leu Val Lys Glu Val His
        35                  40                  45
Glu Tyr Asn Gly Phe Asn Leu Ile Thr Leu Asp Ile Ser Ser Lys Thr
    50                  55                  60
Met Phe Tyr Ile Ser Asn Arg Pro Lys Ser Glu Pro Pro Thr Val Gln
65                  70                  75                  80
Gln Val Gln Pro Gly Ile His Val Leu Ser Asn Ala Lys Leu Asp Ser
                85                  90                  95
Pro Trp Pro Lys Ala Gln Arg Leu Lys Phe Asn Phe Lys Lys Leu Leu
            100                 105                 110
Ser Ala Tyr Asp Lys Asp Glu Asp Ile Pro Met Lys Asp Met Met Asp
        115                 120                 125
Lys Leu Met Arg Asp Thr Met Lys Ala Glu Lys Ser Gln Leu Pro Asn
    130                 135                 140
Ile Cys Ser Ile Asp Trp Glu His Asn Leu Ser Ser Ile Phe Val Glu
145                 150                 155                 160
Val Asp Thr Pro Leu Gly Arg Tyr Gly Thr Arg Ser Met Ile Ala Leu
                165                 170                 175
Ser Ile Lys Asp Thr Glu Glu Ala Ser Phe His Glu Thr Tyr Ile Glu
            180                 185                 190
Arg Gly Phe Trp Trp Glu Lys Thr Val Asp Tyr Tyr Val Thr Pro Gln
```

```
                195                 200                 205
Val Lys Ile Lys Asp Ile Val Phe
    210                 215

<210> SEQ ID NO 52
<211> LENGTH: 522
<212> TYPE: DNA
<213> ORGANISM: Sorghum bicolor

<400> SEQUENCE: 52
agctaagata gttgcaaaca agcgagttac ttacaaccaa ccaaaggagt agaaaccacc      60
tgaagccatg tgcattgctg catggatttg gcaggctcac cctgtgcacc aactcctcct     120
gcttctcaac agagatgagt tccacagcag gcctacaaaa gcagtaggat ggtggggaga     180
aggctcaaag aagattcttg gtggcaggga tgtgcttggt ggaggaacat ggatggggtg     240
caccaaggat ggaaggcttg ccttcctgac caatgtgctt gaaccagatg ccatgcccgg     300
tgcacggact aggggagatc tgcctctcag gttcctgcag agcaacaaga gcccactcga     360
agttgcaact gaagtggcag aagaagctca taaatacaat ggcttcaacc tcatactagc     420
tgatctaaca acaaatatca tggtctatgt gtcaaaccgg cctaaggggc agcctgcaac     480
aattcaactc gtctcaccag gactccatgt gctgtccaat gc                       522

<210> SEQ ID NO 53
<211> LENGTH: 151
<212> TYPE: PRT
<213> ORGANISM: Sorghum bicolor

<400> SEQUENCE: 53

Met Cys Ile Ala Ala Trp Ile Trp Gln Ala His Pro Val His Gln Leu
1               5                   10                  15

Leu Leu Leu Leu Asn Arg Asp Glu Phe His Ser Arg Pro Thr Lys Ala
            20                  25                  30

Val Gly Trp Trp Gly Glu Gly Ser Lys Lys Ile Leu Gly Gly Arg Asp
        35                  40                  45

Val Leu Gly Gly Gly Thr Trp Met Gly Cys Thr Lys Asp Gly Arg Leu
    50                  55                  60

Ala Phe Leu Thr Asn Val Leu Glu Pro Asp Ala Met Pro Gly Ala Arg
65                  70                  75                  80

Thr Arg Gly Asp Leu Pro Leu Arg Phe Leu Gln Ser Asn Lys Ser Pro
                85                  90                  95

Leu Glu Val Ala Thr Glu Val Ala Glu Glu Ala His Lys Tyr Asn Gly
            100                 105                 110

Phe Asn Leu Ile Leu Ala Asp Leu Thr Thr Asn Ile Met Val Tyr Val
        115                 120                 125

Ser Asn Arg Pro Lys Gly Gln Pro Ala Thr Ile Gln Leu Val Ser Pro
    130                 135                 140

Gly Leu His Val Leu Ser Asn
145                 150

<210> SEQ ID NO 54
<211> LENGTH: 1132
<212> TYPE: DNA
<213> ORGANISM: Triticum aestivum
<220> FEATURE:
<221> NAME/KEY: misc_feature
<222> LOCATION: (17)..(17)
<223> OTHER INFORMATION: n is a, c, g, or t
```

<400> SEQUENCE: 54

```
aatcctcagg gttacgncga cccacgcgtc cgcaaacaca caaggcgcac ggttgcgaaa      60
caagggaatt atttagaagc aggaaggaac acctgaagcc atgtgtatcg ctgcatggat     120
ttggcaggct cacccacagc atcagctcct gcttctgctc aacagagatg agttccatag     180
caggcctaca aaggcagtag gatggtgggg ggagggctca atgaagattc ttggcggcag     240
ggatgtactt ggtggaggaa catggatggg gagcaccaaa gatggcagac ttgccttcct     300
gaccaatgtg ctcgagcctg atgcgatgcc tggcgcacgc actagggag acctgcccct     360
caggttcctg cagggcaaca agagcccact ggaggttgca actgaagtcg caaaagaagc     420
tgatgagtac aatggcttca accttatact agctgatcta accaggaatg tcatggttta     480
tgtgtcaaac cggccaaagg gcagcctgc gacgattcag ctcgtctcac caggactcca     540
tgtgttgtcc aatgcaaggc tagacagccc ttggcagaag gcaattcgcc ttggtaaaaa     600
cttcagggag tttataagga agcatggtga tgatgaagtt gaagcgaagg atatagctga     660
tagactaatg actgacacca cgagggctga taaagatagg ctgccaaaca ccggttgtga     720
tcccaactgg gagcacggtc tgagctccat cttcatcgag gtgcaaactg acgaagggct     780
ctatgggaca aggagcacag cagttctttc agtgaactat gatggagaag ctagcttata     840
tgagaagtac ctcgagagtg gtatatggaa gaaccacaca gtgcattacc agatagaatt     900
gccaatgcgc acctaaaggc aggagcctca ataggaaga aagaatgaat agctaccatt     960
gtgcatgctg ttatttccac agttgcgctt taagatcaca taatgatctc taattatggc    1020
aattaaatta tttactgtat gcggatctat aaattcagag acagatcaag tcaaattgtt    1080
gaatatatat acataataat aatatgatat agtatgtgta tttacagact tc            1132
```

<210> SEQ ID NO 55
<211> LENGTH: 271
<212> TYPE: PRT
<213> ORGANISM: Triticum aestivum

<400> SEQUENCE: 55

```
Met Cys Ile Ala Ala Trp Ile Trp Gln Ala His Pro Gln His Gln Leu
1               5                   10                  15

Leu Leu Leu Asn Arg Asp Glu Phe His Ser Arg Pro Thr Lys Ala
            20                  25                  30

Val Gly Trp Trp Gly Glu Gly Ser Met Lys Ile Leu Gly Gly Arg Asp
        35                  40                  45

Val Leu Gly Gly Gly Thr Trp Met Gly Ser Thr Lys Asp Gly Arg Leu
    50                  55                  60

Ala Phe Leu Thr Asn Val Leu Glu Pro Asp Ala Met Pro Gly Ala Arg
65                  70                  75                  80

Thr Arg Gly Asp Leu Pro Leu Arg Phe Leu Gln Gly Asn Lys Ser Pro
                85                  90                  95

Leu Glu Val Ala Thr Glu Val Ala Lys Glu Ala Asp Glu Tyr Asn Gly
            100                 105                 110

Phe Asn Leu Ile Leu Ala Asp Leu Thr Arg Asn Val Met Val Tyr Val
        115                 120                 125

Ser Asn Arg Pro Lys Gly Gln Pro Ala Thr Ile Gln Leu Val Ser Pro
    130                 135                 140

Gly Leu His Val Leu Ser Asn Ala Arg Leu Asp Ser Pro Trp Gln Lys
145                 150                 155                 160

Ala Ile Arg Leu Gly Lys Asn Phe Arg Glu Phe Ile Arg Lys His Gly
```

```
                165                 170                 175
Asp Asp Glu Val Glu Ala Lys Asp Ile Ala Asp Arg Leu Met Thr Asp
                    180                 185                 190

Thr Thr Arg Ala Asp Lys Asp Arg Leu Pro Asn Thr Gly Cys Asp Pro
                195                 200                 205

Asn Trp Glu His Gly Leu Ser Ser Ile Phe Ile Glu Val Gln Thr Asp
            210                 215                 220

Glu Gly Leu Tyr Gly Thr Arg Ser Thr Ala Val Leu Ser Val Asn Tyr
225                 230                 235                 240

Asp Gly Glu Ala Ser Leu Tyr Glu Lys Tyr Leu Glu Ser Gly Ile Trp
                245                 250                 255

Lys Asn His Thr Val His Tyr Gln Ile Glu Leu Pro Met Arg Thr
            260                 265                 270
```

<210> SEQ ID NO 56
<211> LENGTH: 1090
<212> TYPE: DNA
<213> ORGANISM: Saccharum officinarum

<400> SEQUENCE: 56

```
agcaaaacaa gcgagttact tacaaccaac caaggagtag aaaccacctg aagccatgtg      60
cattgctgca tggatttggc aggctcaccc tgtgcaccaa ctcctcctga ttctcaacag     120
agatgagttc cactgcaggc ctacaaaagc agtaggatgg tggggagaag gctcaaagaa     180
gattcttggc ggcagggatg tgcttggtgg aggaacatgg atgggttgca ccaaggatgg     240
caggcttgcc ttcctgacca atgtgcttga accagatgcc atgcccggtg cacggactag     300
gggagatctg cctctcaggt tcctgcagag caacaagagc ccactcgaag ttgcaactga     360
agtggcagaa gaagctcatg aatacaatgg gttcaacctc atactagctg atctaacaac     420
aaatatcatg gtctatgtgt caaatcggcc taaggggcag cctgcaacaa ttcaactcgt     480
ctcaccagga ctccatgtgc tgtccaatgc aaggctagat agcccttggc agaaggcaat     540
tcgccttggt aaaaacttca aggagcttct tagggagcat ggtgacgatg agattgaagt     600
gaaggatata gttgagaggc taatgactga caccacaaag gctgacaaag atagactgcc     660
aaacactggt tgtgatccca actgggagca tggtctgagc tccatcttca tcgaggtgca     720
aactgaccaa gggctctacg ggacacggag cacagccgtt ttatcagtga actatgatgg     780
tgaagctagc ttgtacgaga agtaccttga gagtggtata tggaaggacc acacagtgaa     840
ttaccagata gagtagtagg cattgcacag gaaaagctgg caacctcaaa taaatagaga     900
tatgaagcag acacaattgt ggatttcatt ctttccctaa tccctagtca ccttcacgac     960
tatctaagat cccatcatga tgccaattac attatttact gtaagcagat tgtcacttg    1020
acgataaaat gtcaagcaga agtttaagtt taaatatata caccaaatat ataaatttac    1080
agacttcgtg                                                           1090
```

<210> SEQ ID NO 57
<211> LENGTH: 266
<212> TYPE: PRT
<213> ORGANISM: Saccharum officinarum

<400> SEQUENCE: 57

```
Met Cys Ile Ala Ala Trp Ile Trp Gln Ala His Pro Val His Gln Leu
1               5                   10                  15
Leu Leu Ile Leu Asn Arg Asp Glu Phe His Cys Arg Pro Thr Lys Ala
                20                  25                  30
Val Gly Trp Trp Gly Glu Gly Ser Lys Lys Ile Leu Gly Gly Arg Asp
            35                  40                  45
Val Leu Gly Gly Gly Thr Trp Met Gly Cys Thr Lys Asp Gly Arg Leu
50                      55                  60
Ala Phe Leu Thr Asn Val Leu Glu Pro Asp Ala Met Pro Gly Ala Arg
65                      70                  75                  80
Thr Arg Gly Asp Leu Pro Leu Arg Phe Leu Gln Ser Asn Lys Ser Pro
                85                  90                  95
Leu Glu Val Ala Thr Glu Val Ala Glu Ala His Glu Tyr Asn Gly
                100                 105                 110
Phe Asn Leu Ile Leu Ala Asp Leu Thr Thr Asn Ile Met Val Tyr Val
            115                 120                 125
Ser Asn Arg Pro Lys Gly Gln Pro Ala Thr Ile Gln Leu Val Ser Pro
130                 135                 140
Gly Leu His Val Leu Ser Asn Ala Arg Leu Asp Ser Pro Trp Gln Lys
145                 150                 155                 160
Ala Ile Arg Leu Gly Lys Asn Phe Lys Glu Leu Leu Arg Glu His Gly
                165                 170                 175
Asp Asp Glu Ile Glu Val Lys Asp Ile Val Glu Arg Leu Met Thr Asp
                180                 185                 190
Thr Thr Lys Ala Asp Lys Asp Arg Leu Pro Asn Thr Gly Cys Asp Pro
                195                 200                 205
Asn Trp Glu His Gly Leu Ser Ser Ile Phe Ile Glu Val Gln Thr Asp
            210                 215                 220
Gln Gly Leu Tyr Gly Thr Arg Ser Thr Ala Val Leu Ser Val Asn Tyr
225                 230                 235                 240
Asp Gly Glu Ala Ser Leu Tyr Glu Lys Tyr Leu Glu Ser Gly Ile Trp
                245                 250                 255
Lys Asp His Thr Val Asn Tyr Gln Ile Glu
                260                 265
```

<210> SEQ ID NO 58
<211> LENGTH: 743
<212> TYPE: DNA
<213> ORGANISM: Artificial sequence
<220> FEATURE:
<223> OTHER INFORMATION: functional fragments of the cwp1 gene promoter

<400> SEQUENCE: 58

```
tgccgtccta ttcttagaat actcaagtaa tttaacgtag tggtgaaaat ttgataaatt      60
aattatatac taattttca gtcttatttt atgtggtata tttaattgga tatgtagttt     120
aagaaataat aaaaacttta aaatatttat aaatttactt ttctaaaaaa gtgaattcaa     180
ttttttctct cctcataaat gtattagagt attatcatta aaattaagtg ggactaataa     240
aggtaaaaaa taattattc ctttaaatta tttaaccata taagaaaatg tgacattctt     300
ttttagactt gactaaaata gaaaataatg tcatatatat aaaatgagac gaaaaaagta     360
aatattaatt taaaatttaa aactttaggg taatagctac tttgaattac ctagatttca     420
ataaaattca acatataata aaacatacta atttacaatt tttaaaataa tatgactaaa     480
agtcatatta ttcaaaaaac aatctatacc gccgtcacct agttactta atttgtgtag     540
```

```
cttctagtac atacattttt aaactttatc tgaatttaat attttaatta tattaaacat    600
ttattaaaat ttataaaatt taaattgacg taatataatg aagagagtag tactatataa    660
accatgtgag tactaacatg atcttcatct tattcttgtt tttatttata gaaacaataa    720
aatagttata aaattaatca atc                                           743
```

ISOLATED POLYPEPTIDES AND POLYNUCLEOTIDES ENCODING SAME FOR GENERATING PLANTS WITH INCREASED CUTICLAR WATER PERMEABILITY

RELATED APPLICATIONS

This application is a division of U.S. patent application Ser. No. 11/663,151 filed on Dec. 29, 2008 issued on 9 Jul. 2013 as U.S. Pat. No. 8,481,809, which is a National Phase of PCT Patent Application No. PCT/IL2005/001000 filed on Sep. 19, 2005, which claims the benefit of priority of Israel Patent Application No. 164125 filed on Sep. 19, 2004.

The contents of all of the above documents are incorporated by reference as if fully set forth herein.

SEQUENCE LISTING STATEMENT

The ASCII file, entitled 56480SequenceListing.txt, created on May 27, 2013, comprising 66,793 bytes, submitted concurrently with the filing of this application is incorporated herein by reference.

FIELD AND BACKGROUND OF THE INVENTION

The present invention relates to polynucleotides and polypeptides for increasing cuticular water permeability of a plant expressing same. More particularly the present invention relates to genetically modified plants capable of producing dehydrated fruits, such as tomato.

Aerial portions of higher plants are covered with a continuous extracellular layer of cuticle. The cuticle is a polymer matrix which is mostly composed of cutin monomers (primarily short-chain hydroxylated fatty acids) and various amounts of cuticular waxes (solvent-soluble lipids). Both the cutin and the wax components vary greatly in amount and composition between different plant species and plant organs (Holloway, 1982). Although the components and structure of plant cuticle as well as the biological and genetic regulation of its biosynthesis has been extensively investigated (Kolattukudy, 1980; Koornneef et al., 1989; Blee and Schuber, 1993; Arts et al., 1996; Negruk et al., 1996; Millar et al., 1997; Todd et al., 1999; Yaphremov et al., 1999; Flebig et al., 2000; Pruitt et al., 2000; Wellesen et al., 2001 Hooker et al., 2002; Chen et al., 2003; Kuns and Samuels, 2003; Kurata et al., 2003; Aharoni et al., 2004; Schnurr et al. 2004), the mechanisms controlling the differentiation and/or function of the cuticle remain to be characterized.

The tomato fruit cuticle is a thin layer with a 4-10 micron thickness with two unique structural properties (Wilson and Sterling, 1976). First, the cutin deposits are arranged in a laminar structure—the layers are assembled in parallel to the epidermis cells. The second property of the tomato fruit cuticle is that it does not contain any stomata, pores or channels. As a result, the water permeability of the tomato skin is very low and the fully ripe tomato fruit retains its water content. The water permeability of a number of other cuticles lacking stomata (astomatous) and the mechanism of water transport across them have been the subjects of numerous investigations (Schönherr, 1976a; Schönherr and Schmidt, 1979; Riederer and Schreiber, 2001). Apparently, both the cutin and wax components have an integrated effect against water loss from the organ. In some cases, the thickness of the cuticular layer is inversely proportional to diffusion of water across cuticular membranes (Lownds et al., 1993). However, frequently the cuticular wax component is primary in affecting plant water permeability. For example, removal of the epicuticular wax layer from tomato fruit cuticles by organic solvents increased their water permeability by a factor of 300 to 500, as evidenced by rapid plant dehydration (Schönherr, 1976b). Additional evidence for the role of cuticular waxes as a transpiration barrier in tomato fruits is the recently reported gene encoding the enzyme very-long-chain-fatty acid (VLFA) β-ketoacyl-CoA synthase (LeCER6, Vogg et al., 2004). This gene plays an important role in the synthesis of VFLA which are a major component in fruit cuticular wax. A loss of function mutation in this gene led to the reduction of n-alkanes and aldehydes with chain lengths beyond $C_{30}$ in both leaf and fruit waxes. Tomato fruits with the LeCER6 mutation were characterized with a 4-fold increase in water permeability.

Another factor affecting water permeability of tomato fruit cuticle is the presence of cracking on the cuticular surface. Fruit cracking has received much research attention (Cotner et al., 1969; Voisey et al., 1970; peet, 1992; peet and willits, 1995). Tomato fruits are affected by three main types of cracking: i) Concentric cracking (coarse cracking); ii) Radial cracking (splitting); and iii) Cuticle cracking (russeting) (Bakker, 1988). The first two types of cracking are deep and extended fissures that penetrate through the fruit pericarp and in addition to water loss also allow pathogen penetration and fruit decomposition.

Unlike radial or concentric cracks, cuticle cracks are superficial micro fissures of the cuticle that are generally confined to the cuticle and do not penetrate to the pericarp cells. The causes and circumstances leading to fruit cracking in tomatoes are mostly unclear and may be related to cuticular layer thickness (Emmons and Scott, 1998), shape of the underlying epidermis cells (Conter et al., 1969; Emmons and Scott, 1998), fruit shape (Considine and Brown, 1981), fruit size (Koske et al., 1980; Emmons and Scott, 1997), relative humidity around the fruit (Young, 1947; Tukey, 1959), strong foliage pruning (Ehret et al., 1993) and the tensile strength and extensibility of the epidermis (Bakker, 1988).

The occurrence of cracks in tomato fruit also has a significant genetic component, which is mainly expressed upon gene transfer from wild species of Lycopersicon. Fulton et al. (2000) described a trait, "Epidermal reticulation" (Er), and, using an advanced backcross QTL analysis strategy (with the wild type L. parviflorum) reported four QTLs affecting it. Cuticlar cracks also have been reported in Lycopersicon fruit derived from crosses of L. esculentum and other wild species such has L. hirsutum (WO 0113708) and L. penellii (Monforte et al., 2001).

Cracks in fruit cuticle, particularly extreme cracks which are visually evidenced as epidermal reticulation, due to the development of a suberized coating along the fissure (Monforte et al., 2001), are generally considered to be negative phenomenon due to the esthetic damages that lower fruit value (Tukey, 1959), as well as due to the loss of fruit moisture content. However, the economic potential of fruits that dehydrate while whole and while still attached to the vine, is high. Dehydrated tomato products comprise an important portion of the tomato industry. The production of tomato pastes, ketchup, and other processed tomato products is dependant on the energy-requiring steps of dehydration. In addition, "sun-dried" tomato fruit are prepared in a drying process which consists of dehydrating cut tomato fruit either in the sun or in drying ovens. Both sun-drying and oven drying may lead to losses in food quality. For example, levels of ascorbic acid, one of the major nutritional contributions of tomatoes in the human diet, decrease significantly in response to sun-drying or oven-drying (Ojimelukwe, 1994). Furthermore, the necessity to cut the tomato fruit in half before the drying process does not allow for the production of whole dried tomato fruit.

The present inventor has previously described dehydrated tomatoes having reduced water content using classical genetic breeding techniques (WO 01/13708). It is appreciated that the classical genetic breeding techniques are limiting to gene transfer within species or between closely related species of the same genus. Also, classical breeding is characterized by relatively large introgressions which include other undesirable genes closely linked to the gene of interest.

Introgressed cultivated tomato plants have been previously described by Eshed and Zamir (1985) having a genetic background (Introgression line IL4-4, i.e., resulting from an introgression extending from telomeric marker TG464 to centromeric marker CT50; ca20 cM) which may be associated with undesired traits. Similarly, Monforte et al. (2001) have described tomato plants having a similar genetic background derived from *L. hirsutum* [sub-near introgression lines TA1468, TA1469, TA1476 which span from, and including, TG464 to CT173 (approximately. 10 cM)] and which display numerous effects, including undesirable effects.

There is thus a widely recognized need for and it would be highly advantageous to have genetically modified plants with increased cuticular water permeability which are devoid of the above limitations.

SUMMARY OF THE INVENTION

According to one aspect of the present invention there is provided an isolated polynucleotide comprising a nucleic acid sequence encoding a polypeptide having an amino acid sequence at least 88% homologous to SEQ ID NO: 22, the polypeptide being capable of increasing a cuticular water permeability of a plant expressing same.

According to further features in preferred embodiments of the invention described below, the nucleic acid sequence is as set forth in SEQ ID NO: 21 or 23.

According to still further features in the described preferred embodiments the amino acid sequence is as set forth in SEQ ID NO: 22.

According to another aspect of the present invention there a nucleic acid construct comprising the isolated polynucleotide.

According to still further features in the described preferred embodiments the nucleic acid construct further comprising a promoter operably linked to the nucleic acid sequence.

According to another aspect of the present invention there a host cell comprising the nucleic acid construct.

According to another aspect of the present invention there a genetically modified plant comprising the isolated polynucleotide.

According to another aspect of the present invention there an oligonucleotide capable of specifically hybridizing with the isolated polynucleotide According to another aspect of the present invention there is provided an isolated polypeptide comprising an amino acid sequence at least 88% homologous to SEQ ID NO: 22, the polypeptide being capable of increasing a cuticular water permeability of a plant expressing same.

According to yet another aspect of the present invention there is provided an antibody capable of specifically recognizing the polypeptide.

According to yet another aspect of the present invention there is provided a cultivated tomato plant having a genome comprising an introgression derived from a wild *Lycopersicon* spp. the introgression comprising a portion of chromosome 4 of the *Lycopersicon* spp. smaller than a chromosomal fraction extending from telomeric marker TG464 to centromeric marker CT173, the introgression being capable of increasing cuticular water permeability of the cultivated tomato plant.

According to still another aspect of the present invention there is provided a method of producing a dehydrated fruit of a crop plant, the method comprising genetically modifying the plant to express a polypeptide having an amino acid sequence at least 30% homologous to SEQ ID NO: 22, the polypeptide being capable of increasing a cuticular water permeability of a plant expressing same.

According to still further features in the described preferred embodiments the method further comprising:
allowing the fruit to dehydrate on the plant; and subsequently
collecting the dehydrated fruit.

According to still further features in the described preferred embodiments the method further comprising:
removing the fruit from the crop plant prior to dehydration thereof; and subsequently allowing the fruit to dehydrate.

According to an additional aspect of the present invention there is provided a genetically modified seed comprising an isolated polynucleotide comprising a nucleic acid sequence encoding a polypeptide having an amino acid sequence at least 30% homologous to SEQ ID NO: 22, the polypeptide being capable of increasing a cuticular water permeability of a plant expressing same.

According to yet an additional aspect of the present invention there is provided a genetically modified fruit comprising an isolated polynucleotide comprising a nucleic acid sequence encoding a polypeptide having an amino acid sequence at least 30% homologous to SEQ ID NO: 22, the polypeptide being capable of increasing a cuticular water permeability of a plant expressing same.

According to still further features in the described preferred embodiments the nucleic acid sequence is as set forth in SEQ ID NO: 21, 23, 24, 26, 28, 30, 32, 34, 36, 38, 40, 42, 44, 46, 48, 50, 52, 54 or 56.

According to still further features in the described preferred embodiments the amino acid sequence is as set forth in SEQ ID NO: 22, 25, 27, 29, 31, 33, 35, 37, 39, 41, 43, 45, 47, 49, 51, 53, 55 or 57.

According to still an additional aspect of the present invention there is provided a genetically modified plant expressing a polypeptide having an amino acid sequence at least 30% homologous to SEQ ID NO: 22, the polypeptide being capable of increasing a cuticular water permeability of the plant.

The present invention successfully addresses the shortcomings of the presently known configurations by providing polynucleotides and polypeptides being capable of increasing cuticular water permeability of a plant expressing same and by providing genetically modified plants for producing dehydrated fruits.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b are graphs showing the effect of cwp (PUT) genotype on dehydration rate in population 2148 (FIG. 1a) and population 2149 (FIG. 1b). In the population 2148 the trait of dehydration behaves as a completely dominant trait while in 2149 it behaves as a partially dominant trait. Fruit were picked when red-ripe and allowed to dehydrate at ambient room temperature and weighed at approximately daily intervals. Data are expressed as Log % weight. The superscripts HH, HE and EE indicate the genotypes of the segregating plants.

FIGS. 2a-c show fine mapping of CWP gene. FIG. 2a—CAPS marker analysis of the TG464 molecular marker. Genomic DNA was extracted from 20 $F_2$ individuals segregating for dehydration rate. PCR analysis was performed using the appropriate primers for TG464 marker which showed polymorphism between the two parental species. PCR products were cleaved with HinF1 endonuclease restriction site enzyme, and electrophoresed on 2% agarose gel. The + or − signs indicate the presence or absence of microfissures and the dehydrating condition. E—*L. esculentum*. H—*L. hirsutum*. M—HindIII/EcorI lambda marker (Fermentas Cat. No. SM0191) FIG. 2b—Genetic linkage map (in cM) of the chromosomal region of CWP oriented relative to the position of the centromere. *Lycopersicon penellii* introgression lines IL4.3 and IL4.4 (Eshed and Zamir, 1995) are indicated. The hatched bar represents the *L. hirsutum* segment in the near-isogenic line that was used as the dehydrating donor parent in this analysis. FIG. 2c—Magnification of the chromosomal segment flanking the Cwp gene.

FIGS. 3a-b show physical positioning of CWP gene. FIG. 3a—Genetically ordered contiguous BACs creating a bridge between CT61 and TG464 CAPS markers, and phenotypic analysis of the recombinants and the characterization of the recombinants according to polymorphisms of the sequenced BAC ends. Each recombinant genotype is represented by a bar divided into hatches (*L. hirsutum* genotype) and empty (*L. esculentum* genotype) segments. FIG. 3b—Magnification of the three crossover events in BAC 37B8. The three crossover events are those of the first three recombinants presented in FIG. 3a.

Figure 4:
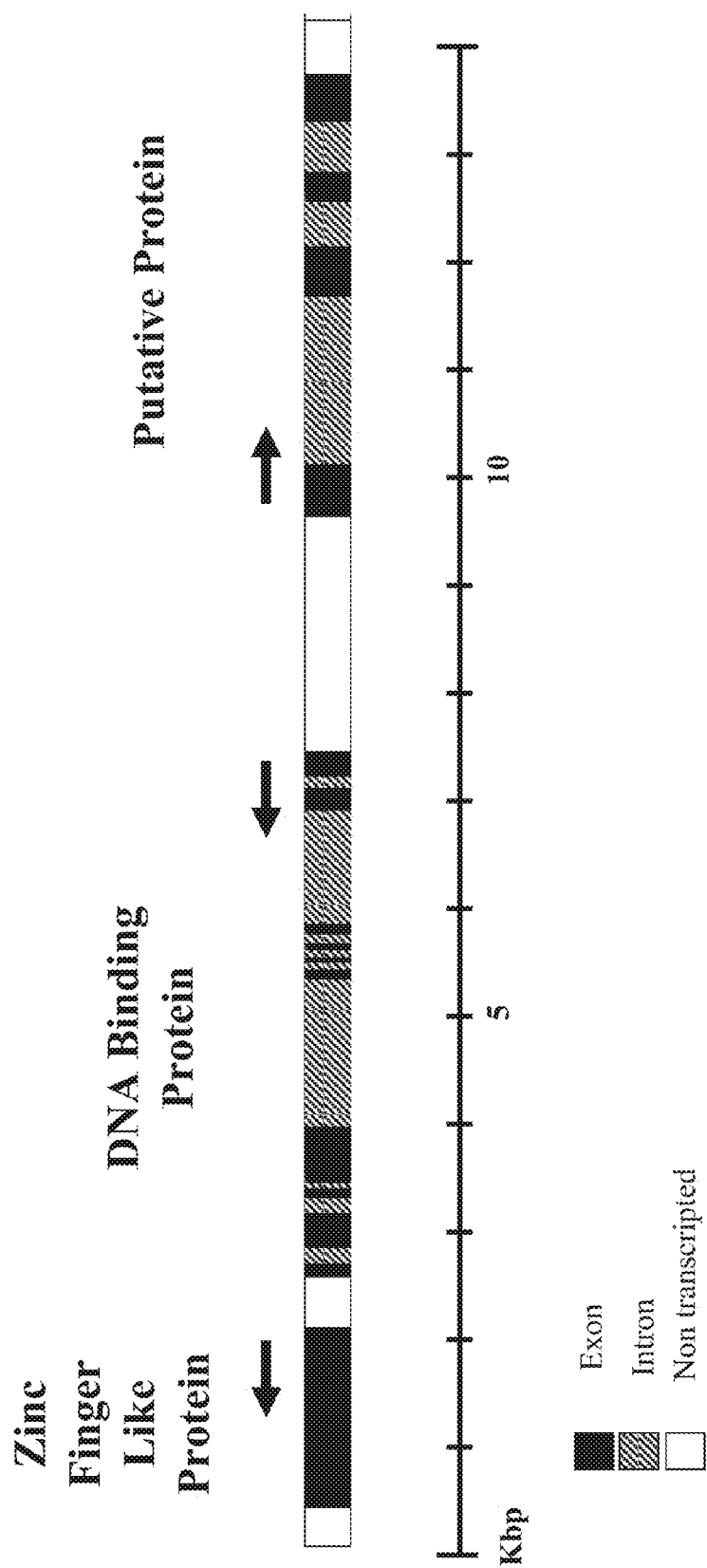

FIG. 4 illustrates the 15 kb introgression from *L. hirsutum* which includes the Cwp gene. The sequence was analyzed for homologous open reading frames using the NCBI program TBLAST. Three homologous sequences were identified and the direction of each of the open reading frames is indicated by arrows.

Figures 5A, 5B:
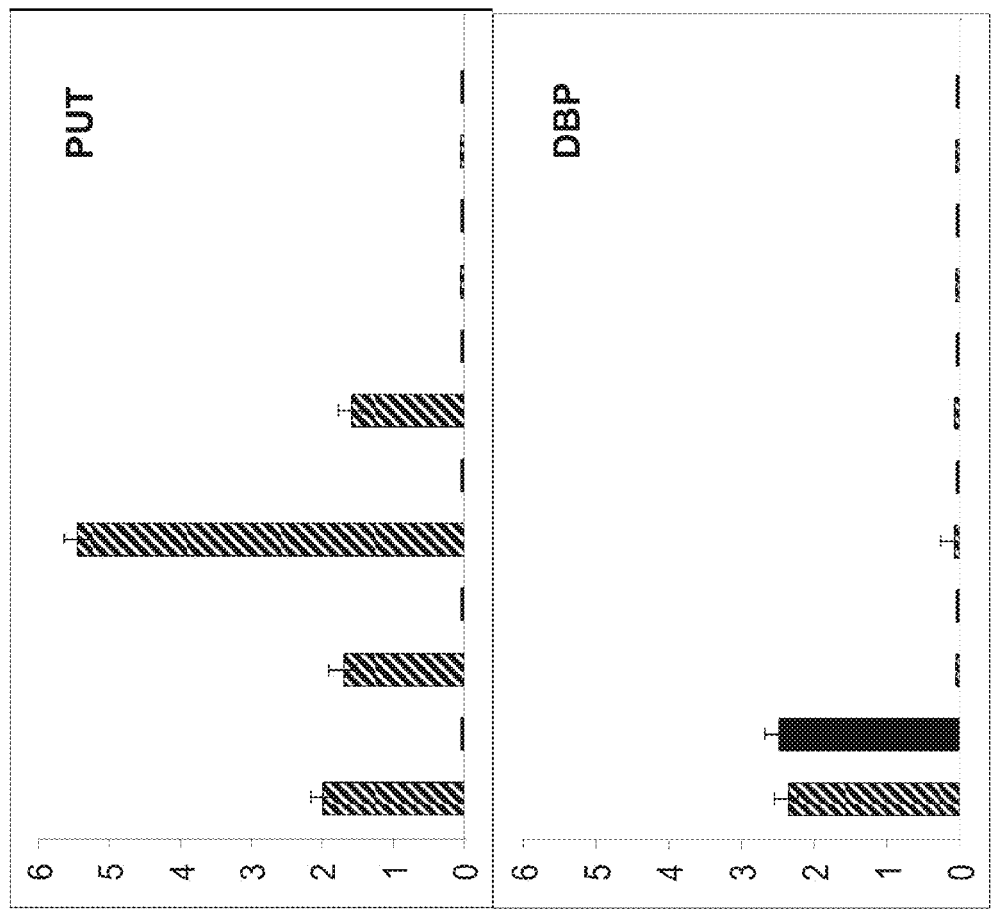

FIGS. 5a-b are graphs showing expression analysis of the PUT (FIG. 5a) and the DBP (FIG. 5b) genes in developing ovaries and fruitlets of tomato. Expression was measured on extracted cDNA as described in the Methods section using an On-line quantitative PCR and is expressed relative to the expression of the actin gene in each sample. Ov, ovary; 5 and 15 days after anthesis; IG, immature green; MG, mature green; B, breaker stage. Hatched bars are the $Cwp^{HH}$ genotypes and solid bar is the $Cwp^{EE}$ genotypes.

Figure 6:
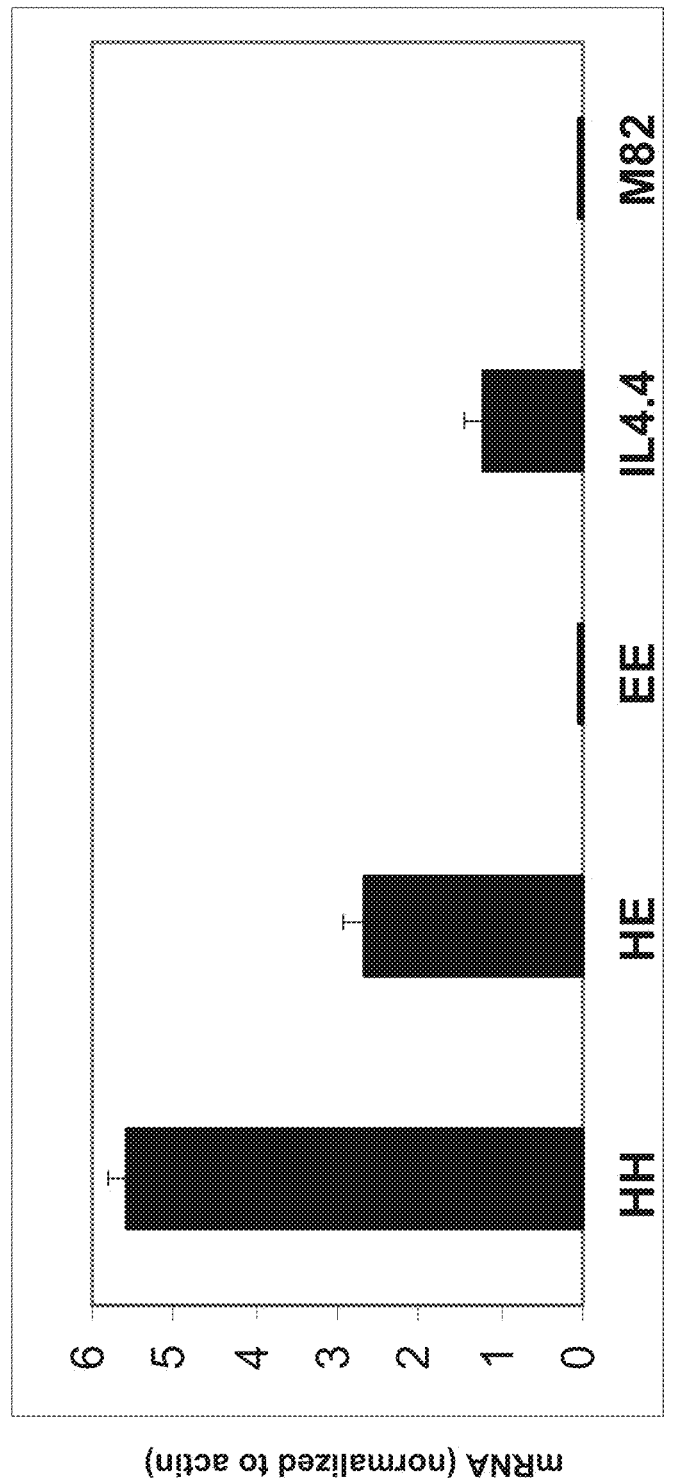

FIG. 6 is a graph showing expression analysis of the PUT gene in 15 day fruitlets of tomato genotypes. HH, $Cwp^{HH}$ genotype; HE, heterozygous $Cwp^{EE}$ genotype; EE, $Cwp^{EE}$ genotype. The three genotypes were selected from a segregating heterozygous population. IL4.4 represents the *L. pennellii* introgression line IL4.4 (Eshed and Zamir, 1985) which contains the *L. pennellii* homologue of PUT. M82 is the recurrent *L. esculentum* parent of the IL 4.4.

Figure 7A:
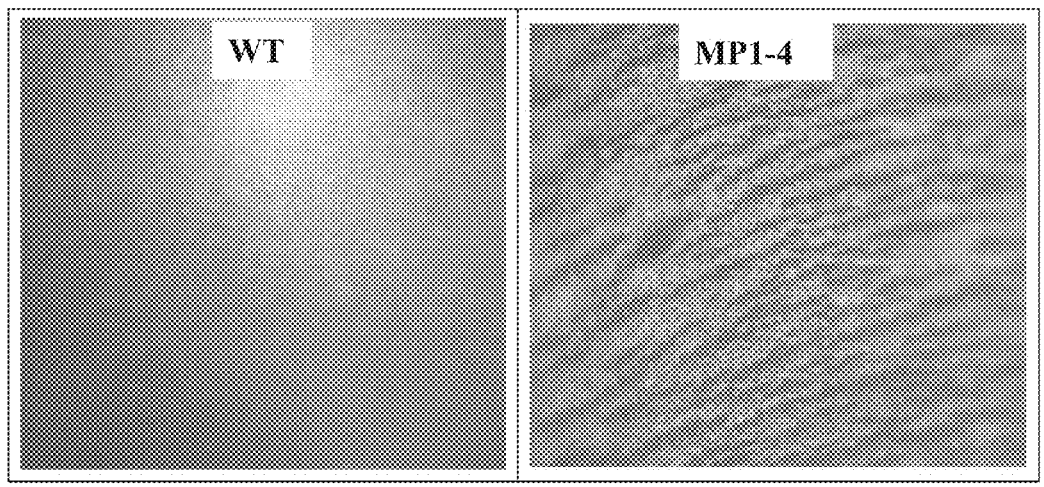
Figure 7B:
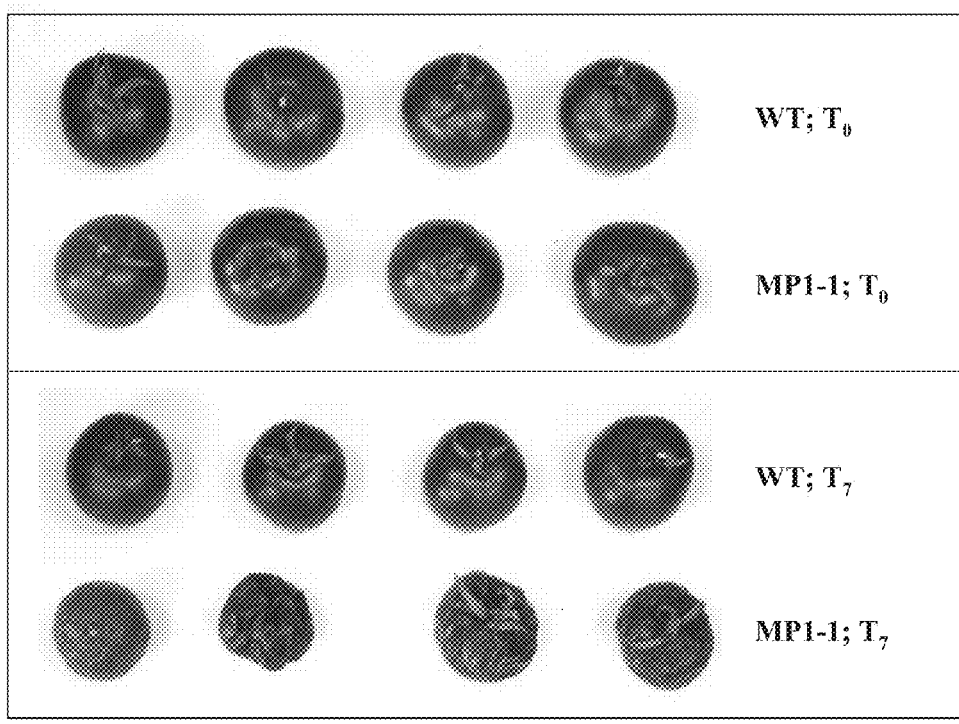

FIGS. 7a-b show transgenic tomato plants ($T_0$) expressing the PUT gene from the wild tomato species *Solanum habrochaites* S. (previously *Lycopersicon hirsutum* Mill.) under the 35S constitutive promoter. FIG. 7a shows binocular photographs presenting the intact surface of the fruit of the wild type MP1 tomato line (W.T.), and the micro-fissured transgenic fruit (Mp1-4). FIG. 7b show drying rate comparison between a wild type MP1 tomato line (W.T.) and another independent transgenic $T_0$ plant (MP 1-1). Fruit were picked-up at mature red developing stage and were placed at room temperature (15-25° C.). Pictures are from the beginning of the experiments ($T_0$) and after 7 days of drying ($T_7$).

FIGS. 8a-b show the effect of the PUT transgene copy number on micro-fissure severity (scale between 1 to 5, FIG. 8a) and weight loss percentage of the fruit (after 14 days at room temperature, FIG. 8b). Measurements were collected from 2 independent transgenic ($T_1$) segregating populations (16 individuals from each population). Each graph shows the mean (the horizontal line at the middle of each diamond), the 95% of confidence limit (the vertical edge of the diamond), and the scattering extent of individuals from each copy numbers group. The difference between groups is significant when base of one group triangle is not congruent to the triangle base of the other group. Statistics carried out by JMP program.

FIGS. 9a-b show a comparison between transgenic tomato individuals ($T_1$ generation) expressing no copies, analogous to wild type, and two copies of the PUT gene from the wild tomato species *Solanum habrochaites* S. FIG. 9a—Scanning electron micrograph presenting the intact surface of the fruit from an individual with no copies of the PUT gene (0 copies) and the micro-fissured fruit of an individual with two copies of the transgene. FIG. 9b—Drying rate comparison between an individual with no copies of the PUT gene (0 copies) and an individual with two copies (2 copies). Fruit were picked-up at mature red developing stage and were placed at room temperature (15-25° C.). Pictures are from the beginning of the experiments ($T_0$) and after 7 days of drying ($T_7$).

Figure 10A:
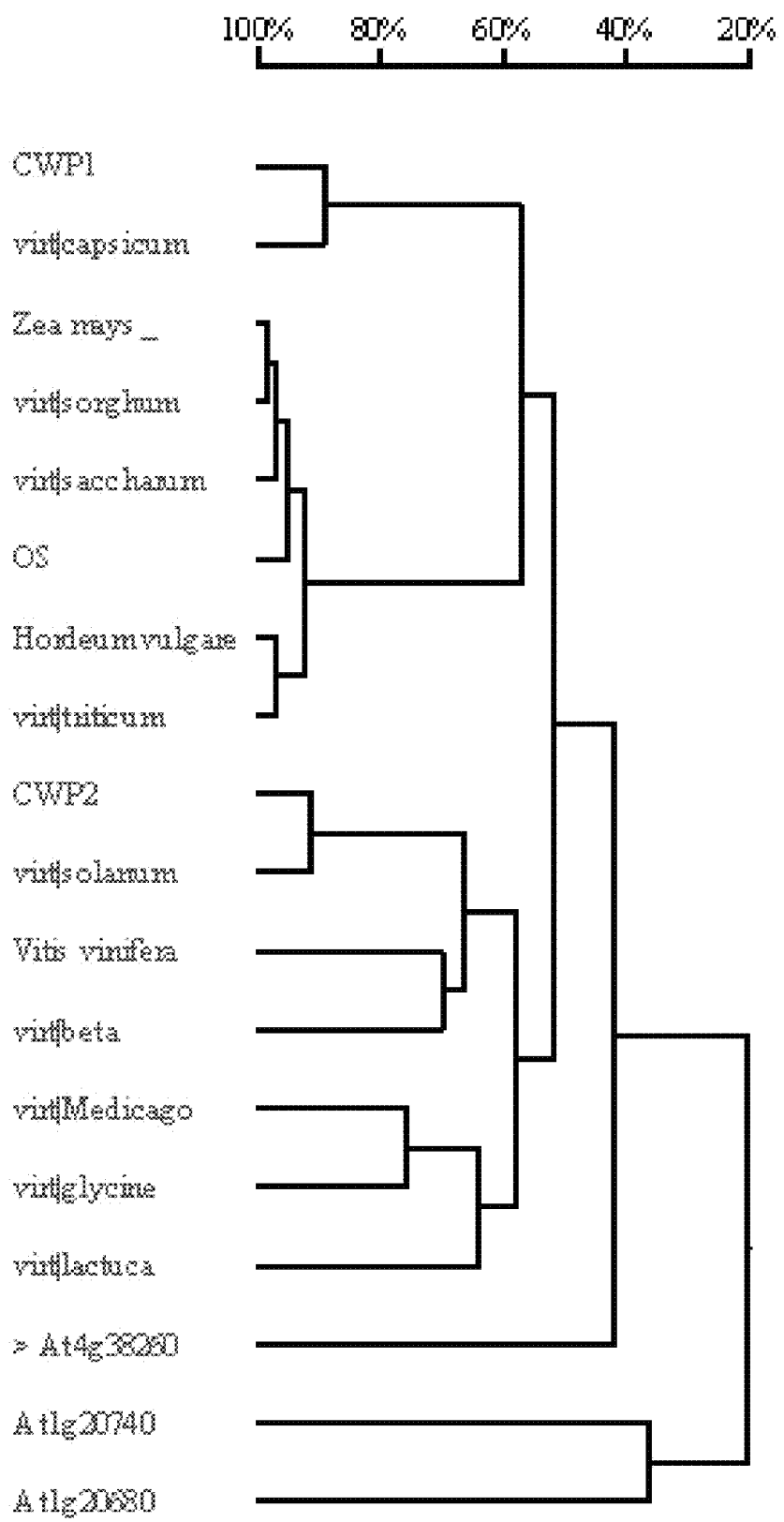
Figure 10B:
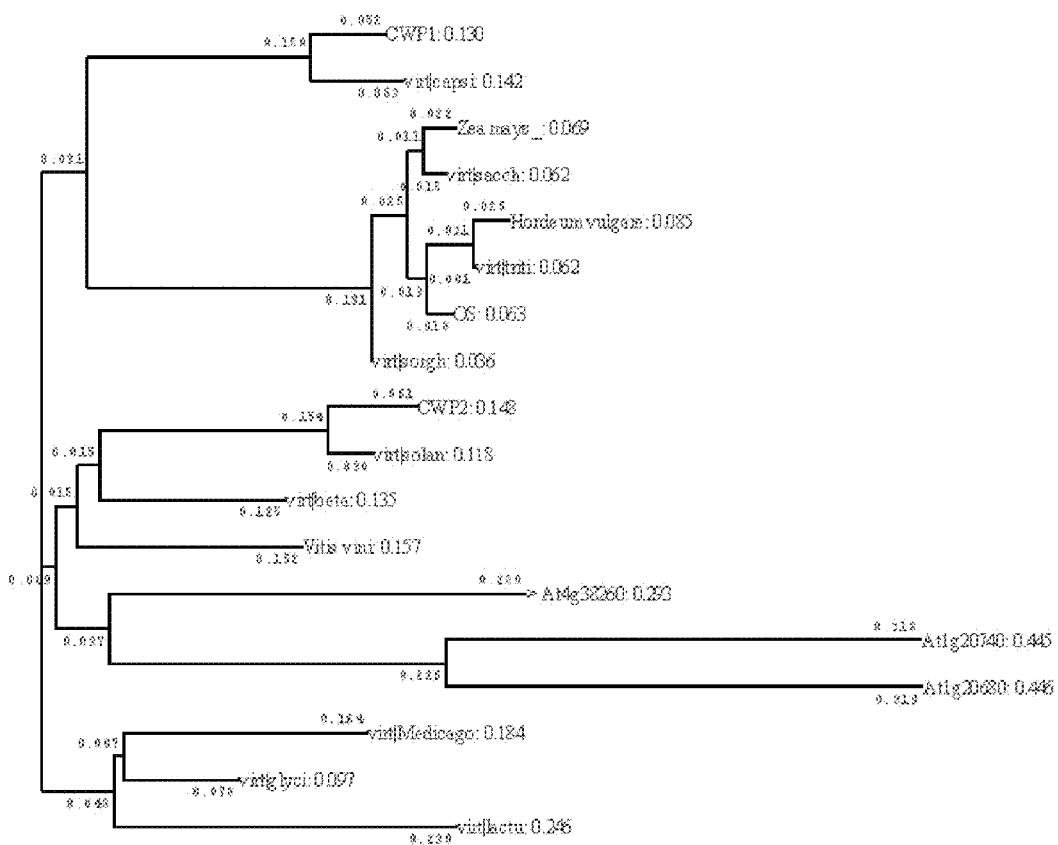

FIGS. 10a-b are dendrograms depicting conservation of CWP1 and CWP2 and related sequences from monocot and dicot species (SEQ ID NOs. 21, 24, 26, 28, 30, 32, 34, 36, 38, 40, 42, 44, 46, 48, 50, 52, 54 and 56). These sequences were retrieved from the EST TIGR database based on sequence homology to CWP1. Percentage homology to CWP1 is indicated above. FIG. 10a—conservation at the amino acid level. FIG. 10b—conservation at the nucleic acid level.

Figures 11, 11A:
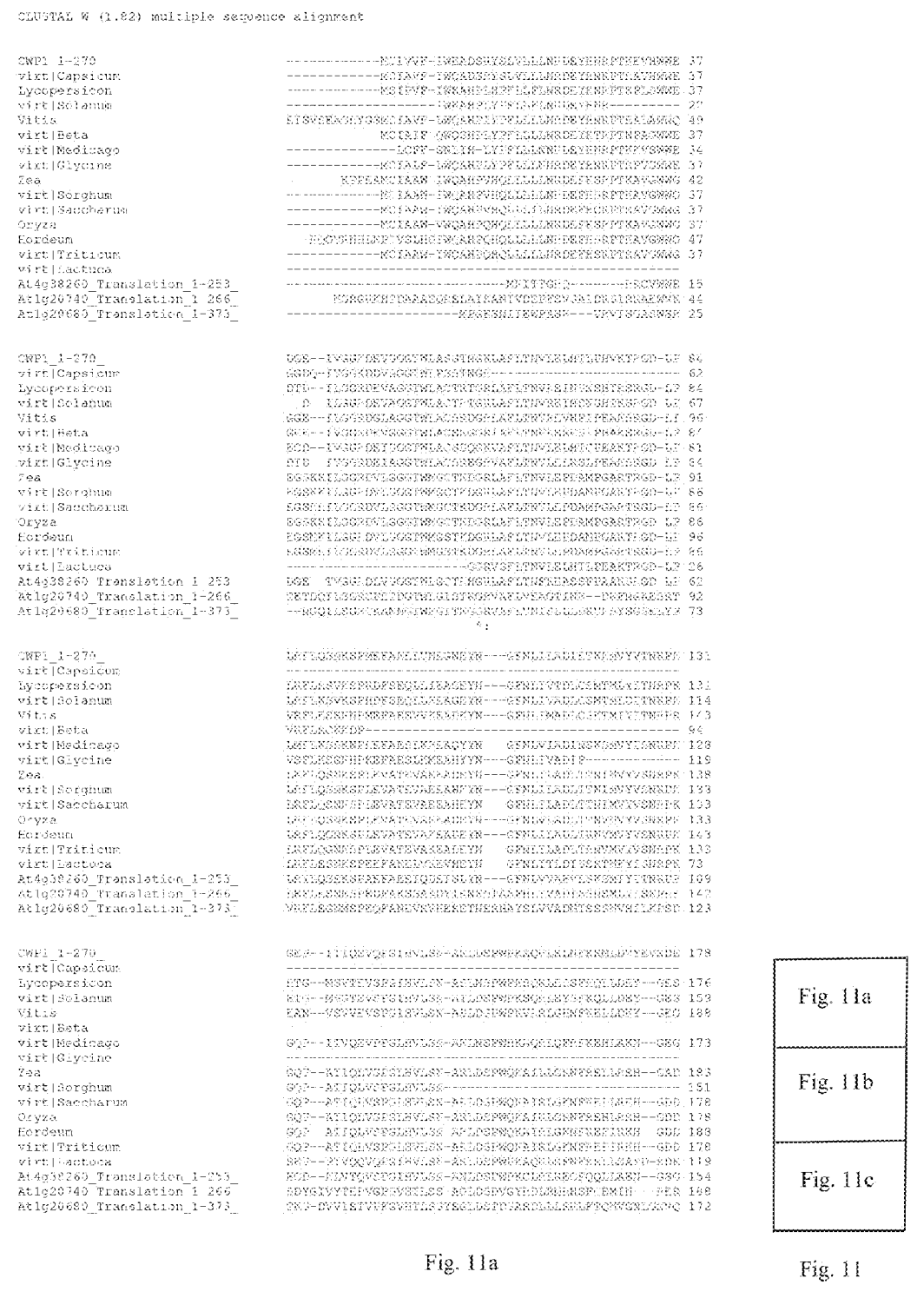
Figure 11B:
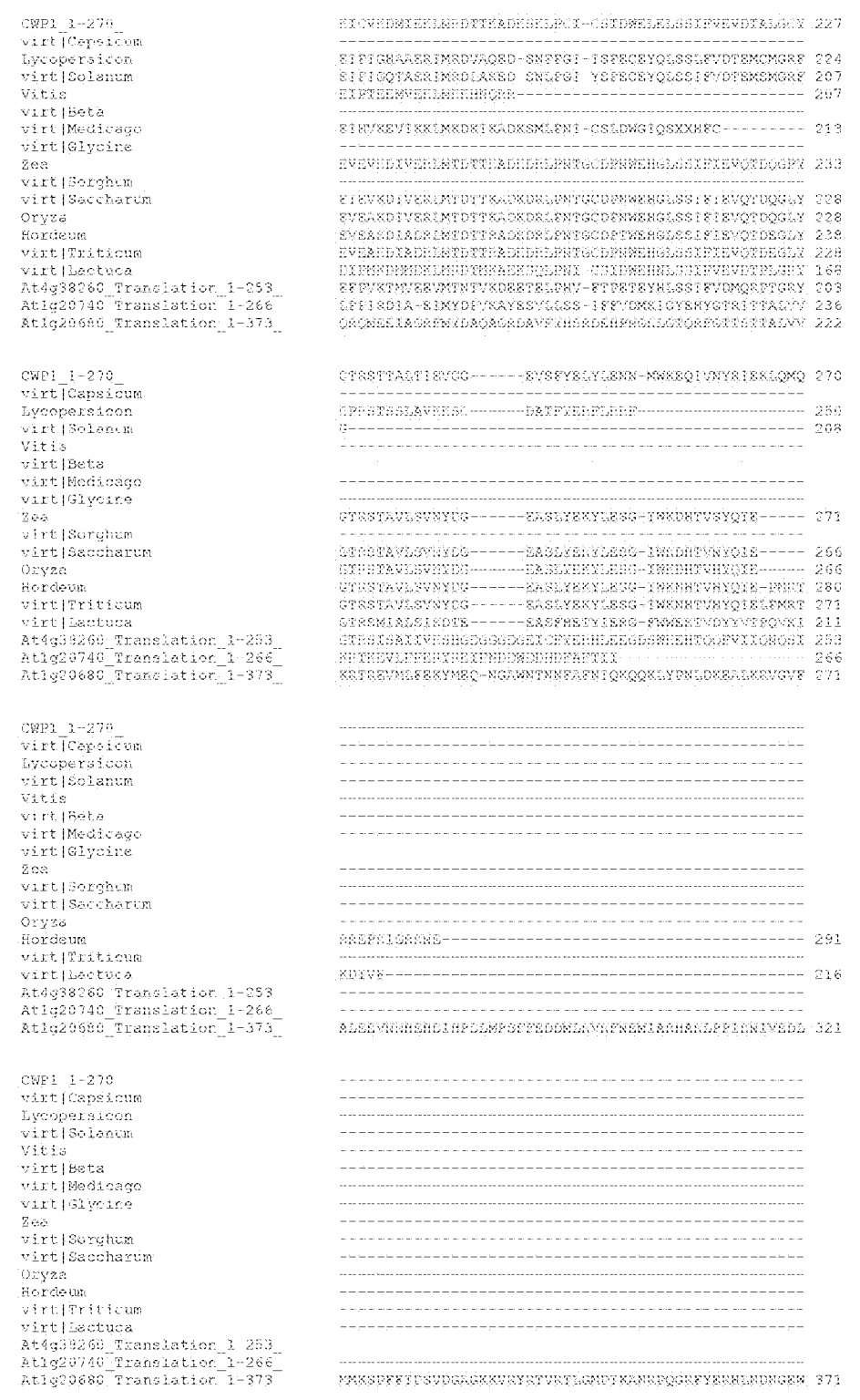

FIGS. 11a-c show multiple alignment between different protein members of the CWP1 family (SEQ ID NOs: 22, 25, 27, 29, 31, 33, 34, 37, 39, 41, 43, 45, 47, 49, 51, 53, 55 and 57) of the present invention generated by the ClustalW software of EMBL-EBI.

DESCRIPTION OF THE PREFERRED EMBODIMENTS

The present invention is of isolated polynucleotides and polypeptides which can be used for increasing cuticular water permeability of plants. Specifically, the present invention can be used to produce dehydrated fruit, such as tomato fruit.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The development of tomato varieties capable of being naturally dehydrated while still attached to the vine, without the accompaniment of degradative processes leading to fruit breakdown is highly valuable, to many fruit industries, such as the tomato industry.

PCT Publ. No. WO 01/13708 to Schaffer teaches the generation of dehydrated tomatoes having reduced cuticular water content using classical genetic breeding techniques (WO 01/13708). It is appreciated that the classical genetic breeding techniques are limiting to gene transfer within species or between closely related species of the same genus. Also, classical breeding is characterized by relatively large introgressions which include other undesirable genes closely linked to the gene of interest.

Introgressed cultivated tomato plants have been previously described by Eshed and Zamir (1985) having a genetic background (Introgression line IL4-4, i.e., resulting from an introgression extending from telomeric marker TG464 to centromeric marker CT50; ca20 cM) which may be associated with undesired traits. Similarly, Monforte et al. (2001) have described tomato plants having a similar genetic background derived from L. hirsutum (sub near introgression line (NIL) which spans from TG464 to CT173 (>10 cM). In the latter study the relatively large introgression is accompanied by undesirable horticultural traits, including traits of brix-yield, total yield, and fruit weight.

While reducing the present invention to practice the present inventors uncovered a single gene cwp1 (also termed put, used interchangeably herein) which is capable of increasing cuticular water permeability of a plant expressing same.

As is illustrated hereinbelow and in the Examples section which follows, the present inventors identified the inheritance pattern of the trait of fruit dehydration derived from L. hirsutum as a single major gene. Using a map-based positional cloning strategy, the present inventors cloned a gene from the wild tomato species L. hirsutum that increases the cuticular water permeability (CWP) of the mature red tomato fruit and leads to the dehydration of the intact fruit.

The present inventors showed that the wild species allele for cwp allows for expression of the gene in developing tomato fruit while the standard cultivated L. esculentum allele is not expressed and may be considered a null allele. They further showed that there is an allele dosage effect at the expression level and the heterozygous HE genotype is characterized by approximately half the expression as the homozygous genotype with two alleles from the wild species.

Bioinformatic analysis showed that cwp1 encodes a protein with no known biological function. This gene may contribute to breeding programs for new tomato products, as well as for other crops, as it controls water loss through the cuticle. Furthermore, the structural phenotype of microfissures associated with this gene indicates a role for cwp in fruit cuticle development. Expression of cwp1 gene under the 35S promoter in cultivated tomato induced the formation of microfissures in the expanding fruit, supporting the suggested role of this gene in regulation of cuticular water permeability. Southern blot analysis uncovered an additional tomato homolog cwp2. Interestingly, this homologue maps to tomato chromosome 2-1 where there is a reported QTL for tomato fruit epidermal reticulation (Frary et al, 2004). Developing fruit of the solanaceous cultivated pepper (Capsicum annum) also express a cwp homologue highly similar (87%) to the Lecwp1 gene in its epidermal tissue and pepper fruit are characterized by the horticultural problem of post-harvest water loss, as well as by the desirable trait of fruit dehydration in paprika cultivars. Therefore it is likely that homologues of the CWP gene may also contribute to cuticular modification and water permeability.

These results indicate that the expression of the cwp gene leads to a structurally modified cuticle (based on weight and TEM) which presumably undergoes fissuring during fruit expansion due to reduction in elasticity. However, this phenomenon is observed only in fruit with a highly developed fruit cuticle such as the astomatous thick skinned cultivated tomato and is not apparent in fruit of the wild species, with their characteristic thinner cuticle. The deposition of cuticular components during cultivated tomato fruit development undergoes a surge during the transition from the immature to the mature green stage (Baker, 1982) and it is reasonable that this coincides with the observation of the microfissure phenotype.

Without being bound by theory, it is suggested that the genetic trait of a relatively impervious fruit cuticle was a positive development in the evolution and domestication process of cultivated tomatoes, allowing for the stability of the ripening and harvested fruit. The genetic control of the trait of dehydration indicates a selection procedure for the null Cwp at some stage of evolution and domestication of the crop.

Phylogenetic analysis (FIGS. 10a-b) indicates that the CWP genes of the present invention belong to a larger family of genes, which may be used for controlling cuticular water permeability in a broad range of crop plants.

Thus, according to one aspect of the present invention there is provided an isolated polynucleotide comprising a nucleic acid sequence encoding a polypeptide having an amino acid sequence at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% homologous to SEQ ID NO: 22, the polypeptide being capable of increasing a cuticular water permeability of a plant expressing same.

As used herein the phrase "cuticular water permeability" refers to the ability of the cuticle to inhibit water evaporation from a cuticle-surrounded plant tissue (aerial tissues of the plant), such as the fruit. It is appreciated that increased cuticular water permeability will result in dehydration of the cuticle surrounded tissue, as a result of enhanced evaporation.

As used herein the phrase "increasing cuticular water permeability" refers to at least about 5%, at least about 10%, at least about 15%, at least about 20%, at least about 30%, at least about 40%, at least about 50%, increase in cuticular water permeability as compared to plants of similar parental cultivar or genotype not expressing same.

Methods of determining cuticular water permeability are well known in the art and described in length in the Examples section which follows (e.g. fissure severity and weight loss percentage of the fruit. See Example 5 of the Examples section which follows. In addition, methods for measuring cuticular water permeability also include, but are not limited to, measurements of water diffusion across isolated fruit skin, measurement of polar pore size and hydrodynamic permeability (Schönherr, 1976). These functional assays together with the structural guidelines provided herein, allow the identification of functional homologs for the polynucleotides and polypeptides of the present invention.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

As used herein the phrase "an isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to one preferred embodiment of this aspect of the present invention, the nucleic acid sequence of the above-described isolated polynucleotide of the present invention is as set forth in SEQ ID NO: 21, 23, 24, 26, 28, 30, 32, 34, 36, 38, 40, 42, 44, 46, 48, 50, 52, 54 or 56.

According to another preferred embodiment of this aspect of the present invention, the amino acid sequence of the encoded polypeptide of the present invention is as set forth in SEQ ID NO: 22, 25, 27, 29, 31, 33, 35, 37, 39, 41, 43, 45, 47, 49, 51, 53, 55 or 57.

The isolated polynucleotides of this aspect of the present invention can be qualified using a hybridization assay by incubating the isolated polynucleotides described above in the presence of oligonucleotide probe or primer under moderate to stringent hybridization conditions.

As used herein the term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with polynucleotide sequences of the present invention.

Moderate to stringent hybridization conditions are characterized by a hybridization solution such as containing 10% dextrane sulfate, 1 M NaCl, 1% SDS and 5×10$^6$ cpm $^{32}$P labeled probe, at 65° C., with a final wash solution of 0.2×SSC and 0.1% SDS and final wash at 65° C. and whereas moderate hybridization is effected using a hybridization solution containing 10% dextrane sulfate, 1 M NaCl, 1% SDS and 5×10$^6$ cpm $^{32}$P labeled probe, at 65° C., with a final wash solution of 1×SSC and 0.1% SDS and final wash at 50° C.

Using hybridization methodology, the present inventors were able to isolate cwp2, another tomato homolog of cwp1, which is mapped to a reported QTL for tomato fruit epidermal reticulation (Frary et al, 2004), supporting its role in cuticular water permeability.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel polypeptides or portions thereof, which are encoded by the isolated polynucleotides and respective nucleic acid fragments thereof described hereinabove.

Thus, the present invention also encompasses polypeptides encoded by the polynucleotide sequences of the present invention. The amino acid sequences of these novel polypeptides are set forth in SEQ ID NO: 22, 25, 27, 29, 31, 33, 35, 37, 39, 41, 43, 45, 47, 49, 51, 53, 55 or 57.

The present invention also encompasses homologues of these polypeptides, such homologues can be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO: 22.

The present invention also encompasses fragments of the above described polypeptides and polypeptides having mutations, such as deletions, insertions or substitutions of one or more amino acids, either naturally occurring or man induced, either randomly or in a targeted fashion.

Amino acid sequence information of the polypeptides of the present invention can be used to generate antibodies, which specifically bind to the polypeptides of the present invention. For example, such antibodies can be directed to amino acid sequence coordinates 55-160 of SEQ ID NO: 22. Sequence coordinates 55-160 include the majority of conserved sequences and motifs of the multiple comparison analysis (FIG. 11). Due to high sequence homology in this amino acid sequence region, such antibodies are expected to be cross-reactive to the various polypeptides the present invention (e.g., SEQ ID NOs. 22, 25, 27, 29, 31, 33, 35, 37, 39, 41, 43, 45, 47, 49, 51, 53, 55 and 57).

Polynucleotide and polypeptide sequences of the present invention can be used to generate plants with increased cuticular water permeability.

For example, genetically modified plants can be generated by expressing in the plant an isolated polynucleotide of the present invention.

As used herein the term "plant" refers to a crop plant (whole plant or a portion thereof, e.g., fruit, seed) such as a monocot or dicot crop plant, as well as other plants coniferous plants, moss or algae, in which increased cuticular water permeability is commercially desired. Preferably, the plant of the present invention produces fruits which dehydration is of commercial value. Examples of such plants include, but are not limited, to tomato, grapes, pepper, apples, peach, apricot, dates, figs, eggplants, onion, strawberries, cucurbits, hay plants, forage plants, spice plants, herb plants and others.

To express exogenous polynucleotides in plant cells, a polynucleotide sequence of the present invention is preferably ligated into a nucleic acid construct suitable for plant cell expression. Such a nucleic acid construct includes a cis-acting regulatory region such as a promoter sequence for directing transcription of the polynucleotide sequence in the cell in a constitutive or inducible manner. The promoter may be homologous or heterologous to the transformed plant/cell.

Preferred promoter sequences which can be used in accordance with this aspect of the present invention are fruit specific or seed specific promoters.

For example, the novel promoter sequence of the cwp1 gene (or functional fragments thereof) may be preferably used in the nucleic acid constructs of the present invention (SEQ ID NO: 58).

Other examples of fruit specific promoters are described in U.S. Pat. No. 4,943,674.

Other promoters which can be used in accordance with this aspect of the present invention are those that ensure expression only in specified aerial exposed organs of the plant, such as the leaf, tuber, seed, stem, flower or specified cell types such as parenchyma, epidermal, trichome or vascular cells.

Preferred promoters enhancing expression in seeds include the phas promoter (Geest et al., Plant Mol. Biol. 32:579-588 (1996)); the GluB-1 promoter (Takaiwa et al., Plant Mol. Biol. 30:1207-1221 (1996)); the gamma-zein promoter (Torrent et al. Plant Mol. Biol. 34:139-149 (1997)), and the oleosin promoter (Sarmiento et al., The Plant Journal 11:783-796 (1997)).

Other promoter sequences which mediate constitutive, inducible, tissue-specific or developmental stage-specific expression are disclosed in WO 2004/081173.

The nucleic acid construct can be, for example, a plasmid, a bacmid, a phagemid, a cosmid, a phage, a virus or an artificial chromosome. Preferably, the nucleic acid construct of the present invention is a plasmid vector, more preferably a binary vector.

The phrase "binary vector" refers to an expression vector which carries a modified T-region from Ti plasmid, enable to be multiplied both in $E.\ coli$ and in $Agrobacterium$ cells, and usually comprising reporter gene(s) for plant transformation between the two boarder regions. A binary vector suitable for the present invention includes pBI2113, pBI121, pGA482, pGAH, pBIG, pBI101 (Clonetech), pPI, and pBIN PLUS (see Example 5 of the Examples section which follows) or modifications thereof.

The nucleic acid construct of the present invention can be utilized to transform a host cell (e.g., bacterial, plant) or plant.

As used herein, the terms "transgenic" or "transformed" are used interchangeably referring to a cell or a plant into which cloned genetic material has been transferred.

In stable transformation, the nucleic acid molecule of the present invention is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants (Potrykus, I. (1991). Annu Rev Plant Physiol Plant Mol Biol 42, 205-225; Shimamoto, K. et al. (1989). Fertile transgenic rice plants regenerated from transformed protoplasts. Nature (1989) 338, 274-276).

The principal methods of the stable integration of exogenous DNA into plant genomic DNA includes two main approaches:

(i) *Agrobacterium*-Mediated Gene Transfer.

See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Calif.; and Gatenby, A. A. (1989). Regulation and Expression of Plant Genes in Microorganisms, pp. 93-112, Plant Biotechnology, S. Kung and C. J. Arntzen, eds., Butterworth Publishers, Boston, Mass.

(ii) Direct DNA Uptake.

See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Calif.; and Toriyama, K. et al. (1988). Bio/Technol 6, 1072-1074 (methods for direct uptake of DNA into protoplasts). See also: Zhang et al. (1988). Plant Cell Rep 7, 379-384; and Fromm, M. E. et al. (1986). Stable transformation of maize after gene transfer by electroporation. Nature 319, 791-793 (DNA uptake induced by brief electric shock of plant cells). See also: Klein et al. (1988). Bio/Technology 6, 559-563; McCabe, D. E. et al. (1988). Stable transformation of soybean (*Glycine max*) by particle acceleration. Bio/Technology 6, 923-926; and Sanford, J. C. (1990). Biolistic plant transformation. Physiol Plant 79, 206-209 (DNA injection into plant cells or tissues by particle bombardment). See also: Neuhaus, J. M. et al. (1987). Theor Appl Genet 75, 30-36; and Neuhaus, J. M. and Spangenberg, G. C. (1990). Physiol Plant 79, 213-217 (use of micropipette systems). See U.S. Pat. No. 5,464,765 (glass fibers or silicon carbide whisker transformation of cell cultures, embryos or callus tissue). See also: DeWet, J. M. J. et al. (1985). "Exogenous gene transfer in maize (*Zea mays*) using DNA-treated pollen," Experimental Manipulation of Ovule Tissue, G. P. Chapman et al., eds., Longman, New York-London, pp. 197-209; and Ohta, Y. (1986). High-Efficiency Genetic Transformation of Maize by a Mixture of Pollen and Exogenous DNA. Proc Natl Acad Sci USA 83, 715-719 (direct incubation of DNA with germinating pollen).

The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch, R. B. et al. (1988). "Leaf disc transformation." Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful for in the creation of transgenic dicotyledenous plants.

There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

Following stable transformation, plant propagation occurs. The most common method of plant propagation is by seed. The disadvantage of regeneration by seed propagation, however, is the lack of uniformity in the crop due to heterozygosity, since seeds are produced by plants according to the genetic variances governed by Mendelian rules. In other words, each seed is genetically different and each will grow with its own specific traits. Therefore, it is preferred that the regeneration be effected such that the regenerated plant has identical traits and characteristics to those of the parent transgenic plant. The preferred method of regenerating a transformed plant is by micropropagation, which provides a rapid, consistent reproduction of the transformed plants.

Micropropagation is a process of growing second-generation plants from a single tissue sample excised from a selected parent plant or cultivar. This process permits the mass reproduction of plants having the preferred tissue and expressing a fusion protein. The newly generated plants are genetically identical to, and have all of the characteristics of, the original plant. Micropropagation allows for mass production of quality plant material in a short period of time and offers a rapid multiplication of selected cultivars with preservation of the characteristics of the original transgenic or transformed plant. The advantages of this method of plant cloning include the speed of plant multiplication and the quality and uniformity of the plants produced.

Micropropagation is a multi-stage procedure that requires alteration of culture medium or growth conditions between stages. The micropropagation process involves four basic stages: stage one, initial tissue culturing; stage two, tissue culture multiplication; stage three, differentiation and plant formation; and stage four, greenhouse culturing and hardening. During stage one, the tissue culture is established and certified contaminant-free. During stage two, the initial tissue culture is multiplied until a sufficient number of tissue samples are produced to meet production goals. During stage three, the newly grown tissue samples are divided and grown into individual plantlets. At stage four, the transformed plantlets are transferred to a greenhouse for hardening where the plants' tolerance to light is gradually increased so that they can continue to grow in the natural environment.

Transient transformation can be effected by any of the direct DNA transfer methods described above or by viral infection using modified plant viruses.

Viruses that have been shown to be useful for the transformation of plant hosts include cauliflower mosaic virus (CaMV), tobacco mosaic virus (TMV), and baculovirus (BV). Transformation of plants using plant viruses is described in, for example: U.S. Pat. No. 4,855,237 (bean golden mosaic virus, BGMV); EPA 67,553 (TMV); Japanese Published Application No. 63-14693 (TMV); EPA 194,809 (BV); EPA 278,667 (BV); and Gluzman, Y. et al. (1988). Communications in Molecular Biology: Viral Vectors, Cold Spring Harbor Laboratory, New York, pp. 172-189. The use of pseudovirus particles in expressing foreign DNA in many hosts, including plants, is described in WO 87/06261.

Construction of plant RNA viruses for the introduction and expression of non-viral exogenous nucleic acid sequences in plants is demonstrated by the above references as well as by: Dawson, W. O. et al. (1989). A tobacco mosaic virus-hybrid expresses and loses an added gene. Virology 172, 285-292; French, R. et al. (1986) Science 231, 1294-1297; and Takamatsu, N. et al. (1990). Production of enkephalin in tobacco protoplasts using tobacco mosaic virus RNA vector. FEBS Lett 269, 73-76.

If the transforming virus is a DNA virus, one skilled in the art may make suitable modifications to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of the DNA will produce the coat protein, which will encapsidate the viral DNA. If the virus is an RNA virus, the virus is generally cloned as a cDNA and inserted into a plasmid. The plasmid is then used to make all of the plant genetic constructs. The RNA virus is then transcribed from the viral sequence of the plasmid, followed by translation of the viral genes to produce the coat proteins which encapsidate the viral RNA.

Construction of plant RNA viruses for the introduction and expression in plants of non-viral exogenous nucleic acid sequences, such as those included in the construct of the present invention, is demonstrated in the above references as well as in U.S. Pat. No. 5,316,931.

In one embodiment, there is provided for insertion a plant viral nucleic acid, comprising a deletion of the native coat protein coding sequence from the viral nucleic acid, a non-native (foreign) plant viral coat protein coding sequence, and a non-native promoter, preferably the subgenomic promoter of the non-native coat protein coding sequence, and capable of expression in the plant host, packaging of the recombinant plant viral nucleic acid, and ensuring a systemic infection of the host by the recombinant plant viral nucleic acid. Alternatively, the native coat protein coding sequence may be made non-transcribable by insertion of the non-native nucleic acid sequence within it, such that a non-native protein is produced. The recombinant plant viral nucleic acid construct may contain one or more additional non-native subgenomic promoters. Each non-native subgenomic promoter is capable of transcribing or expressing adjacent genes or nucleic acid sequences in the plant host and incapable of recombination with each other and with native subgenomic promoters. In addition, the recombinant plant viral nucleic acid construct may contain one or more cis-acting regulatory elements, such as enhancers, which bind a trans-acting regulator and regulate the transcription of a coding sequence located downstream thereto. Non-native nucleic acid sequences may be inserted adjacent to the native plant viral subgenomic promoter or the native and non-native plant viral subgenomic promoters if more than one nucleic acid sequence is included. The non-native nucleic acid sequences are transcribed or expressed in the host plant under control of the subgenomic promoter(s) to produce the desired products.

In a second embodiment, a recombinant plant viral nucleic acid construct is provided as in the first embodiment except that the native coat protein coding sequence is placed adjacent to one of the non-native coat protein subgenomic promoters instead of adjacent to a non-native coat protein coding sequence.

In a third embodiment, a recombinant plant viral nucleic acid construct is provided comprising a native coat protein gene placed adjacent to its subgenomic promoter and one or more non-native subgenomic promoters inserted into the viral nucleic acid construct. The inserted non-native subgenomic promoters are capable of transcribing or expressing adjacent genes in a plant host and are incapable of recombination with each other and with native subgenomic promoters. Non-native nucleic acid sequences may be inserted adjacent to the non-native subgenomic plant viral promoters such that said sequences are transcribed or expressed in the host plant under control of the subgenomic promoters to produce the desired product.

In a fourth embodiment, a recombinant plant viral nucleic acid construct is provided as in the third embodiment except that the native coat protein coding sequence is replaced by a non-native coat protein coding sequence.

Viral vectors are encapsidated by expressed coat proteins encoded by recombinant plant viral nucleic acid constructs as described hereinabove, to produce a recombinant plant virus. The recombinant plant viral nucleic acid construct or recombinant plant virus is used to infect appropriate host plants. The recombinant plant viral nucleic acid construct is capable of replication in a host, systemic spread within the host, and transcription or expression of one or more foreign genes (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced into the cells preferably via particle bombardment, with the aim of introducing at least one exogenous nucleic acid molecule into the chloroplasts. The exogenous nucleic acid is selected by one ordinarily skilled in the art to be capable of integration into the chloroplast's genome via homologous recombination, which is readily effected by enzymes inherent to the chloroplast. To this end, the exogenous nucleic acid comprises, in addition to a gene of interest, at least one nucleic acid sequence derived from the chloroplast's genome. In addition, the exogenous nucleic acid comprises a selectable marker, which by sequential selection procedures serves to allow an artisan to ascertain that all or substantially all copies of the chloroplast genome following such selection include the exogenous nucleic acid. Further details relating to this technique are found in U.S. Pat. Nos. 4,945,050 and 5,693,507, which are incorporated herein by reference. A polypeptide can thus be produced by the protein expression system of the chloroplast and become integrated into the chloroplast's inner membrane.

A number of approaches are known in the art to minimize gene flow among crops and weeds. Following is a non-limiting description of such approaches [see also U.S. Pat. Appl. Nos. 20040098760, 20040172678 and Daniell (2002) Nat. Biotech. 20:581]. Other approaches include male and/or seed sterility (which prevent outcrossing, volunteer seed dispersal), cleistogamy (in which pollination occurs prior to flower opening to thereby prevent outcrossing) and apomixis (seed is from vegetative origin and not from sexual cross, which controls outcrosssing and volunteer seed dispersal. See U.S. Pat. No. 6,825,397).

Maternal Inheritance

Maternal inheritance of cytoplasmic organelles is shared by plant (chloroplasts) and animal (mitochondria) systems. Several explanations have been offered to explain this phenomenon. It promotes the invasion of a population by selfish cytoplasmic factors that are overrepresented within an individual[1]. In addition, maternal inheritance of cytoplasmic factors is an evolutionary mechanism to prevent sexual transmission of disorders or pathogens associated with males; only the nucleus (not cytoplasm) is allowed to penetrate the ovule during fertilization [Gressel J. *Molecular Biology in Weed Control* (Taylor and Francis, London, 2002)]. It may also be an extension of the general suppression of male nuclear genes that takes place in plants after fertilization [Avni *Mol. Gen. Genet.* 225, 273-277 (1991)].

The use of chloroplast genetic engineering to promote maternal inheritance of transgenes is highly desirable in those instances involving a potential for outcross among genetically modified crops or between genetically modified crops and weeds. The prevalent pattern of plastid inheritance found in the majority of angiosperms is uniparental-maternal and chloroplast genomes are maternally inherited in most crops.

Maternal inheritance of the chloroplast genome is achieved in plants during the development of the generative cells that form sperm cells, which then fuse with the female gametes during fertilization. The generative cells are the result of unequal divisions during pollen formation and do not receive any chloroplasts [Hagemann *Protoplasma* 152, 57-64 (1989)].

Maternal inheritance of transgenes and prevention of gene flow through pollen in chloroplast transgenic plants have been successfully demonstrated in several plant species, including tobacco and tomato [Daniell *Nat. Biotechnol.* 16, 345-348; Ruf *Nat. Biotechnol.* 19, 870-875 (2001)]. Although chloroplast genomes of several other plant species, including potato, have been transformed, maternal inheritance has not been demonstrated in these studies. However, more than 30 transgenes have been stably integrated into chloroplast genomes to confer desired plant traits or for the use of transgenic chloroplasts as biofactories to produce functional biopharmaceuticals or edible vaccines or biopolymers [Daniell *Trends Plant Sci.* 7, 84-91 (2001); Daniell *Curr. Opin. Biotechnol.* 13, 136-141].

Unlike many other containment strategies, the maternal inheritance approach has already been tested in the field. Scott and Wilkinson [*Nat. Biotechnol.* 17, 390-392 (1999)] studied plastid inheritance in natural hybrids collected from two wild populations growing next to oilseed rape along 34 km of the Thames River in the United Kingdom and assessed the persistence of 18 feral oilseed rape populations over a period of three years. They analyzed several variables that would influence the movement of chloroplast genes from crops to wild relatives, including the mode of inheritance of plastids and incidence of sympatry (the occurrence of species together in the same area), to quantify opportunities for forming mixed populations and persistence of crops outside agriculture limits for introgression. Despite some 0.6-0.7% sympatry between the crop and weed species, mixed stands showed a strong tendency toward rapid decline in plant number, seed return, and ultimately extinction within three years. Thus, Scott and Wilkinson concluded that gene flow should be rare if plants are genetically engineered via the chloroplast genome.

Thus, maternal inheritance of chloroplast genomes is a promising option for gene containment. Although plastid transformation remains to be achieved in several major crop species, chloroplast genetic engineering has now been shown to confer resistance to herbicides [Daniell *Nat. Biotechnol.* 16, 345-348 (1998)], insects, disease [DeGray *Plant Physiol.* 127, 852-862 (2000)], and drought, as well as to produce antibodies [Daniell *Trends Plant Sci.* 7, 84-91 (2000)], biopharmaceuticals [Daniell *Trends Plant Sci.* 7, 84-91 (2000)], and edible vaccines. A recent report from the European Environment Agency (Copenhagen, Denmark) recommends chloroplast genetic engineering as a gene-containment approach [Eastham Genetically Modified Organisms (GMOs): The Significance of Gene Flow Through Pollen Transfer. Environmental Issue Report 28 (European Environmental Agency, Copenhagen, Denmark, 2002)].

Genome Incompatability—

Many cultivated crops have multiple genomes. Only one of these crop genomes is compatible for interspecific hybridization with weeds. For example, the D genome of wheat is compatible with the D genome of *Aegilops cylindrica* (bearded goatgrass), a problem weed in the United States; in contrast, it would be much harder to achieve interspecific hybridization of the weed with durum wheat, which has an AABB tetraploid B genome [Gressel. *Molecular Biology* in Weed Control (Taylor and Francis, London, 2002)] provided ploidy level is not an issue. Similarly, there is possibility for gene transfer from the B genome of *Brassica juncea* (Indian or brown mustard) to many *Brassica* weeds with wild species; however, thus far most genetic engineering has been carried out *Brassica napus*, which has the AACC tetraploid genome and is thus unlikely to be compatible. The risk of transgenic traits spreading into weeds can be reduced drastically by releasing only those transgenic lines with incompatible genomes.

With the availability of genome information, it might become possible to engineer crops that have a reduced likelihood of outcrossing with weeds through incompatibility mechanisms.

Temporal and Tissue-Specific Control—

Chemically inducible promoters may be used for gene containment strategies. For example, a chemical could be used to induce transient expression of a gene conferring herbicide resistance before a field is sprayed with herbicide. Clearly, genetic isolation may be possible by restricting expression of a foreign gene to those times when the crop is not flowering. Such promoters are currently available (see ref. WO 97/06269).

An alternative approach to switching on a foreign gene only when a crop is not in flower would be physically to remove the gene before flowering occurs. Keenan and Stemmer [*Nat. Biotechnol.* 20, 215-216 (2002)] suggest that this can be achieved by using chemically inducible or fruit-specific promoters to activate expression of a site-specific recombinase, such as Cre, that would excise a foreign gene before flowering. Such systems can induce Cre expression and result in the removal of a gene flanked by two lox sites in either the seed (using a seed-specific promoter) or the entire plant (using a chemically inducible promoter).

Transgenic Mitigation—

Another approach for containing gene spread would be to compromise the fitness of weeds that by introgression have acquired positive survival traits from crop genes [Gressel *Trends Biotechnol.* 17, 361-366 (1999)]. This approach, termed transgenic mitigation (TM), is based on the premises that (1) tandem constructs act as tightly linked genes, and their segregation from each other is exceedingly rare; (2) TM traits are neutral or positive for crops, but deleterious for weeds; and (3) even mildly harmful TM traits will be eliminated from weed populations because such plants compete strongly among themselves and have a large seed output. Examples of processes that might be targeted by TM include seed dormancy, seed ripening and shattering, and growth.

Weed seeds typically exhibit secondary dormancy, with those from one harvest germinating throughout the following season and in subsequent years, thereby maximizing fitness (and preventing all weeds from being controlled by single treatments) while reducing sibling competition. Abolition of secondary dormancy is neutral to the crop, but deleterious to weeds. Steber et al. have identified an *Arabidopsis* mutant that is insensitive to abscisic acid and totally lacks secondary dormancy. Such genes associated with dormancy (engineered or mutated) may be used for TM [*Genetics* 149, 509-521 (1998)].

Another characteristic of weedy plants is that they disperse their seeds over a period of time, and most of their ripe seeds shatter to the ground, ensuring continuity. As a result, uniformly ripening and anti-shattering genes are harmful to weeds but neutral for crops, whose seeds ripen uniformly and do not easily shatter; in fact, anti-shattering genes are even advantageous for oilseed rape, which still has shattering and volunteer weed problems. Only weed-free "certified" seed is sown, thereby eliminating transgenic weed seed. It is thought that the changing hormone balance in the abscission zone of a seed influences shattering propensity. Cytokinin overproduction may delay shattering. A SHATTERPROOF gene has been recently isolated from *Arabidopsis* that prevents seed shattering by delaying valve opening on the silique. This may be an ideal strategy for the closely related oilseed rape.

Dwarfing has been especially valuable in generating "green revolution" varieties of rice and wheat and brought self-sufficiency to India and China. However, the dwarfing trait is disadvantageous for weeds, because they can no longer compete with the crop for light. Genetically engineered height reduction is possible by preventing biosynthesis of gibberellins33. In addition, a defective gibberellic acid receptor gene has been isolated that confers gibberellin instability by competing with the native receptor, thereby inducing dwarfing.

Promoter sequence information (e.g., SEQ ID NO: 58) allows the generation of plants with increased expression of the polypeptides of the present invention by modifying the promoter sequence of the cultivated plant. Thus for instance, "knocking in" technology or mutagenesis (e.g., chemical or radiation), can be used to directly or indirectly generate plants with up-regulated expression of the polypeptides of the present invention.

It will be appreciated that by localizing the cwp1 gene of the present invention to tomato chromosome 4 of wild *Lycopersicon* spp. and finer mapping to an introgression smaller than a chromosomal fraction extending from telomeric marker TG464 to centromeric marker CT173, it is possible to generate cultivated tomato plants with increased cuticular water permeability using classical breeding techniques.

For example, *Lycopersicon esculentum* plant may be hybridized with wild *Lycopersicon* spp. plant. The fruits of the *Lycopersicon esculentum* plants are then allowed to ripen and the hybrid (F1) seeds are collected. The collected F1 seeds are then planted and F1 plants are grown and allowed to self-pollinate. Selfing may be continued for at least one additional generation or the F1 plants may be crossed to *esculentum* parental plant. Fruits from selfed or backcrossed generations are allowed to remain on the vine past the point of formal ripening, as determined by change of fruit color and screened for (i) the presence of natural dehydration; and (ii) the above described introgression. For example, minimal introgressions containing the wild species allele can be limited to less than 10 cM, less than 5 cM, less than 2 cM and less than 1 cM by using the following markers, CT199, TG163, CT61, and within the region spanning CT61 and TG464. For example markers which can be used to generate a minimal introgression which still enable increasing cuticular water permeability include any of the sequences derived from the ends of the BACs shown in FIG. 3a.

Thus, the present invention also provides a cultivated tomato plant having a genome comprising an introgression derived from a wild *Lycopersicon* spp. said introgression comprising a portion of chromosome 4 of said *Lycopersicon* spp. smaller than a chromosomal fraction extending from telomeric marker TG464 to centromeric marker CT173, said introgression being capable of increasing cuticular water permeability of the cultivated tomato plant.

Once cultivated and genetically modified plants of the present invention are generated (as described above) dehydrated fruits can be generated as follows.

Fruits are allowed to remain on the vine past normal point of ripening. The appearance of dehydration as evidenced by wrinkling of the fruit skin indicates reduced water content in the fruit. Once dehydrated fruits are obtained they may be collected. Alternatively, fruits are collected from the vine and subsequently allowed to dehydrate (e.g., sun-drying, described in length in the Background section.

Thus, the present invention provides polynucleotides and polypeptides which govern cuticular water permeability in plants expressing same and methods of using these for producing dehydrated fruits of commercially valuable crop plants.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262;

3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Plant Material and Measurements—

A set of near-isogenic introgression lines derived from a backcross breeding program based on the inter-specific hybridization of L. esculentum (E) and the wild species L. hirsutum (H), distinguished by the trait of fruit dehydration was developed, as described previously (WO 0113708) as summarized here. Plants of E breeding line 1630 were pollinated with wild species H (LA1777). Hybrid $F_1$ plants were self-pollinated, generating $F_2$ seeds. Three $F_2$ plant were selected based on their high sugars content when ripe. $F_3$ seeds were sown and ten plants of each of the $F_3$ plants of these three $F_2$ selections were grown, and fruit was allowed to remain on the vine past the normal stage of ripening and harvest. Among the $F_3$ plants one plant (F3-203-10) showed the characteristic of sign of fruit dehydration, evidenced by wrinkling of fruit skin. A pedigree breeding program was developed consisted of selfing this $F_3$ individual until the $F_4$ generation followed by intense selection for fruit dehydrating rate. Thereafter, plants were back-crossed to the E breeding line, with the product of this cross being selfed for four additional generations to produce a BC1F4 population. Dehydrating individuals from this population were subjected to another backcross to E, producing hybrid plants that were present with the trait. Two $F_2$ populations (2394 and 2395) were constructed from these $F_1$ individuals.

Initially the selection procedure was based on the phenotype of fruit dehydration and microcracks on the fruit cuticle. Following the development of molecular markers linked to the trait, selection was performed according to the genotype. Cleaved Amplified Polimorphic (CAPS) marker were used as the molecular markers. CAPS were developed using a specific PCR product that was cut by an endonucleases enzymes (see at "DNA Analysis" further below).

Plants were grown in 15-1 pots in a greenhouse, according to standard methods, as previously described (Miron and Schaffer, 1991). Fruit mean weight and dehydration rate were determined by picking and weighing five mature red fruits from each plant, placing them on a net-table at room temperature (about 25° C.) and weighing them every 2-3 days. The presence of microfissures (MF) on the fruit cuticle was verified by either magnifying glass (2×) or binocular microscope (10×).

DNA Analyses—

Genomic DNA was extracted according to Fulton et al. (1995). CAPS (Cleaved Amplified Polymorphism) markers were developed from RFLP markers selected from high-density tomato map (Tanksley et al. 1992), as follows. BlueScript plasmid vectors (Stratagene) containing tomato DNA inserts representing the selected RFLP markers were kindly provided by the Tomato Genome Center in Weizmann Institute of Science, Rehovot, Israel. Genomic DNA insertion segments were partially sequenced at the DNA Analysis Unit in the Hebrew University, Jerusalem, Israel, using T7 and SP6 primers (SEQ ID NO: 1 and 2, respectively). According to these sequence analysis results, sequence-specific PCR primers were designed using the Primer Express Program, version 1.0 (Perkin Elmer Biosystems). A total of approximately 20 markers were designed and these were tested to determine the existence of polymorphisms between the L. esculentum and L. hirsutum parental genotypes as well as between the tomato lines differing in the L. hirsutum-derived trait.

Following are PCR primers for two markers—TG163 and TG587, representing positions on chromosome 4.

```
TG163 F:
5'-TGCAATCCCGAACATGAAGAC-3'      (SEQ ID NO: 3)

TG163 R:
5'-CCTTCTGGTCGCATCTGTGTCT-3'     (SEQ ID NO: 4)

TG587 F:
5'-TCAGGGTGAGGGGTAATAATTGAG-3'   (SEQ ID NO: 5)

TG587 F:
5'-GCTTAAAACTCAAGTCTCCTCGCA-3'   (SEQ ID NO: 6)
```

The amplification reactions were performed in an automated thermocycler (Mastercycle Gradient, Eppendorf, Germany) using thermostable Taq DNA polymerase (Super-Nova Taq Polymerase, JMR Products, Kent, UK). The reactions were carried out in 25 µl final volume that contained 10× reaction buffer, 0.125 mM of each deoxynucleotide, 0.5µ of each primer, 2.5 Unit of Taq polymerase and 50-100 ng of tomato genomic DNA. The conditions were optimized for the annealing temperature for each set of primers and the product fragment size. To identify restriction endonucleases that would generate a polymorphism between the L. esculentum and L. hirsutum alleles, reaction were carried out in 10 µl final volume containing 3.5 µl of PCR product, 1 µl of 10× concentrated restriction enzyme buffer, and 1-3 unit of the appropriate restriction endonuclease. The digestion products were analyzed on 1% gels. DraI and HinF1 were found to be appropriate for TG163 and TG587, respectively, and were used on the segregating populations. A similar procedure was applied for the design of the others CAPS markers.

All BACS (Bacterial Artificial Chromosomes) that were used in this work were provided from Clemson University Genomic Institute (Clemson, N.C., USA), using the Tomato Heinz 1706 BAC Library Filters (LE_HBa). Tomato BAC library filters were screened for a specific BAC clone by a radioactive probe, as described below. that was labeled using the NEBlot™ Kit (New England BioLabs inc. #N1500S) and according to the supplier's instructions. Labeled BAC colonies on the filter were detected using a phosphor-imager device (FLA-5000; FujiFilm). BAC plasmids were purified from the matching E. coli strains using the QIAGEN® Maxi Plasmid Purification Kit (#12263). For "Chromosome Walking" procedure, BACs ends were sequenced using the SP6 and T7 primers and a PCR product was developed according to the BACs end sequence. The new purified PCR product was radioactive labeled and was used for another round of tomato filter colonies detection.

LE_HBa 37B8 BAC clone (Clemson University Genomic Institute, Clemson, N.C. USA) was sub-cloned into the BlueScript II ks+ vector (Stratagene) and sequenced. The 15 kb section was completely sequenced by developing primers and cloning by PCR and sequencing the relevant sections, as described above. DNA sequences were analyzed using the NCBI nucleic acid and translated protein databases by using the BLAST software (Altschul et al., 1990).

RNA and Quantitative RT-PCR Analyses—

For the preparation of cDNA, total RNA was extracted, as previously described (Miron et al, 2002). Total RNA was used as a template for first strand cDNA synthesis with the Super-script II pre-amplification system reverse transcriptase kit (Gibco BRL, LifeTechnologies, UK) at 42° C. according to the supplier's instructions.

PCR Primers—

Specific primers with short amplicons for on-line quantitative PCR were designed with the Primer Express Program, version 1.0 (Perkin Elmer Biosystems) based on the sequences derived from the BAC sequencing of the three ORFs: 1) ZINC gene, forward, 5'-AATAATGCGAATC-GAATCACTA-3' (SEQ ID NO: 7) and reverse, 5'-AAGGCTAAATCTCCTCCTTTCT-3' [SEQ ID NO: 8, amplicon 140 bp (SEQ ID NO: 9)]. 2) DBP gene, forward, 5'-TGGATAAGCGGACGACTCTATTG-3' (SEQ ID NO: 10) and reverse, 5'-CTGTTGTTTGGGAAGTGGCTTCT-3' [SEQ ID NO: 11, amplicon 116 bp (SEQ ID NO: 12)]. 3) PUT gene, forward, 5'-CTCTCCTTGGCCCAAGGCT-CAA-3' (SEQ ID NO: 13) and reverse, 5'-CAGCTT-TAGTGGTATCTCTCATCA-3' [SEQ ID NO: 14, amplicon 205 bp (SEQ ID NO: 15)]. Actin was used as a reference gene, with the following primers, based on Gene bank accession No. BF096262: forward, 5'-CACCATTGGGTCT-GAGCGAT-3' (SEQ ID NO: 16) and reverse, 5'-GGGCGA-CAACCTTGATCTTC-3' [SEQ ID NO: 17, amplicon 251 bp (SEQ ID NO: 18)].

The cDNA was used as template for quantitative PCR amplification on the GeneAmp 5700 Sequence Detection System (PE Biosystems) using SYBR Green Master Mix containing AmpliTaq Gold, According to manufacture's instructions (PE Biosystems). The thermocycler was programmed for 40 cycles for all reactions, with the first step of denaturation at 95° C. for 30 sec, the annealing temperature of 62° C. for 15 sec, and extension temperature of 72° C. for 30 sec. Data acquisition was done at 77° C. for 30 sec. Preliminary dissociation analyses of the PCR products showed that product remaining above 77° C. was the specific PCR product. Standard curves containing logarithmically increasing known cDNA levels were run with each set of primers, in addition to the actin primers for normalization. All real time PCR products were tested on 2% agarose gel and were sent for sequencing for identity approval.

Cloning of Full-Length Put Gene—

Full length sequence of the putative protein gene (put) was amplified from cDNA that was extracted from HH line fruit (10 days after anthesis), using the following primers: Put forward, 5'-GTAGTACTATATAAACCATGTGAG-3' (SEQ ID NO: 19) and reverse, 5'-CATATGTT-GACATATCTAATG-3' (SEQ ID NO: 20). The full length gene [(SEQ ID NO: 20), 930 bp) was cloned to pGEM-T easy vector (promega) using T-A cloning procedure, and then was sub-cloned to BlueScript II ks+ vector (Stratagene) using the EcorI (NEB #R0101) endonuclease. The put gene (SEQ ID NO: 21) was again sub-cloned between the cauliflower 35S promoter and the n-terminator sites of the pBIN PLUS binary vector (Ghosh et al., 2002) using the XhoI (NEB #R0146) and XbaI (NEB #R0145) endonucleases.

Transgenic Plants—

Constructed vector comprising the put gene under the 35S promoter was transformed into *E. coli* (strain DH5alpha, Stratagene), and then were retransformed into EHA105 *Agrobacterium* electro-competent cells using the method described by Walkerpeach and Velten (1994). Plasmids were prepared using a mini-prep kit (Qiagen #12143) and re-transformed to pBIN PLUS for sequencing to insure the absence of deletions and other cloning inaccuracies.

Tomato transformation experiments were carried out using the cv MicroTom as described by Meissner et al. (1997) and cv. MP1 as described by Barg et al. (1997). Transgenic shoots were rooted on Murashige and Skoog basal medium (Duchefa, Haarlem, The Netherlands) supplemented with 1 mg L$^{-1}$ zeatin (Duchefa #Z0917), 100 mg L$^{-1}$ kanamycin and 100 mg L$^{-1}$ Chlaforan. Standard practices of growing the transformed plants are carried out.

EXAMPLE 1

Inheritance Analysis of the Dehydration Trait

The inheritance of the trait of appearance of micro-fissures (MF) on the fruit skin was determined in two independent segregating $F_5$ populations (lines 2394 and 2395) based on a cross between a standard small fruited cultivar (line 1815) and an advanced introgression line exhibiting the trait of dehydration (line 1881). The distribution pattern of the appearance of micro-fissures in the segregating populations was according to a ratio of 3:1 for Micro-fissured: standard cuticle, with chi-square probability values of 0.546 and 0.864 for 2394 and 2395 populations, respectively (Table 1, below).

TABLE 1

Segregation pattern of microfissure and dehydration phenotypes in segregating populations 2394 and 2395.

| 2395 | | | 2394 | | |
|---|---|---|---|---|---|
| Phenotype | No | Probability | Phenotype | No | Probability |
| N | 16 | 0.272 | N | 15 | 0.234 |
| Y | 39 | 0.709 | Y | 49 | 0.765 |
| Total | 55 | 1.000 | Total | 64 | 1.000 |
| $X^2$ value: 0.029 | | | $X^2$ value: 0.424 | | |
| Prob of $X^2$: 0.864 | | | Prob of $X^2$: 0.546 | | |

N—non-dehydrating;
Y—dehydrating;
No—number of individuals in population.

This distribution pattern is characteristic for a single gene inheritance with dominant/recessive allelic relations.

The trait of fruit dehydration (CWP) segregated according to a 3:1 ratio in population 2394 while in population 2395 segregation was according to a 1:2:1 ratio with approximately half of the population dehydrating but at an intermediate rate of dehydration. Therefore, it is concluded that the allelic relations are either completely dominant or semi-dominant, depending on the genetic background of the population (FIGS. 1a-b). From the above it can be concluded that the trait of fruit CWP is inherited as a single gene trait, which is termed herein as Cwp.

EXAMPLE 2

Fine Mapping of Cwp Gene

Based on the high-density tomato RFLP map (Tanksley et al. 1992) a set of CAPS (Cleaved amplified polymorphism) markers were designed. Loci representing various genomic positions, including markers linked to QTLs for reticulated epidermis (Fulton, et al., 2000, markers TG464, TG477, CT68 and TG68 localized on chromosomes 4, 6, 8, 12, respectively) were investigated for analysis of linkage with the trait of micro-fissures. Each polymorphic PCR-based molecular marker was applied to both parents and a set of 48 $F_2$ individuals segregating for the trait.

Based on the initial set of markers the Cwp gene was mapped to the telomeric portion of chromosome 4, linked to CT199 marker by an estimated distance of approximately 3 cM (2 recombination events in 96 gametes, FIG. 2a). For finer mapping of the telomeric portion of chromosome 4 an additional group of CAPS markers were designed for a cluster of markers located throughout this chromosomal segment. The chromosomal introgression segment from the *L. hirsutum* parent was localized between the TG163 and TG464 markers (FIG. 2b). This introgression represents the *L. hirsutum* segment in the near-isogenic line that was used as the dehydrating donor parent in this analysis.

In order to further narrow down the introgression size a larger $F_2$ population (over 200 individuals) was investigated with PCR-based markers between CT199 and TG464 markers. A closely linked cluster (<1.5 cM) of molecular markers was defined as flanking the Cwp gene (FIG. 2c) and based on this study the Cwp gene was located between TG464 and CT61 (0.5 cM).

EXAMPLE 3

Positional Cloning of Cwp Gene

The localization to this small introgression allowed for the positional cloning of Cwp. For this purpose an additional 3500 segregating progeny (7000 gametes) of a heterozygous individual derived from the near-isogenic line were subjected to CAPS marker analysis with the marker TG464 and CT61, revealing 12 recombinants (0.34 cM compared with 0.5 cM between the same markers in the "first round" of fine mapping). A set of 5 contiguous BACs bridging the linked markers TG464 and CT61 was identified and assembled using the chromosome walking technique. In brief, this was accomplished by sequencing the BAC end and using the BAC end as a probe to identify a contiguous BAC.

In order to place the new BAC with respect to the introgression, and to produce a higher resolution map polymorphic CAPs for the two species were developed and the recombinants were tested for these new markers.

The 5 contiguous BACs created a bridge between CT61 and TG464 CAPS markers (FIG. 3a). For each of the 12 recombinant plants 10 selfed progenies were grown, genotyped with the appropriate segregating markers and analysed for dehydration and the appearance of micro-fissures. Of the 12 recombination events initially identified, 3 were further localized between the two ends of BAC 37B8 (FIG. 3a—area restricted by two broken lines) indicating that Cwp was located in the 37B8 BAC. To further resolve the recombination events, BAC 37B8 was sub-cloned and the smaller fragments were assembled in order and a segment of approximately 15,000 bp (15 kb) was identified, within which the Cwp gene was located. (FIG. 3b, mapping and sub-cloned contigs data at a lower resolution are not presented).

EXAMPLE 4

Bioinformatical Analysis of the Candidate Genes

The segment of 15 kb in BAC 37B8 described in Example 3 was sub-cloned into the Bluescript vectors (Stratagene), sequenced and assembled using the SEQUENCHER software package (Gene Codes Corporation).

A bioinformatics analysis of the 15 kb sequence after analysis by the BLAST program (BLASTP, NCBI, http://www.ncbi.nlm.nih.gov) revealed three candidate open reading frames (ORFs, FIG. 4). The first ORF showed a similarity to a protein of unknown function from *Arabidopsis thaliana* (GenBank Accession No. NP_189369.1) (protein Identity—44%, Homology—61%). This protein has two domains. The first one is RING-finger domain (rps-BLAST—NCBI Conserved Domain Search), a specialized type of Zn-finger of 40 to 60 residues that binds two atoms of zinc, and is probably involved in mediating protein-protein interactions (Borden, 1998). It was identified in proteins with a wide range of functions, such as viral replication, signal transduction, and development. It has two variants, the C3HC4-type and a C3H2C3-type (RING-H2 finger), which have different cysteine/histidine pattern. The other domain is DUF23 and it is domain of unknown function. It is part of a family that consists of an approximately 300 residue long region found in *C. elegans* and *drosophila* proteins. This region contains several conserved cysteine residues and several charged amino acids that may function as catalytic residues. This ORF was termed "Zinc". Interestingly, the homology of the tomato Zinc to the *Arabidopsis* homolog is not at the site of the "Ring finger" but only at DUF23 one and the "Ring finger" domain region is missing at Zinc tomato gene.

The second ORF showed similarity to a DNA-binding bromodomain-containing protein (*Arabidopsis thaliana* GenBank Accession No. NP_974153.11, protein identity—37%, Homology 56%). This gene is a part of a DNA binding protein family that is associated with acetylation regulation of proteins, DNA and chromatin and are part of histone acetyltransferase regulation (Dhalluin et al., 2000). We termed this gene "DBP" (DNA Binding Protein).

The third ORF had similarity to a protein described merely as an "expressed protein" (*Arabidopsis thaliana* At4g38260, GenBank Accession No. NP_568038.1) (protein Identity—48%, homology—67%). It contains a domain of unknown function (DUF833). It is part of a family that is found in eukaryotes, prokaryotes and viruses and has no known function. One member has been found to be expressed during early embryogenesis in mice (Halford et al., 1993). This gene was termed "PUT" (putative). None of these three candidate genes showed any similarity or homology to genes that participate in known steps of cuticle biosynthesis metabolism.

EXAMPLE 5

Expression Analysis of Candidate Genes

In order to determine which of the three candidate genes is associated with tomato fruit cuticle development, the expression level of each of the three genes in the near-isogenic lines differing in their Cwp allele was measured [*L.* hirsutum dehydrating allele, (HH), and *L. esculentum* not dehydrating allele, (EE), FIGS. 5a-b]. mRNA from ovaries and fruits of the following stages was extracted: anthesis, 5 and 15 days after anthesis, and at immature green, mature green and breaker developmental stages (FIGS. 5a-b). Fruit specimens were taken from the same segregating population that was used for the positional cloning procedure. The expression of each of the genes was examined by RT-PCR. DBP was expressed only at the ovary stage and equally in both genotypes (HH and EE) thereby indicating that the expression of this gene is not associated with the phenotypic trait (FIG. 5b). Expression of the Zinc gene was not observed at any fruit stage in either genotype, similarly indicating that its expression is not associated with the trait of dehydration (not shown).

Only PUT was expressed in the young stages of the developing fruit and, furthermore, was expressed differentially only in fruit of the dehydrating genotypes with the *L. hirsutum* allele for Cwp (HH) (FIG. 5a). The highest expression observed in this study was at the fruitlet stage of 15 days after anthesis.

In order to confirm the differential expression pattern of the PUT gene, the expression of this gene in additional populations derived from the M82 tomato industry cultivar was analyzed. One population was an $F_2$ population derived from a heterozygote individual, originating from the hybridization of a dehydrating line (line 2168) with the M82 determinate cultivar. We examined the expression of all three segregating genotypes (HH, HE, EE), at the stage of 5-15 days after anthesis (the stage with the highest expression levels in the first expression analysis). As shown in FIG. 6, a classical Mendelian expression pattern of PUT gene was found, with the HH genotypes showing highest expression levels, the heterozygous HE individuals showing approximately half the expression level, and the EE genotypes lacking expression (first three bars in FIG. 6).

In addition, the expression of the PUT gene was examined in another NIL (near isogenic line) population the introgression line 4.4 derived from the interspecific hybridization of *L. esculentum* (M82) and an additional wild species *L. pennellii*, containing the analogous introgression as the *L. hirsutum*-derived genotypes described here (Eshed and Zamir, 1994). This population represents another wild allele of the PUT gene, and the fruit of IL4.4 also show microfissures and dehydrate. Similar to the *L. hirsutum* derived populations, the *L. penellii* derived introgression containing the *L. penellii* allele for Cwp (IL 4.4) showed expression of the PUT gene in the young fruitlets, compared to M82 (FIG. 6, last two bars).

Transgenic Tomato Plants Expressing the PUT Gene

In order to show that the expression of the Put gene is associated with the unique cuticular development trait transgenic tomato plants were developed with the PUT gene under the control of the 35S promoter (using the pBIN PLUS binary vector as described). The phenotypic trait is observed in the transgenic plants, indicating that the expression of Put is associated with the trait.

In order to determine the gene dosage of the individual segregating T1 plants derived from the selfing of the initial transgenic plants 50-70 seed from each T1 plant were seeded on ½ MS medium containing 100 mg/ml Kanamycin. Following germination, the percentage of seedlings with normal roots was determined. When 100% of the seedlings exhibited normal roots growth, that T1 plant was considered homozygous for the transgene. Approximately 75% T2 seedlings with normal roots indicated that the T1 plant was heterozygous for the transgene. Other ratios, though not observed here, might indicate the existence of two or more unlinked copies of the transgene. Sixteen T1 individuals from two independent T1 segregating populations were analyzed to determine their allelic makeup. These classifications were then used to determine the relationship between allelic dosage of the PUT gene and the phenotypic traits.

As shown in FIGS. 7a-b, the phenotypic trait of microfissures (MF-) on the fruit cuticle was already observed at the $T_0$ generation. From 20 independent $T_0$ transgenic individuals 4 plants (MF1-1, MF1-4, MF1-8, MF1-12) showed varying levels of MF on fruit skin. In addition, these transgenic plants showed higher dehydrating rate than the wild type fruit (FIG. 7b).

Two segregating $T_1$ populations were grown and tested for? MF presence and dehydrating rates. FIGS. 8a-b show the effect of the PUT transgene copy number on microfissures severity (scale between 1 to 5, FIG. 8a) and weight loss percentage of the fruit (after 14 days at room temperature, FIG. 8b). The number of PUT gene copies were determined as in the materials and methods section.

FIGS. 9a-b show a comparison between transgenic tomato individuals ($T_1$ generation) expressing no copies, analogous to wild type, and two copies of the PUT gene from the wild tomato species *Solanum habrochaites* S. FIG. 9a—Scanning electron micrograph presenting the intact surface of the fruit from an individual with no copies of the PUT gene (0 copies) and the micro-fissured fruit of an individual with two copies of the transgene. FIG. 9b—Drying rate comparison between an individual with no copies of the PUT gene (0 copies) and an individual with two copies (2 copies).

These results clearly show that the expression of the PUT gene is causal to the phenotype of microfissures and fruit dehydration.

Phylogenetic analysis based on gene sequences indicates that cwp is part of a gene family represented by three members in *Arabidopsis* (FIGS. 10a-b). There is an additional tomato homologue (CWP2) showing 30% homology to the Lecwp1 gene, which is indeed expressed in cultivated tomatoes (EST No. AW621927).

Interestingly, this homologue maps to tomato chromosome 2-1 where there is a reported QTL for tomato fruit epidermal reticulation (Frary et al, 2004). Developing fruit of the solanaceous cultivated pepper (*Capsicum annum*) also express a cwp homologue highly similar (87%) to the Lecwp1 gene in its epidermal tissue and pepper fruit are characterized by the horticultural problem of post-harvest water loss, as well as by the desirable trait of fruit dehydration in paprika cultivars. Therefore it is likely that homologues of the CWP gene may also contribute to cuticular modification and water permeability.

These results indicate that the expression of the cwp gene leads to a structurally modified cuticle (based on weight and TEM) which presumably undergoes fissuring during fruit expansion due to reduction in elasticity. However, this phenomenon is observed only in fruit with a highly developed fruit cuticle such as the astomatous thick skinned cultivated tomato and is not apparent in fruit of the wild species, with their characteristic thinner cuticle. The deposition of cuticular components during cultivated tomato fruit development undergoes a surge during the transition from the immature to the mature green stage and it is reasonable that the this coincides with the observation of the microfissure phenotype.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Other References are Cited in the Application

Aharoni A Dixit S Jetter R Thoenes E Arkel G Pereira A (2004) The SHINE Glade of AP2 domain transcription factors activates wax biosynthesis, alters cuticle properties and confers drought tolerance when overexpressed in *Arabidopsis*. Plant Cell (in press).

Altschul S F Gish W Miller W Myers E W Lipman D J (1990) Basic local alignment search tool. J. Mol. Biol. 215: 403-410.

Arts M G M Keijzar C J Steikema W J Pereira A (1996) Molecular characterization of the CER1 gene of *Arabidopsis* involved in epicuticular wax biosynthesis and pollen fertility. Plant Cell 7: 2115-2127.

Baker, (1982) In: The Plant cuticle, Editors: D. F. Cutler, K. L. Alvin and C. E. Price, London, Academic Press, Bakker J C (1988) Russeting (cuticle cracking) in glasshouse tomatoes in relation to fruit growth. J. Hort. Sci. 63 (3): 459-463.

Barg R Pilowsky M Shabtai S Carni N Alejandro D Szechtman B D Salts Y (1997) The TYLCV-tolerance tomato line MP-1 is characterized by superior transformation competence. J. Exp. Bot. 48 (316): 1919-1923.

Blee E Schuber F (1993) Biosynthesis of cutin monomers: involvement of a lipoxygenase/peroxygenase pathway. Plant J. 4: 113-123.

Borden K L (1998) RING fingers and B-boxes: zinc-binding protein-protein interaction domains. Biochem. Cell Biol. 76(2-3): 351-358.

Chen X Goodwin S M Boroft V L Liu X Jenks M A (2003) Cloning and characterization of the WAX2 gene of *Arabidopsis* involved in cuticle membrane and wax production. Plant Cell 15: 1170-1185.

Considine J Brown K (1981) Physical aspects of fruit growth. Plant Physiol. 68: 371-376.

Conter S D Burns E E Leeper P W (1969) Pericarp anatomy of crack-resistant and susceptible tomato fruits. J. Amer. Soc. Hort. Sci. 94: 136-137.

Dhalluin C Carlson J E Zeng L He C Aggarwal A K Zhou M M (2000) Structure and ligand of a histone acetyltransferase bromodomain. Nature 399(6735): 491-496.

Emmons C L W Scott J W (1997) Environmental and physiological effects on cuticle cracking in tomato. J. Amer. Hort. Sci. 122 (6): 797-801.

Ehret D L Helmer T Hall J W (1993) Cuticle cracking in tomato fruit. J. Hort. Scien. 68 (2) 195-201.

Eshed, Y and Zamir D. (1995) n introgression line population of *Lycopersicon penellii* in the cultivated tomato enables the identification and fine mapping of yield associated QTL. Genetics 141:1147-1162.

Flebig A Mayfield J A Milley N L Chau S Fischer R L Prauss D (2000) Alterations in CER6, a gene identical to CUT1, differentially affect long-chain lipid content on the surface of pollen and stems. Plant Cell 12: 2001-2008.

Fulton T M, Chunwongse J, Tanksley S D (1995) Microprep protocol for extraction of DNA from tomato and other herbaceous plants. Plant Mol Biol Rep 13: 207-209.

Fulton T M Grandillo S Beck-Bunn T Fridman E Frampton A Lopez J Petiard V Uhling J Zamir D Tanksley S D (2000) Advanced backcross QTL analysis of a *lycopersicon esculentum×lycopersicon parviflorum* cross. Theor. Appl. Genet. 100: 1025-1042.

Ghosh S B Nagi L H S Ganaphthi T R Khurana P S M Bapat V A (2002) Cloning and sequencing of potato virus Y coat protein gene from Indian isolate and development of transgenic tobacco for PVY resistance. Curr. Sci. 82: 855-859.

Halford S Wilson D I Daw S C Roberts C Wadey R Kamath S Wickremasinghe A Burn J Goodship J Mattei M G (1993) Isolation of a gene expressed during early embryogenesis from the region of 22q11 commonly deleted in DiGeorge syndrome. Hum. Mol. Genet. 2(10):1577-1582.

Holloway G J (1982) Structure and histochemistry of plants cuticular membranes. In: Cutler D F Cutler K L A Price C E, The Plant Cuticle. Academic Press, London, UK, pp. 33-44.

Hooker T S Millar A A Kunst L (2002) Significance of the expression of the CER6 condensing enzyme for cutucular wax production in *Arabidopsis*. Plant Physiol. 129, 1568-1580.

Kolattukudy P E (1980) Biopolyester membranes of plants: cutin and suberin. Science 208 (30): 990-999.

Koornneef M Anhart C J Theil F (1989) A genetic and phenotypic description of *eceiferum* (cer) mutants of *Arabidopsis thaliana*. J. Hered. 80: 118-122.

Koske T J Pallas J E Jones J B (1980) Influence of ground bed heating and cultivar on tomato fruit cracking. Hortscience 15 760-762.

Kunst L Samuels A L (2003) Biosynthesis and secretion of plants cuticular wax. Prog. Lipid. Res. 42(1): 51-80.

Kurata T Kawabata A C Sakuradani E Shimizu S Okada K Wada T (2003) The *yore-yore* gene regulates multiple aspects of epidermal cells differentiation in *Arabidopsis*. Plant J. 36: 55-66.

Lownds N K Banaras M Bosland P W (1993) Relationships between postharvest water loss and physical properties of pepper fruit (*Capsicum annuum* L.). HortScience 28 (12): 1182-1184

Meissner R Jacobson Y Melamed S Levyatuv S Shalev G Ashri A Elkind Y Levy A (1997) A new model system for tomato genetics. Plant J 12: 14651472.

Millar A A Clemens S Zachgo S Giblin E M Taylor D C Kunst L (1997) CUT1, an *Arabidopsis* gene required for cuticular wax biosynthesis and pollen fertility, encodes a very-long-chain fatty acid condensing enzyme. Plant J. 12: 121-131.

Miron D Schaffer A A (1991) Sucrose phosphate synthase, sucrose synthase and invertase activity in developing fruit of *lycopersicon esculentum* Mill. And Bonpl. Plant Physiol. 95: 623-627.

Miron D Petreikov M Carmi N Shen S Levin I Granot D Zamski E Schaffer A A (2002) Sucrose uptake, invertase localization and gene expression in developing fruit of *lyconpersicon esculentum* and the sucrose-accumulating *lycopersicon hirsutum*. Physiol. Plant. 115: 35-47.

Monforte A J Freidman E Zamir D Thankslry S D (2001) Comparison of a set of allelic QTL-NILs for chromosome 4 of tomato; Deductions about natural variation and implications for germplasm utilization. Theor. Appl Genet. 102:572-590.

Nawrath C (2000) The biopolymers cutin and suberin. In: Somerville C R Meyerowitz E M, The *Arabidopsis* Book. Rockville, Md.: American society of Plant Biologist, Pp. 1-14.

Ojimelukwe P C (1994) Effects of processing methods on ascorbic acid retention and sensory characteristic of tomato products. J. Food Sci. Thechnol. 31: 247-248.

Peet M M (1992) Fruit cracking in tomato. HortTechnology 2 (2): 216-223.

Peet M M Willits D H (1995) Role of excess water in tomato fruit cracking. HortScience 30 (1): 65-68.

Pruitt R E VIIIe-Catzada J P Ploense S E Grossnlklaus U Lolle S J (2000) FIDDLEHEAD, a gene required to suppress epidermal cell interaction in *Arabidopsis*, encodes a putative lipid biosynthesis enzyme. Proc. Natl. Acad. Sci. 97: 1311-1316.

Reina J J Heredia A (2001) Plant cutin biosynthesis: the involvement of a new acyltransferase. Trends Plant Sci. 6: 296.

Riederer M Schreiber L (2001) Protecting against water loss: analysis of the barrier properties of plant cuticles. J. Exp. Bot. 52 (363): 2023-2032.

Tanksley S D Ganal M W Giovannoni J J Grandillo S Martin G B Messeguer R Miller J C Miller L Paterson A H Pineda O Roder M S Wing R A Wu W Young N D (1992) High density molecular linkage maps of the tomato and potato genomes. Genetics 132: 1141-1160.

Schnurr J Shockey J Browse J (2004) The acyl-CoA synthetase encoded by LACS2 is essential for normal cuticle development in *Arabidopsis*. Plant Cell 16(3): 629-642.

Schönherr J (1976a) Water permeability of isolated cuticular membranes: The effect of pH and cations on diffusion, hydrodynamic permeability and size of polar pores in cutin matrix. Planta 128: 113-126.

Schönherr J (1976b) Water permeability of isolated cuticular membranes: The effect of cuticular waxes on diffusion of water. Planta 131: 159-164.

Schönherr J Schmidt H W (1979) Water permeability of plant cuticle. Planta 144: 391-400.

Todd J Post-Beittenmiller D Jaworski J G (1999) KCS1 encodes a fatty acid elongase 3-ketoacyl-CoA synthase affecting wax biosynthesis in *Arabidopsis Thaliana*. Plant J. 17: 119-130.

Tukey L D (1959) Observations on the russeting of apples grown in plastic bags. Proc. Am. Soc. Hortic. Sci. 74: 30-39.

Vogg G Fischer S Leide J Emmanuel E Jetter R Levy A A Riederer M (2004) Tomato fruit cuticular waxes and their effects on transpiration barrier properties: functional characterization of a mutant deficient in a very-long-chain fatty acid beta-ketoacyl-CoA synthase. J. Exp. Bot. 55(401): 1401-1410.

Voisey P W Lyhall L H Kloek M (1970) Tomato skin strength—its measurement and relation to cracking. J. Amer. Soc. Hort. Sci. 95 (4): 485-488.

Walkerpeach C and Velten J (1994) *Agrobacterium*—mediated gene transfer to plant cells cointegrate and binary vector system. In: Gelvin S Schilperoort R, Plant Molecular Biology Manual. Kluwer Academic Publishers, Belgium, Pp. 1-19.

Wilson L A Sterling C (1975) Studies on the cuticle of tomato fruit I. Fine structure of the cuticle. Z. Pflanzenphysiol. 77: 359-371.

Wellesen K Durst F Pinot F Benveniste L Nettesheim K Wisman E Steiner-Langa S Saedler H Yapheremov A (2001) Functional analysis of the LACERATA gene of *Arabidopsis* provides evidence for different roles of fatty acid omega-hydroxylation in development. Proc. Natl. Acad. Sci. USA 98: 9694-9699.

Yahhremov A Wisman E Huijser C Wellsen K (1999) Characterization of the FIDDLEHEAD gene of *Arabidopsis* reveals a link between adhesion response and cell differentiation in the epidermis. Plant Cell 11: 2187-2201.

Young P A (1947) Cuticle cracks in tomato fruits. Phytopathology 37: 143-145.

What is claimed is:

1. A cultivated tomato plant having a genome comprising an introgression derived from a wild *Lycopersicon hirsutum* said introgression consisting of a portion of chromosome 4 of said *Lycopersicon hirsutum* smaller than a chromosomal fraction extending from telomeric marker TG464 to centromeric marker, CT61 and includes TG464 and the nucleic acid sequence encoding cwp1, said introgression being capable of increasing cuticular water permeability of the fruit of the cultivated tomato plant.

2. A tomato fruit of the tomato plant of claim 1.

3. A seed of the tomato plant of claim 1.

4. A method of producing a dehydrated tomato, the method comprising:
   (a) growing the plant of claim 1;
   (b) allowing the fruit to dehydrate on the plant; and subsequently
   (c) collecting the dehydrated fruit.

5. A method of producing a dehydrated tomato, the method comprising:
   (a) growing the plant of claim 1;
   (b) removing the fruit from the plant prior to dehydration thereof; and subsequently
   (c) allowing the fruit to dehydrate.

6. A method of generating a cultivated tomato plant with increased cuticular water permeability, the method comprising:
   (a) hybridizing *Lycopersicon esculentum* plants with *Lycopersicon hirsutum* plants so as to generate F1 plants;
   (b) self pollinating said F1 plants repeatedly;
   (c) crossing said self pollinated plants with *L. esculentum* plants; and
   (d) identifying fruits of steps (b) or (c) having increased cuticular water permeability by identifying an introgression derived from said *Lycopersicon hirsutum*, said introgression consisting of a portion of chromosome 4 of said *Lycopersicon hirsutum*, smaller than a chromosomal fraction extending from telomeric marker TG464 to centromeric marker CT61 and comprising the nucleic acid sequence encoding cwp1, said introgression being capable of increasing cuticular water permeability of the cultivated tomato plant.

* * * * *